(12) United States Patent
Leberer et al.

(10) Patent No.: US 7,429,449 B2
(45) Date of Patent: Sep. 30, 2008

(54) **POTASSIUM CHANNEL MUTANTS OF THE YEAST *SACCHAROMYCES CEREVISIAE* AND THEIR USE FOR SCREENING EUKARYOTIC POTASSIUM CHANNELS**

(75) Inventors: Ekkehard Leberer, Germering (DE); Thomas Leeuw, Greifenberg (DE); Allegra Ritscher, München (DE)

(73) Assignee: sanofi-aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/758,036

(22) Filed: Jan. 11, 2001

(65) Prior Publication Data
US 2003/0190693 A1 Oct. 9, 2003

(30) Foreign Application Priority Data
Jan. 11, 2000 (DE) ............................. 100 00 651

(51) Int. Cl.
C12Q 1/68 (2006.01)
G01N 33/53 (2006.01)
G01N 33/569 (2006.01)
C12N 1/00 (2006.01)

(52) U.S. Cl. ........................... 435/6; 435/7.2; 435/7.31

(58) Field of Classification Search ................ 435/471; 536/23.1
See application file for complete search history.

(56) References Cited

U.S. PATENT DOCUMENTS 5,795,770 A * 8/1998 Gaber ...................... 435/254.2
2003/0165806 A1 * 9/2003 Pausch ......................... 435/4

FOREIGN PATENT DOCUMENTS

EP 0 641 860 A2 8/1995

OTHER PUBLICATIONS

Ketchum et al. A new family of outwardly rectifying potassium channel proteins with two pore domains in tandem. Nature vol. 376:690-695, 1995.*
Fairman et al. Potassium uptake through TOK1 potassium in the budding yeast. J. Membrane Biol. vol. 168:149-157, Mar. 15, 1999.*
Tang et al. Functional expression of a vertebrate inwardly rectifying K+ channel in yeast. Mol Biol. of the Cell vol. 6: 1231-1240, 1995.*
Rampe et al. The antipsychotic agent sertindole is a high affinity antagonist of the human cardiac potassium channel HERG. J. Pharm. and Exptl. Therapeutics. vol. 286(2):788-793, 1998.*
Takekawa et al. EMBO 16: 4973-4982, 1997.*
A Rapidly Activating and Slowly Inactivating Potassium Channel Cloned from Human Heart, Functional Analysis after Stable Mammalian Cell Culture Express, Dirk J. Snyders, Michael M. Tamkun, Paul B. Bennett, Vanderbilt Univ. School of Medicine, Nashville, TN, J. Gen. Physiol. The Rockefeller University Press 0022-1295/943/04/0513/31, vol. 101, pp. 513-543, Apr. 1993.

Gaber, R. F. et al., "TRK1 Encodes a Plasma Membrane Protein Required for High-Affinity Potassium Transport in *Saccharomyces cerevisiae*", Molecular and Cellular Biology, Jul. 1988, pp. 2848-2859, vol. 8, No. 7.
Güldener, U. et al., "A new efficient gene disruption cassette for repeated use in budding yeast", Nucleic Acids Research, 1996, pp. 2519-2524, vol. 24, No. 13, Oxford University Press.
Richelson, E., "Preclinical Pharmacology of Neuroleptics: Focus on New Generation Compounds", J Clin Psychiatry, 1996, pp. 4-11, vol. 57, Suppl 11.
Sanguinetti, M. C. et al., "Molecular physiology of cardiac delayed rectifier $K^+$ channels", Heart Vessels, 1997, pp. 170-172, Suppl. 12, Springer-Verlag.
Yamada, M. et al., "G Protein Regulation of Potassium Ion Channels", Pharmacological Reviews, 1998, pp. 723-757, vol. 50, No. 4.
Drici, M. D. et al., "Cardiac $K^+$ cahnnels and drug-acquired long QT syndrome", Thérapie, 2000, pp. 185-193, vol. 55.
Curran, M.E., et al; "Molecular cloning, characterization, and genomic localization of a human potassium channel gene"; Genomics; 1992; pp. 729-737; vol. 12; Academic Press, Inc.
Dascal, N. et al; "Atrial G protein-activated $K^+$ channel: Expression cloning and molecular properties"; Proc. Natl. Acad. Sci. USA; Nov. 1993; pp. 10235-10239; vol. 90.
Fairman, C., et al; "Potassium uptake through the TOK1 $K^+$ channel in the budding yeast"; J. Membr. Biol.; 1999; pp. 149-157; vol. 168; Springer-Verlag New York Inc.; 1999.
Fedida, D. et al; "The 1997 Stevenson Award Lecture. Cardiac $K^+$ channel gating: cloned delayed rectifier mechanisms and drug modulation" Can. J. Physiol. Pharmacol; 1998; pp. 77-89; vol. 76; NRC Canada; 1998.
Gaber, R.F. et al; "TRK1 encodes a plasma membrane protein required for high-affinity potassium transport in *Saccharomyces cerevisiae*" Mol. Cell Biol.; 1988; pp. 2848-2859; vol. 8; American Society for Microbiology; 1988.
Goldstein, S.A. et al; "Three new dominant drug resistant cassettes for gene disruption in *Saccharomyces cerevisiae*"; Yeast; 1999; pp. 1541-1553; vol. 15; John Wiley & Sons, Ltd.
Goldstein, S.A. et al; "ORK1, a potassium-selective leak channel with two pore domains cloned from *Drosophila melanogaster* by expression in *Saccharomyces serevisiae* "; Proc. Natl. Acad. Sci. USA; Nov. 1996; pp. 13256-13261; vol. 93.
Guldener, U. et al; "A new efficient gene disruption cassette for repeated use in a budding yeast"; Nucleic Acids. Res; 1996; pp. 2519-2524; vol. 24; Oxford University Press.
Ikeda, K. et al; "Functional coupling of the nociceptin/orphanin FQ receptor with the G-protein-activated $K^+$(GIRK) channel"; Brain Res. Mol. Brain Res.; 1997; pp. 117-126; vol. 45; Elsevier Science B.V.

(Continued)

Primary Examiner—David Guzo
Assistant Examiner—Michele K. Joike
(74) Attorney, Agent, or Firm—MDIP LLC

(57) ABSTRACT

The invention relates to processes for identifying inhibitors and activators of eukaryotic potassium channels, in which a mutated *S. cerevisiae* cell is used whose endogenous potassium channels TRK1, TRK2 and TOK1 are not expressed functionally, but which expresses heterologously a eukaryotic potassium channel to be studied. Other subject matters of the invention are mutated *S. cerevisiae* cells which do not express TRK1, TRK2 and TOK1, and the preparation and use of these mutated *S. cerevisiae* cells.

9 Claims, 14 Drawing Sheets

OTHER PUBLICATIONS

Figure 1:
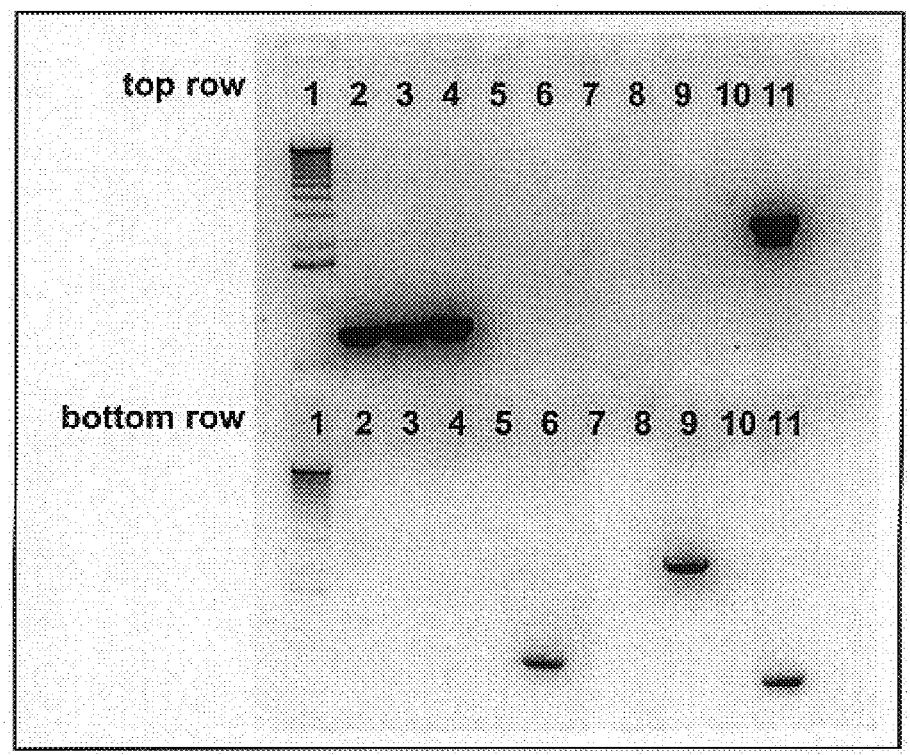

Itoh, T. et al; "Genomic organization and mutational analysis of HERG, a gene responsible for familial long QT syndrome"; Hum. Genet.; 1998; pp. 435-439; vol. 102; Springer-Verlag 1998.

Jan, L. Y. et al; "Cloned potassium channels from eukaryotes and prokaryotes"; Annu. Rev. Neurosci.; 1997; pp. 91-123; vol. 20; Annual Reviews Inc.

Jelacic, T.M. et al; "Functional expression and characterization of G-protein-gated inwardly rectifying $K^+$ channels containing GIRK3" J. Membr. Biol. 1999; pp. 123-129; vol. 169; Springer-Verlag New York Inc.; 1999.

Ketchum, K.A. et al; "A new family of outwardly rectifying potassium channel proteins with two pore domains in tandem"; Nature; Aug. 24, 1995; pp. 690-695; vol. 376

Ko, C.H. et al; "TRK2 is required for low affinity $K^+$ Trasport in Saccharomyces cerevisiae"; Genetics; Jun. 1990; pp. 305-312; vol. 125; The Genetics Society of America.

Ko, C.H. et al; "TRK1 and TRK2 encode structurally related $K^+$ transporters in Saccharomyces cerevisiae" Mol. Cell. Biol.; 1991; pp. 4266-4273; vol. 11; American Society for Microbiology.

Kubo, Y. et al; "Primary structure and functional expression of a rat G-protein-coupled muscarinic potassium channel"; Nature; Aug. 26, 1993; pp. 802-806; vol. 364.

Ludwig, A. et al; "Two pacemaker channels from human heart with profoundly different activation kinetics"; EMBO Journal; 1999; pp. 2323-2329; vol. 18.

Madrid, R. et al; "Ectopic potassium uptake in trk1 trk2 mutants of Saccharomyces cerevisiae correlates with a highly hyperpolarized membrane potential"; J. Biol. Chem; 1998; pp. 14838-14844; vol. 273; The American Society for Biochemistry and Molecular Biology, Inc., United States.

Main, M.J. et al; "The CGRP receptor can couple via pertussis toxin sensitive and insensitive G proteins"; FEBS Lett.; 1998; pp. 6-10; vol. 441; Federation of European Biochemical Societies.

Mumberg, D. et al; "Yeast vectors for the controlled expression of heterologus proteins in different genetic backgrounds"; Gene; 1995; pp. 119-122; vol. 156.

Myers, A.M. et al; "Mitochondrial proteins synthesis is required for maintenance of intact mitochodrial genomes in Saccharomyces cerevisiae"; EMBO Jour.; 1985; pp. 2087-2092; vol. 4; IRL Press Limited, Oxford England.

Nakamura, R.L. et al; "Determination of key structural requirements of a $K^+$ channel pore"; J. Biol. Chem. 1997; pp. 1011-1018; vol. 272; The American Society for Biochemistry and Molecular Biology, Inc.

Roberds, S.L. et al; "Cloning and tissue-specific expression of five voltage-gated potassium channel cDNAs expressed in rat heart"; Proc. Natl. Acad. Sci. U.S.A.; 1991; pp. 1798-1802; vol. 88.

Ronicke, V. et al; "Use of conditional promoters for expression of heterologus proteins in Saccharomyces cerevisiae"; Methods Enzymol.; 1997; pp. 313-322; vol. 283.

Sanguinetti, M. C. et al; "Molecular pysiology of cardiac delayed rectifier $K^+$ channels" Heart Vessels; 1997; pp. 170-172; vol. 12; Springer-Verlag 1997.

Schreibmayer, W. et al; "Inhibition of an inwardly rectifying $K^+$ channel by G-protein alpha-subunits"; Nature; 1996; pp. 654-627; vol. 380.

Smith, F. W. et al; "Plant members of a family of sulfate transporters reveal functional subtypes"; Proc. Natl. Acad. Sci. U.S.A.; 1995; pp. 9373-9377; vol. 92.

Snyders, D.J. et al; "A rapidly activating and slowly inactivating potassium channel cloned from human heart. Functional analysis after stable mammalian cell culture expression"; J. Gen Physiol.; 1993; pp. 513-543; vol. 101.

Taglialatela, M. et al; Human ether-a-gogo related Gene (HERG) $K^+$ channels as pharmacological targets; present and future implications.; Biochem. Pharmacol.; 1998; pp. 1741-1746; vol. 55.

Tang, W. et al; "Functional expression of a vertebrate inwardly rectifying $K^+$ channel in yeast"; Mol. Biol. Cell; 1995; pp. 1231-1240; vol. 6; The American Society for Cell Biology.

Wach, A. et al; "New heterologous modules for classical or PCR-based gene disruptions in Saccharomyces cerevisiae"; Yeast; 1994; pp. 1793-1808; vol. 10; John Wiley & Sons Ltd.

Wang, Q. et al; "Genetics, molecular mechanisms and management of long QT syndrome"; Ann. Med.; 1998; pp. 58-65; vol. 30; The Finnish Medical Society Duodecim.

Wilde, A.A. et al; "Ion channels, the QT interval, and arrhythmias"; Pacing. Clin. Electrophysiol.; 1997; pp. 2048-2051; vol. 20.

Wischmeyer, E. et al; "Subunit interactions in the assembly of neuronal Kir3.0 inwardly rectifying $K^+$ channels"; Mol. Cell. Neurosci.; 1997; pp. 194-206; Vol. 9; Academic Press.

Yamada, M. et al; "G Protein regulation of potassium ion channels"; Pharmacol. Rev.; 1998; pp. 723-760; vol. 50; The American Society for Pharmacology and Experimental Therapeutics; United States.

Bock, J.H. et al; "Nucleotide sequence analysis of the human KCNJ1 potassium channel locus"; Gene; 1997; pp. 9-16; vol. 188; Elsevier Science B.V.

Delpon, E. et al; "Blockade of cardiac potassium and other channels by antihistamines"; Drug Safety; 1999; pp. 11-18; vol. 1; Adis International Limited.

Drici, M.D. et al; "Cardiac $K^+$ channels and drug-acquired long QT syndrome" Therapie; 2000; pp. 185-193; vol. 55.

DuBuske, L. M. "Second-generation antihistamines: the risk of ventricular arrhythmias"; Clin. Ther.; 1999; pp. 281-295; vol. 21.

Itoh, T. et al; "Genomic organization and mutational analysis of KVLQT1, a gene responsible for familial long QT syndrome"; Hum. Genet.; 1998; pp. 290-294; vol. 103; Springer-Verlag 1998.

Kobayashi, T. et al; "Inhibition by various antipsychotic drugs of the G-protein-activated inwardly rectifying K(+) (GIRK) channels expressed in xenopus oocytes"; Br. J. Pharmacol; 2000; pp. 1716-1722; vol. 129; Macmillian Publishers Ltd.

Richelson, E. "Preclinical pharmacology of neuroleptics: focus on new generation compounds"; J. Clin. Psychiatry; 1996; pp. 4-11; vol. 57; Suppl. 11.

Richelson, E. ; "Receptor pharmacology of neuroleptics: relation to clinical effects"; J. Clin. Psychiatry; 1999; pp. 5-14; vol. 60; Suppl. 10.

Shuck, M.E. et al; "Cloning and characterization of multiple forms of the human kidney ROM-K potassium channel"; J. Biol. Chem.: 1994; pp. 24261-24270; vol. 269; The American Society for Biochemistry and Molecular Biology, Inc.; United States.

Taglialatela, M. et al; "Cardiac ion channels and antihistamines: possible mechnaisms of cardiotoxicity"; Clin. Exp. Allergy; 1999; pp. 182-189; vol. 29; Suppl. 3; Blackwell Science Ltd.

\* cited by examiner

SEQUENCE LISTING

<160> NUMBER OF SEQ ID NOS: 31

<210> SEQ ID NO 1
<211> LENGTH: 3708
<212> TYPE: DNA
<213> ORGANISM: Saccharomyces cerevisiae

<400> SEQUENCE: 1
atgcatttta gaagaacgat gagtagagtg cccacattgg catctcttga aatacgatat      60

```
aaaaaatctt tcggccataa atttcgtgat tttattgctc tatgtggtca ctattttgct      120
ccagttaaaa aatatatctt ccccagtttt atcgcggttc actacttcta cacgatatcc      180
ctgacattaa taacttcaat cctgctatat cccattaaga ataccagata cattgataca      240
ttgtttttag cagcgggcgc agttacacaa ggtggcttaa atactgtgga tatcaacaat      300
ctaagcttat accaacaaat tgttctgtat atcgtatgct gcatatcaac accaattgca      360
gttcatagtt gcttggcatt tgtacggctt tactggtttg agcgctactt cgatggtatt      420
agagactctt ctagacgaaa ttttaagatg agaagaacga aaacaatctt agaaagggaa      480
ctaacagcaa gaaccatgac caagaataga acaggtaccc aaagaacgtc ttatcctagg      540
aaacaagcta aaacagatga tttccaagaa aaattgttca gcggagaaat ggttaataga      600
gatgagcagg actcagttca cagcgaccag aattctcatg acattagtag ggacagcagc      660
aataataata cgaatcacaa tggtagcagt ggcagtttag atgatttcgt taaggaagac      720
gaaacggatg acaatggaga atatcaggag aacaactcct actcgacggt aggtagttcg      780
tctaacacag ttgcagacga aagtttaaat cagaagccca agccaagcag tcttcggttt      840
gatgagccac acagcaaaca aagacccgca agagttccct cagagaaatt tgcaaaaaga      900
aggggttcaa gagatattag cccagccgat atgtatcgat ccattatgat gctacaaggt      960
aagcatgaag caactgctga agatgaaggt cccccttag tcatcgggtc ccctgcggat      1020
ggcacaagat ataaaagtaa tgtcaataag ctaaagaagg ccaccggcat aaatggtaac      1080
aaaatcaaga ttcgagataa gggaaatgaa agtaacactg atcaaaattc cgtgtcaagt      1140
gaagcaaaca gtacggcgag cgtttcggac gaaagctcgt tacacacaaa ttttggtaac      1200
aaagtacctt cattaagaac aaatactcat agatcaaatt cgggcccgat agccattact      1260
gataacgcag aaacagacaa aaagcatggg ccatcaattc aattcgatat aactaaacct      1320
cctagaaaaa tttcaaaaag agtttcaacc ttcgatgatt tgaacccaaa atcttccgtt      1380
ctttatcgaa aaaaagcatc gaagaagtac ctcatgaaac attttcctaa agcgcggcga      1440
atacggcaac aaattaagag aaggctttct actggttcaa ttgagaaaaa cagcagtaac      1500
aatgtttcag atagaaaacc tattactgat atggatgatg atgatgatga cgatgacaac      1560
gacggcgata caacgaaga atactttgct gacaacgaaa gcggcgatga agatgaacga      1620
gtacagcagt ctgaaccaca ttctgattca gaactcaaat cgcaccaaca acagcaagaa      1680
aaacaccaac tgcagcagaa cctgcaccgc atgtataaaa ccaaatcatt tgatgataat      1740
cgttcaagag cagttcctat ggaacgttcc aggaccatcg atatggcaga ggctaaggat      1800
ctaaatgagc tcgcaaggac gcctgatttt caaaaaatgg tctatcaaaa ttggaaagcc      1860
catcatagaa aaaaaccgaa ctttaggaag aggggatgga ataacaagat atttgaacat      1920
ggtccctatg catctgacag cgatcgcaat tatcctgata atagtaatac tggaaacagt      1980
attcttcatt acgcagagtc tattttacat catgatggct ctcataaaaa tggaagcgaa      2040
gaagcctctt ccgactctaa tgagaatatc tattccacga atggaggaag cgaccacaat      2100
ggtcttaaca actatcctac ttacaacgac gatgaagaag gctattatgg tttacatttc      2160
gataccgatt atgacctaga tcctcgtcat gatttatcta aaggcagtgg taaaacgtat      2220
ctatcatggc aaccaactat tggacgtaac tcaaacttcc ttggattaac aagagcccag      2280
aaagatgaat taggtggtgt cgagtacaga gcaatcaaac ttttatgcac catattggtt      2340
gtctactacg ttggatggca tattgttgct tttgttatgt tagtaccttg gattattttg      2400
```

```
aaaaagcatt atagtgaagt tgttagagat gatggtgttt cacctacatg gtggggattt    2460
tggacagcaa tgagtgcatt taatgattta ggtttgacat taactccaaa ttcaatgatg    2520
tcgtttaaca aagctgtata cccattgatc gttatgattt ggtttatcat tatcggaaat    2580
acagggtttc ccatccttct tagatgcatc atttggataa tgtttaaaat ttctcctgat    2640
ttatcacaga tgagagaaag tttaggtttt ctcttagacc atccacgtcg ttgtttcacc    2700
ttgctatttc ctaaggcagc tacatggtgg ctacttttaa cgcttgcagg attgaatata    2760
actgattgga tttttattat tattctagat tttggctcaa cagttgtgaa atcattatcg    2820
aaaggctata gagtccttgt cggcctgttt caatctgtta gcacaagaac tgctggattc    2880
agcgttgtcg atttaagtca actgcatcct tctatccaag tctcctatat gctaatgatg    2940
tatgtctccg tattaccatt ggccatctct attcgacgga caaatgttta cgaggagcaa    3000
tctttaggac tatatggaga tatgggggga gaaccagaag atacggatac tgaagacgat    3060
ggtaacgatg aagatgacga cgaggaaaac gagagtcacg aaggtcaaag tagtcaaaga    3120
agtagttcga acaacaacaa caataacaac aggaaaaaga aaagaaaaa  gaaaactgaa    3180 aatccaaatg aaatatctac aaaatccttt atcggtgccc atttaaggaa acagctttca    3240
tttgacttgt ggtttctatt tttagggtta tttatcattt gcatttgtga aggggacaag    3300
ataaaggacg tacaagaacc aaactttaat atatttgcaa ttcttttga aattgttagc    3360 gcttacggta cagttgggct atcgctaggt tatccggaca ccaaccaatc gttttcaaga    3420
cagtttacta cattatctaa gttggtgatc atagctatgc tgatcagagg caagaataga    3480
ggtctaccat actcactgga tcgtgcaatt atcttgccta gtgatagact tgaacatatt    3540
gaccaccttg agggcatgaa attgaagaga caggctagaa ccaatacaga agacccaatg    3600
acggaacatt tcaagagaag tttcactgat gtgaaacatc gttggggagc tcttaagcgt    3660
aagaccacac attcccgaaa tcctaaaagg agcagcacaa cgctctaa               3708

<210> SEQ ID NO 2
<211> LENGTH: 2669
<212> TYPE: DNA
<213> ORGANISM: Saccharomyces cerevisiae

<400> SEQUENCE: 2
atgccaacag ctaagaggac gtcatccagg gcttcgttgg cactgcccctt ccagttacgg      60 ttggtgcaca agaaatcatg gggccatcgg ctaagagact tcatttccgg gttcttaaaa     120
tcatgcagac ccattgctaa atacgttttc cccaacttca tcgtggtgca ctatatctac     180
ctgatcacgc tgtcgattat cgggtccatt ctgttatatc cgtgcaagaa cacggcgttc     240
atcgatgtgc tatttctggc tgctggagcg tctacacagg gcgggctggc caccaagagc     300
actaacgatt tcaacctgta ccagcagata gtggtgtacg tcattacatt gctgtccacg     360
cctatactta ttcatgggtt tttggccttt gtcaggctgt attggtttga aggtacttc      420 gacaacatta gggatatctc caaacagaat tttaaactaa gaaggaccat gacgttgcaa     480
caaagggaac tatcgggcag cagtggcaat gccgctcgaa gtaggagttt caaggacaac     540
ctgttccgtg ggaagtttgt ttccagagaa gacccacgac aatccgcttc agatgtgccg     600
atggactctc ctgacacgtc cgcattgtcc tcaatctcac cgttgaatgt ttcctcctct     660
aaggaggaat ccagtgacac gcaaagctcg cctccaaact tctcaagtaa gcgccaaccc     720
tcagacgttg acccaagaga catttacaaa tcgataatga tgctacaaaa acaacaagag     780
aagagcaacg caaactccac ggattctttt tcgagcgaga ccaatggacc cgctttcatt     840
```

| | |
|---|---:|
| gtgcaggaac gtcatgagag aagagccccc cactgctcac tgaaacgcca ttctgtcctg | 900 |
| ccatcttctc aggaattgaa caagctagcc cagacgaaaa gtttccagaa attgcttggc | 960 |
| ttgcggagag atgaaggtga ccatgactac tttgacggtg ctcctcacaa atatatggtc | 1020 |
| accaagaaga aaaaaatatc tagaacgcaa tcatgtaaca tcccaacgta tactgcttca | 1080 |
| ccgagtccta aaacctcagg ccaagtagtt gaaaatcata gaaacttggc caagtcggcg | 1140 |
| ccttcatctt ttgttgatga ggagatgagc ttttcaccgc aagagtcttt gaatttacag | 1200 |
| ttccaagcgc acccgcccaa accaaaacga cgtgaaggtg atataggcca cccttcacc | 1260 |
| agaacaatga gcaccaacta tctatcgtgg cagccaacct ttggcagaaa ctccgtcttc | 1320 |
| attggactca caaagcaaca aaggaggaa ctcggcggtg tcgaatatcg tgctttgaga | 1380 |
| ttgctgtgct gcattctcat ggtatactac atcggattca acattttggc gtttgtgacc | 1440 |
| atcgttccat gggcctgtac gaggcaccac tactcagaga ttattagacg aaatggagtt | 1500 |
| tctccaacct ggtgggggtt tttcactgca atgagtgcat tcagcaactt gggtctgtct | 1560 |
| ttgaccgctg attcaatggt ttcctttgat actgcgccgt atccgctgat tttcatgatg | 1620 |
| ttcttcatca tcataggcaa tacaggcttc ccaattatgt tacgatttat catttggatc | 1680 |
| atgttcaaga cctcgagaga cctatctcag tttaaggaaa gtcttgggtt tctcttggat | 1740 |
| catccgcgca ggtgttttac gttgctgttc cccagcggcc ccacatggtg gctgtttaca | 1800 |
| actttagtcg tcttaaacgc tacggattgg attcttttca taattctgga tttcaactcc | 1860 |
| gctgtagtaa ggcaggttgc taaaggttat cgagctctca tgggcctctt ccagtctgta | 1920 |
| tgcacaagaa ctgctggatt caacgttgtt gacttaagta aattacaccc gtccattcag | 1980 |
| gtgtcttata tgctaatgat gtacgtttcg gtcctgccgc tggcgatttc cattagaaga | 2040 |
| acgaatgttt atgaggagca atcgttggga ctatacgata gtggacaaga tgacgaaaat | 2100 |
| atcacccacg aagacgatat aaaggaaaca gaccatgatg cgaatccga agagcgagac | 2160 |
| actgtatcta caaagtccaa gccgaagaaa cagtccccaa aatcgtttgt tggtgctcat | 2220 |
| ttgaggaggc aactctcttt tgatttatgg tacctattcc ttggattatt tataatatgc | 2280 |
| atatgcgagg gcagaaaaat cgaagacgtt aataaacctg atttcaatgt ctttgctata | 2340 |
| ttgtttgaag ttgttagcgc ttatggtaca gtgggtttgt cattgggtta cccaaacacc | 2400 |
| aacacatcac tatctgccca gttcaccgta ttatcgaagc tagtcataat tgccatgcta | 2460 |
| ataagaggaa gaaatagagg tttaccatac actttggatc gtgccatcat gctgccaagt | 2520 |
| gacaaactgg aacaaattga tcgtttacaa gatatgaaag ctaagggtaa gttgttagcc | 2580 |
| aaagttggtg aggatccaat gactacttac gtcaaaaaga gatcccacaa actgaaaaaa | 2640 |
| atagcaacaa agttttgggg gaagcatta | 2669 |

<210> SEQ ID NO 3
<211> LENGTH: 2076
<212> TYPE: DNA
<213> ORGANISM: Saccharomyces cerevisiae

<400> SEQUENCE: 3

| | |
|---|---:|
| atgacaaggt tcatgaacag ctttgccaaa caaacgctgg atatggcaa tatggcgaca | 60 |
| gtggagcaag agagctcagc tcaggctgtt gattctcatt caaacaacac accgaagcaa | 120 |
| gctaagggtg ttcttgcaga ggaactaaag gatgcattgc ggttccggga cgaaagagtt | 180 |
| agtattatta atgcagagcc ttcttcaaca ctgttcgtct tttggtttgt ggtttcatgc | 240 |

```
tatttccctg tgattactgc ctgcttgggt cccgtagcta acactatctc gatagcctgt      300
gtagttgaaa aatggagatc cttaaagaac aactccgtgg tgacaaatcc acgaagcaat      360
gacaccgatg ttttgatgaa tcaagtaaag acagttttg atcctcctgg tattttgcc       420 gttaatatca tctctttggt actgggtttt acgtcaaata ttatactaat gctacatttc      480
agtaagaagt tgacgtatct taaatctcag ttaataaata taacaggatg gacaatagct      540
ggagggatgc ttttggtgga cgtgattgta tgctccttga tgacatgcc cagcatctac       600 agtaagacta tcggattttg gtttgcctgt atcagttctg gtctatattt ggtatgcacc      660
attattttaa caatacattt tattggatat aaattaggaa aatatcctcc aacgttcaac      720
cttttgccca tgaaagaag tatcatggca tacactgtac tattgtcttt atggttgatt       780
tggggtgcgg gtatgtttag cggtttattg cacatcactt acggaaatgc attatatttc      840
tgcacggtat cattattaac cgtgggacta ggtgacatcc tgcccaagtc ggttggcgcc      900
aaaatcatgg ttttaatctt ttcgctatct ggtgttgtct tgatgggttt aatagtgttt      960
atgacaagat ccatcattca aaagtcctct ggcccaattt tcttttcca cagagttgaa      1020 aaaggcaggt ccaaatcgtg gaaacattat atggatagta gtaaaaattt atctgaaagg      1080
gaagcgttcg acttaatgaa gtgtatccga caaacggcct caaggaagca gcattggttt      1140
tctttgtcgg tgactattgc aattttcatg gcttttggt tattgggagc tcttgtattc       1200
aaattcgcag aaaattggtc gtacttcaat tgtatttact tttgtttctt gtgcttatta      1260
accattggat acggagacta tgctccaagg actggtgcag gccgtgcttt ttttgtgatt      1320
tgggcgttgg gagccgtgcc attaatgggg gctatcctat ctacagtcgg tgatctgttg      1380
tttgacattt ccacttctct ggatattaag atcggtgaat cattcaataa taaagtcaag      1440
tccatcgttt ttaatgggcg tcaaagagca ctttccttta tggtgaacac tggagaaatt      1500
ttcgaagaat ctgacacagc tgatggtgat ctggaagaaa atacaacgag ctcacaatcc      1560
agtcaaattt ctgaattcaa cgataataat tcagaagaga atgattctgg agtgacatcc      1620
cctcctgcaa gcctgcaaga atcatttttct tcattatcaa aagcatctag cccagaggga      1680
atacttcctc tagaatatgt ttcttctgct gaatatgcac tacaggactc ggggacctgt      1740
aatttaagga acttgcaaga gctacttaaa gccgtcaaaa aactcatcg gatatgtctg       1800 gcggataaag attacacact tagtttttcc gactggtcgt acattcataa actacatttg      1860
aggaacatta cagatattga ggagtacaca cgcggacccg aattttggat atcacctgat      1920
acgcccctca gttcccgtt aaatgaacct cattttgctt ttatgatgct tttcaagaac       1980
atagaagaat tagttggtaa tctagtagaa gacgaagagc tttataaagt tataagcaaa      2040
agaaaatttt tgggtgagca tagaaagaca ctttga                               2076

<210> SEQ ID NO 4
<211> LENGTH: 3479
<212> TYPE: DNA
<213> ORGANISM: Homo sapiens

<400> SEQUENCE: 4
atgccggtgc ggaggggcca cgtcgcgccg cagaacacct tcctggacac catcatccgc      60
aagtttgagg ccagagccg taagttcatc atcgccaacg ctcgggtgga gaactgcgcc      120
gtcatctact gcaacgacgg cttctgcgag ctgtgcggct actcgcgggc cgaggtgatg      180
cagcgaccct gcacctgcga cttcctgcac gggccgcgca cgcagcgccg cgctgccgcg      240
cagatcgcgc aggcactgct gggcgccgag gagcgcaaag tggaaatcgc cttctaccgg      300
```

-continued

```
aaagatggga gctgcttcct atgtctggtg gatgtggtgc ccgtgaagaa cgaggatggg      360
gctgtcatca tgttcatcct caatttcgag gtggtgatgg agaaggacat ggtggggtcc      420
ccggctcatg acaccaacca ccggggcccc cccaccagct ggctggcccc aggccgcgcc      480
aagaccttcc gcctgaagct gcccgcgctg ctggcgctga cggcccggga gtcgtcggtg      540
cggtcgggcg gcgcgggcgg cgcgggcgcc ccggggccg tggtggtgga cgtggacctg       600
acgcccgcgg cacccagcag cgagtcgctg gccctggacg aagtgacagc catggacaac      660
cacgtggcag ggctcgggcc cgcggaggag cggcgtgcgc tggtgggtcc cggctctccg      720
ccccgcagcg cgcccggcca gctcccatcg ccccgggcgc acagcctcaa ccccgacgcc      780
tcgggctcca gctgcagcct ggcccggacg cgctcccgag aaagctgcgc cagcgtgcgc      840
cgcgcctcgt cggccgacga catcgaggcc atgcgcgccg gggtgctgcc cccgccaccg      900
cgccacgcca gaccggggc catgcaccca ctgcgcagcg gcttgctcaa ctccaccctcg      960
gactccgacc tcgtgcgcta ccgcaccatt agcaagattc cccaaatcac cctcaacttt    1020
gtggacctca agggcgaccc cttcttggct tcgcccacca gtgaccgtga gatcatagca    1080
cctaagataa aggagcgaac ccacaatgtc actgagaagg tcacccaggt cctgtccctg    1140
ggcgccgacg tgctgcctga gtacaagctg caggcaccgc gcatccaccg ctggaccatc    1200
ctgcattaca gccccttcaa ggccgtgtgg gactggctca cctgctgct ggtcatctac     1260
acggctgtct tcacacccta ctcggctgcc ttcctgctga aggagacgga agaaggcccg    1320
cctgctaccg agtgtggcta cgcctgccag ccgctggctg tggtgaccct catcgtggac    1380
atcatgttca ttgtggacat cctcatcaac ttccgcacca cctacgtcaa tgccaacgag    1440
gaggtggtca gccaccccgg ccgcatcgcc gtccactact tcaagggctg gttcctcatc    1500
gacatggtgg ccgccatccc cttcgacctg ctcatcttcg gctctggctc tgaggagctg    1560
atcgggctgc tgaagactgc gcggctgctg cggctggtgc gcgtgcgcg gaagctggat    1620
cgctactcag agtacggcgc ggccgtgctg ttcttgctca tgtgcacctt tgcgctcatc    1680
gcgcactggc tagcctgcat ctggtacgcc atcggcaaca tggagcagcc acacatggac    1740
tcacgcatcg gctggctgca caacctgggc gaccagatag gcaaacccta caacagcagc    1800
ggcctggggcg gcccctccat caaggacaag tatgtgacgg cgctctactt caccttcagc    1860
agcctcacca gtgtgggctt cggcaacgtc tctcccaaca ccaactcaga gaagatcttc    1920
tccatctgcg tcatgctcat ggctccctc atgtatgcta gcatcttcgg caacgtgtcg    1980
gccatcatcc agcggctgta ctcgggcaca gcccgctacc acacacagat gctgcgggtg    2040
cgggagttca tccgcttcca ccagatcccc aatcccctgc gccagcgcct cgaggagtac    2100
ttccagcacg cctggtccta caccaacggc atcgacatga acgcggtgct gaagggcttc    2160
cctgagtgcc tgcaggctga catctgcctg cacctgaacc gctcactgct gcagcactgc    2220
aaacccttcc gagggccac caagggctgc cttcggccc tggccatgaa gttcaagacc     2280
acacatgcac cgccagggga cacactggtg catgctgggg acctgctcac cgccctgtac    2340
ttcatctccc ggggctccat cgagatcctg cggggcgacg tcgtcgtggc catcctgggg    2400
aagaatgaca tctttgggga gcctctgaac ctgtatgcaa ggcctggcaa gtcgaacggg    2460
gatgtgcggg ccctcaccta ctgtgaccta cacaagatcc atcgggacga cctgctggag    2520
gtgctggaca tgtaccctga gttctccgac cacttctggt ccagcctgga gatcaccttc    2580
aacctgcgag ataccaacat gatcccgggc tcccccggca gtacggagtt agagggtggc    2640
```

-continued

```
ttcagtcggc aacgcaagcg caagttgtcc ttccgcaggc gcacggacaa ggacacggag    2700
cagccagggg aggtgtcggc cttgggccgg ggccgggcgg gggcagggcc gagtagccgg    2760
ggccggccgg gggggccgtg gggggagagc ccgtccagtg gcccctccag ccctgagagc    2820
agtgaggatg agggcccagg ccgcagctcc agcccctcc gcctggtgcc cttctccagc     2880
cccaggcccc ccggagagcc gccgggtggg gagcccctga tggaggactg cgagaagagc    2940
agcgacactt gcaaccccct gtcaggcgcc ttctcaggag tgtccaacat tttcagcttc    3000 tgggggaca gtcggggccg ccagtaccag gagctccctc gatgccccgc ccccaccccc     3060
agcctcctca acatcccct ctccagcccg gtcggcggc cccggggcga cgtggagagc      3120
aggctggatg ccctccagcg ccagctcaac aggctggaga cccggctgag tgcagacatg    3180
gccactgtcc tgcagctgct acagaggcag atgacgctgg tcccgcccgc ctacagtgct    3240
gtgaccaccc cggggcctgg ccccacttcc acatccccgc tgttgcccgt cagccccctc    3300
cccaccctca ccttggactc gctttctcag gtttcccagt tcatggcgtg tgaggagctg    3360 ccccgggg ccccagagct tccccaagaa ggccccacac gacgcctctc cctaccgggc     3420
cagctggggg ccctcacctc ccagcccctg cacagacacg gctcggaccc gggcagtta    3479
```

<210> SEQ ID NO 5
<211> LENGTH: 1836
<212> TYPE: DNA
<213> ORGANISM: Homo sapiens

<400> SEQUENCE: 5

```
atggagatcg ccctggtgcc cctggagaac ggcggtgcca tgaccgtcag aggaggcgat     60
gaggcccggg caggctgcgg ccaggccaca ggggagagc tccagtgtcc cccgacggct     120
gggctcagcg atgggcccaa ggagccggcg ccaaagggc gcgcagag agacgcggac       180 tcggagtgc ggcccttgcc tccgctgccg acccgggag tgcggccctt gcctccgctg       240
ccagaggagc tgccacggcc tcgacggccg cctcccgagg acgaggagga agaaggcgat    300
cccggcctgg gcacggtgga ggaccaggct ctgggcacgg cgtccctgca ccaccagcgc    360
gtccacatca acatctccgg gctgcgcttt gagacgcagc tgggcaccct ggcgcagttc    420
cccaacacac tcctggggga ccccgccaag cgcctgccgt acttcgaccc cctgaggaac    480
gagtacttct tcgaccgcaa ccggcccagc ttcgacggta tcctctacta ctaccagtcc    540 ggggccgcc tgcagggggt caacgtctcc ctggacgtgt cgcggacga gatacgcttc     600 taccagctgg gggacgaggc catggagcgc ttccgcgagg atgagggctt cattaaagaa    660
gaggagaagc ccctgccccg caacgagttc cagcgccagg tgtggcttat cttcgagtat    720
ccggagagct ctgggtccgc gcgggccatc gccatcgtct cggtcttggt tatcctcatc    780
tccatcatca ccttctgctt ggagaccctg cctgagttca gggatgaacg tgagctgctc    840
cgccaccctc cggcgcccca ccagcctccc gcgcccgccc ctggggccaa cggcagcggg    900
gtcatggccc ccgcctctgg ccctacggtg gcaccgctcc tgcccaggac cctggccgac    960
cccttcttca tcgtggagac cacgtgcgtg atctggttca ccttcgagct gctcgtcgcg    1020
ttcttcgcct gccccagcaa ggcagggttc tcccggaaca tcatgaacat catcgatgtg    1080
gtggccatct ccctacttt catcaccctg gcaccgaac tggcagagca gcagccaggg    1140 ggcgaggag gcggccagaa tggcagcag gccatgtccc tggccatcct ccgagtcatc    1200
cgcctggtcc gggtgttccg catcttcaag ctctcccgcc actccaaggg gctgcagatc    1260
ctgggcaaga ccttgcaggc ctccatgagg gagctggggc tgctcatctt cttcctcttc    1320
```

```
atcggggtca tcctcttctc cagtgccgtc tacttcgcag aggctgacaa ccagggaacc    1380
catttctcta gcatccctga cgccttctgg tgggcagtgg tcaccatgac cactgtgggc    1440
tacggggaca tgaggcccat cactgttggg ggcaagatcg tgggctcgct gtgtgccatc    1500
gccggggtcc tcaccattgc cctgcctgtg cccgtcatcg tctccaactt caactacttc    1560
taccaccggg aaacggatca cgaggagccg gcagtcctta aggaagagca gggcactcag    1620
agccaggggc cggggctgga cagaggagtc cagcggaagg tcagcgggag caggggatcc    1680
ttctgcaagg ctgggggggac cctggagaat gcagacagtg cccgaagggg cagctgcccc    1740
ctagagaagt gtaacgtcaa ggccaagagc aacgtggact gcgcgaggtc cctttatgcc    1800
ctctgcctgg acaccagccg ggaaacagat ttgtga                              1836
```

<210> SEQ ID NO 6
<211> LENGTH: 1284
<212> TYPE: DNA
<213> ORGANISM: Cavia guianae

<400> SEQUENCE: 6

```
atgggcagtg tgcgaaccaa ccgctatagc attgtctctt cggaagagga cggcatgaag      60
ttggccacca tggcagttgc caatggcttt gggaatggga aaagtaaagt ccacactcgg     120
caacagtgta ggagccgctt gtgaagaaaa gatggccact gtaatgttca gttcatcaac     180
gttgggaaaa agggacaacg gtaccttgct gacattttta ctacgtgtgt ggacattcgc     240
tggcggtgga tgctggttat cttttgccta gcttttgttc tctcgtggct gttttttggc     300
tgtgtgtttt ggctgatagc tttgctccat ggagatctgg atgcatctaa ggagagcaaa     360
gcctgtgtgt ctgaggtcaa cagcttcaca gctgcctttc ttttctccat tgagacccag     420
acaaccatcg gctatgggtt ccgatgtgtc acggatgaat gcccgattgc ggtgttcatg     480
gttgtgttcc agtcaattgt gggctgcatt attgatgctt tatcattggt gccgtcatg     540 gcaaagatgg caaagccaaa gaaaagaaat gagactcttg tcttcagtca caatgctgtg     600
attgccatga gagatggcaa gctgtgtttg atgtggcgag taggcaacct tcggaaaagc     660
cacttggtag aagctcatgt tcgagcccag ctcctcaaat ccagaattac ttctgaaggg     720
gaatacatcc ccttggatca aatagacatc aatgttggct ttgacagtgg aattgaccgt     780
atatttctgg tatccccaat cactattgtc catgaaatag atgaagatag tcctttatat     840
gatttgagca gcaggacat tgataatgca gactttgaaa ttgttgtgat actagaaggc     900
atggtggaag ccactgccat gacaacacag tgtcgtagtt cttatttggc caacgagatc     960
ctttggggcc accgctatga gccagtgctc tttgaggaga gcactacta taaagtggac    1020 tattcgaggt tcataagac ttacgaagta cccaacactc ccctttgtag tgccagagac    1080
ttagcagaaa agaaatatat tctctcaaat gctaactcat tttgctatga aaatgaagtt    1140
gcccttacaa gcaaagagga agatgacagt gaaaatgggg ttccagaaag caccagtaca    1200
gacacacctc ctgacatcga ccttcacaac caggcaagtg tacctctaga gcccagaccc    1260
ttacggcgag aatcggagat atga                                           1284
```

<210> SEQ ID NO 7
<211> LENGTH: 34
<212> TYPE: DNA
<213> ORGANISM: Artificial Sequence
<220> FEATURE:
<223> OTHER INFORMATION: Primer

```
<400> SEQUENCE: 7
gcggatccat gcattttaga agaacgatga gtag                              34

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
aggttctgct gcagttggtg t                                            21

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
acaccaactg cagcagaacc t                                            21

<210> SEQ ID NO 10
<211> LENGTH: 29
<212> TYPE: DNA
<213> ORGANISM: Artificial Sequence
<220> FEATURE:
<223> OTHER INFORMATION: Primer

<400> SEQUENCE: 10
cgctcgagtt agagcgttgt gctgctcct                                    29

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
ccttaccatt agcatcactg at                                           22

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
ctattaacca tttctccgct g                                            21

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
gatttatctt cgtttcctgc aggt                                         24

<210> SEQ ID NO 14
<211> LENGTH: 31
```

<212> TYPE: DNA
<213> ORGANISM: Artificial Sequence
<220> FEATURE:
<223> OTHER INFORMATION: Primer

<400> SEQUENCE: 14
cacgtacgtc cagcacaatt tcacaacagc t                              31

<210> SEQ ID NO 15
<211> LENGTH: 30
<212> TYPE: DNA
<213> ORGANISM: Artificial Sequence
<220> FEATURE:
<223> OTHER INFORMATION: Primer

<400> SEQUENCE: 15
cagtcgacct ggatgacgtc ctcttagctg                                30

<210> SEQ ID NO 16
<211> LENGTH: 29
<212> TYPE: DNA
<213> ORGANISM: Artificial Sequence
<220> FEATURE:
<223> OTHER INFORMATION: Primer

<400> SEQUENCE: 16
cagatatcat gctgccaagt gacaaactg                                 29

<210> SEQ ID NO 17
<211> LENGTH: 28
<212> TYPE: DNA
<213> ORGANISM: Artificial Sequence
<220> FEATURE:
<223> OTHER INFORMATION: Primer

<400> SEQUENCE: 17
tcactagttg ttgatggctt tggttggt                                  28

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
gcgaagaata ggatgagatg tg                                        22

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
ttgtcgtggg tcttctctgg                                           20

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20

```
gctacctttg ccatgtttca gaa                                              23
```

<210> SEQ ID NO 21
<211> LENGTH: 31
<212> TYPE: DNA
<213> ORGANISM: Artificial Sequence
<220> FEATURE:
<223> OTHER INFORMATION: Primer

<400> SEQUENCE: 21

```
cacgtacggc aaatttatcg agactctgcg a                                     31
```

<210> SEQ ID NO 22
<211> LENGTH: 29
<212> TYPE: DNA
<213> ORGANISM: Artificial Sequence
<220> FEATURE:
<223> OTHER INFORMATION: Primer

<400> SEQUENCE: 22

```
aggtcgacca tattgccata tcccagcgt                                        29
```

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23

```
tggatatcac ctgatacgcc c                                                21
```

<210> SEQ ID NO 24
<211> LENGTH: 35
<212> TYPE: DNA
<213> ORGANISM: Artificial Sequence
<220> FEATURE:
<223> OTHER INFORMATION: Primer

<400> SEQUENCE: 24

```
caactagtgc ataccagtag tatgagacat gcttg                                 35
```

<210> SEQ ID NO 25
<211> LENGTH: 23
<212> TYPE: DNA
<213> ORGANISM: Artificial Sequence
<220> FEATURE:
<223> OTHER INFORMATION: Primer

<400> SEQUENCE: 25

```
cctgagtact cagtaccatc ttg                                              23
```

<210> SEQ ID NO 26
<211> LENGTH: 18
<212> TYPE: DNA
<213> ORGANISM: Artificial Sequence
<220> FEATURE:
<223> OTHER INFORMATION: Primer

<400> SEQUENCE: 26

```
ctgtagatgc tgggcatg                                                    18
```

<210> SEQ ID NO 27
<211> LENGTH: 27
<212> TYPE: DNA
<213> ORGANISM: Artificial Sequence

```
<220> FEATURE:
<223> OTHER INFORMATION: Primer

<400> SEQUENCE: 27
tacgtcgaca tggagatcgc cctggtg                                           27

<210> SEQ ID NO 28
<211> LENGTH: 28
<212> TYPE: DNA
<213> ORGANISM: Artificial Sequence
<220> FEATURE:
<223> OTHER INFORMATION: Primer

<400> SEQUENCE: 28
tacgtcgaca tctgtttccc ggctggtg                                          28

<210> SEQ ID NO 29
<211> LENGTH: 25
<212> TYPE: DNA
<213> ORGANISM: Artificial Sequence
<220> FEATURE:
<223> OTHER INFORMATION: Primer

<400> SEQUENCE: 29
tacatcgata tgccggtgcg gaggg                                             25

<210> SEQ ID NO 30
<211> LENGTH: 24
<212> TYPE: DNA
<213> ORGANISM: Artificial Sequence
<220> FEATURE:
<223> OTHER INFORMATION: Primer

<400> SEQUENCE: 30
tacgtcgaca ctgcccgggt ccga                                              24

<210> SEQ ID NO 31
<211> LENGTH: 7772
<212> TYPE: DNA
<213> ORGANISM: Homo sapiens

<400> SEQUENCE: 31
gacgaaaggg cctcgtgata cgcctatttt tataggttaa tgtcatgata ataatggttt        60
cttagatgat ccaatatcaa aggaaatgat agcattgaag gatgagacta atccaattga       120
ggagtggcag catatagaac agctaaaggg tagtgctgaa ggaagcatac gatacccgc        180 atggaatggg ataatatcac aggaggtact agactacctt tcatcctaca taaatagacg       240
catataagta cgcatttaag cataaacacg cactatgccg ttcttctcat gtatatatat       300
atacaggcaa cacgcagata taggtgcgac gtgaacagtg agctgtatgt gcgcagctcg       360
cgttgcattt tcggaagcgc tcgttttcgg aaacgctttg aagttcctat tccgaagttc       420
ctattctcta gaaagtatag gaacttcaga gcgcttttga aaaccaaaag cgctctgaag       480
acgcactttc aaaaaaccaa aaacgcaccg gactgtaacg agctactaaa atattgcgaa       540
taccgcttcc acaaacattg ctcaaaagta tctctttgct atatatctct gtgctatatc       600
cctatataac ctaccatcc  acctttcgct ccttgaactt gcatctaaac tcgacctcta       660
cattttttat gtttatctct agtattactc tttagacaaa aaaattgtag taagaactat       720
tcatagagtg aatcgaaaac aatacgaaaa tgtaaacatt tcctatacgt agtatataga       780
gacaaaatag aagaaaccgt tcataatttt ctgaccaatg aagaatcatc aacgctatca       840
```

```
ctttctgttc acaaagtatg cgcaatccac atcggtatag aatataatcg gggatgcctt    900
tatcttgaaa aaatgcaccc gcagcttcgc tagtaatcag taaacgcggg aagtggagtc    960
aggcttttt  tatggaagag aaaatagaca ccaaagtagc cttcttctaa ccttaacgga   1020
cctacagtgc aaaaagttat caagagactg cattatagag cgcacaaagg agaaaaaaag   1080
taatctaaga tgctttgtta gaaaatagc gctctcggga tgcatttttg tagaacaaaa   1140
aagaagtata gattctttgt tggtaaaata gcgctctcgc gttgcatttc tgttctgtaa   1200
aaatgcagct cagattcttt gtttgaaaaa ttagcgctct cgcgttgcat ttttgtttta   1260
caaaaatgaa gcacagattc ttcgttggta aaatagcgct ttcgcgttgc atttctgttc   1320
tgtaaaaatg cagctcagat tctttgtttg aaaaattagc gctctcgcgt tgcattttg    1380
ttctacaaaa tgaagcacag atgcttcgtt caggtggcac ttttcgggga aatgtgcgcg   1440
gaacccctat ttgtttattt ttctaaatac attcaaatat gtatccgctc atgagacaat   1500
aaccctgata aatgcttcaa taatattgaa aaggaagag tatgagtatt caacatttcc   1560
gtgtcgccct tattcccttt tttgcggcat tttgccttcc tgttttgct cacccagaaa    1620
cgctggtgaa agtaaaagat gctgaagatc agttgggtgc acgagtgggt tacatcgaac   1680
tggatctcaa cagcggtaag atccttgaga gttttcgccc cgaagaacgt tttccaatga   1740
tgagcacttt taaagttctg ctatgtggcg cggtattatc ccgtattgac gccgggcaag   1800
agcaactcgg tcgccgcata cactattctc agaatgactt ggttgagtac tcaccagtca   1860
cagaaaagca tcttacggat ggcatgacag taagagaatt atgcagtgct gccataacca   1920
tgagtgataa cactgcggcc aacttacttc tgacaacgat cggaggaccg aaggagctaa   1980
ccgcttttt  gcacaacatg ggggatcatg taactcgcct tgatcgttgg gaaccggagc   2040
tgaatgaagc cataccaaac gacgagcgtg acaccacgat gcctgtagca atggcaacaa   2100
cgttgcgcaa actattaact ggcgaactac ttactctagc ttcccggcaa caattaatag   2160
actggatgga ggcggataaa gttgcaggac cacttctgcg ctcggccctt ccggctggct   2220
ggtttattgc tgataaatct ggagccggtg agcgtgggtc tcgcggtatc attgcagcac   2280
tggggccaga tggtaagccc tcccgtatcg tagttatcta cacgacgggg agtcaggcaa   2340
ctatggatga acgaaataga cagatcgctg agataggtgc ctcactgatt aagcattggt   2400
aactgtcaga ccaagtttac tcatatatac tttagattga tttaaaactt catttttaat   2460
ttaaaaggat ctaggtgaag atcctttttg ataatctcat gaccaaaatc ccttaacgtg   2520
agttttcgtt ccactgagcg tcagaccccg tagaaaagat caaaggatct tcttgagatc   2580
cttttttct  gcgcgtaatc tgctgcttgc aaacaaaaaa accaccgcta ccagcggtgg   2640
tttgtttgcc ggatcaagag ctaccaactc tttttccgaa ggtaactggc ttcagcagag   2700
cgcagatacc aaatactgtc cttctagtgt agccgtagtt aggccaccac ttcaagaact   2760
ctgtagcacc gcctacatac ctcgctctgc taatcctgtt accagtggct gctgccagtg   2820
gcgataagtc gtgtcttacc gggttggact caagacgata gttaccggat aaggcgcagc   2880
ggtcgggctg aacggggggt tcgtgcacac agcccagctt ggagcgaacg acctacaccg   2940
aactgagata cctacagcgt gagctatgag aaagcgccac gcttcccgaa gggagaaagg   3000
cggacaggta tccggtaagc ggcagggtcg gaacaggaga gcgcacgagg gagcttccag   3060
ggggaaacgc ctggtatctt tatagtcctg tcgggtttcg ccacctctga cttgagcgtc   3120
gatttttgtg atgctcgtca ggggggcgga gcctatggaa aaacgccagc aacgcggcct   3180
ttttacggtt cctggccttt tgctggcctt ttgctcacat gttctttcct gcgttatccc   3240
```

```
ctgattctgt ggataaccgt attaccgcct ttgagtgagc tgataccgct cgccgcagcc   3300
gaacgaccga gcgcagcgag tcagtgagcg aggaagcgga agagcgccca atacgcaaac   3360
cgcctctccc cgcgcgttgg ccgattcatt aatgcagctg gcacgacagg tttcccgact   3420
ggaaagcggg cagtgagcgc aacgcaatta atgtgagtta cctcactcat taggcacccc   3480
aggctttaca ctttatgctt ccggctccta tgttgtgtgg aattgtgagc ggataacaat   3540
ttcacacagg aaacagctat gaccatgatt acgccaagcg cgcaattaac cctcactaaa   3600
gggaacaaaa gctggagctc agtttatcat tatcaatact gccatttcaa gaatacgta    3660
aataattaat agtagtgatt ttcctaactt tatttagtca aaaaattagc cttttaattc    3720
tgctgtaacc cgtacatgcc caaaataggg ggcgggttac acagaatata taacatcgta   3780
ggtgtctggg tgaacagttt attcctggca tccactaaat ataatggagc ccgcttttta   3840
agctggcatc cagaaaaaaa aagaatccca gcaccaaaat attgttttct tcaccaacca   3900
tcagttcata ggtccattct cttagcgcaa ctacagagaa caggggcaca aacaggcaaa   3960
aaacgggcac aacctcaatg gagtgatgca acctgcctgg agtaaatgat gacacaaggc   4020
aattgaccca cgcatgtatc tatctcattt tcttacacct tctattacct tctgctctct   4080
ctgatttgga aaaagctgaa aaaaaaggtt gaaaccagtt ccctgaaatt attcccctac    4140
ttgactaata agtatataaa gacggtaggt attgattgta attctgtaaa tctatttctt   4200
aaacttctta aattctactt ttatagttag tcttttttt agttttaaaa caccagaact   4260
tagtttcgac ggattctaga actagtggat cccccgggct gcagccatgt tcaaacatct   4320
tcggaaatgg gtcgtcactc gcttttttgg gcattctcgg caaagagcaa ggctagtctc   4380
caaagatgga aggtgcaaca tagaatttgg caatgtggag gcacagtcaa ggtttatatt   4440
ctttgtggac atctggacaa cggtacttga cctcaagtgg agatacaaaa tgaccatttt   4500
catcacagcc ttcttgggga gttggttttt ctttggtctc ctgtggtatg cagtagcgta   4560
cattcacaaa gacctcccgg aattccatcc ttctgccaat cacactccct gtgtggagaa   4620
tattaatggc ttgacctcag cttttctgtt ttctctggag actcaagtga ccattggata   4680
tggattcagg tgtgtgacag aacagtgtgc cactgccatt tttctgctta tctttcagtc   4740
tatacttgga gttataatca attctttcat gtgtggggcc atcttagcca agatctccag   4800
gcccaaaaaa cgtgccaaga ccattacgtt cagcaagaac gcagtgatca gcaaacgggg   4860
agggaagctt tgcctcctaa tccgagtggc taatctcagg aagagccttc ttattggcag   4920
tcacatttat ggaaagcttc tgaagaccac agtcactcct gaaggagaga ccattatttt   4980
ggaccagatc aatatcaact tgtagttga cgctgggaat gaaaatttat tcttcatctc   5040
cccattgaca atttaccatg tcattgatca caacagccct ttcttccaca tggcagcgga   5100
gacccttctc cagcaggact ttgaattagt ggtgttttta gatggcacag tggagtccac   5160
cagtgctacc tgccaagtcc ggacatccta tgtcccagag gaggtgcttt ggggctaccg   5220
ttttgctccc atagtatcca agacaaagga agggaaatac cgagtggatt ccataacttt   5280
tagcaagaca gtggaagtgg agacccctca ctgtgccatg tgcctttata atgagaaaga   5340
tgttagagcc aggatgaaga gaggctatga caacccaac ttcatcttgt cagaagtcaa   5400
tgaaacagat gacaccaaaa tgtaacagtc gacctcgagt catgtaatta gttatgtcac   5460
gcttacattc acgccctccc cccacatccg ctctaaccga aaaggaagga gttagacaac   5520
ctgaagtcta ggtccctatt tatttttta tagttatgtt agtattaaga acgttattta   5580
```

```
tatttcaaat ttttcttttt tttctgtaca gacgcgtgta cgcatgtaac attatactga   5640
aaaccttgct tgagaaggtt tgggacgct cgaaggcttt aatttgcggc cggtacccaa    5700
ttcgccctat agtgagtcgt attacgcgcg ctcactggcc gtcgttttac aacgtcgtga   5760
ctgggaaaac cctggcgtta cccaacttaa tcgccttgca gcacatcccc ctttcgccag   5820
ctggcgtaat agcgaagagg cccgcaccga tcgcccttcc caacagttgc gcagcctgaa   5880
tggcgaatgg cgcgacgcgc cctgtagcgg cgcattaagc gcggcgggtg tggtggttac   5940
gcgcagcgtg accgctacac ttgccagcgc cctagcgccc gctcctttcg ctttcttccc   6000
ttcctttctc gccacgttcg ccggctttcc ccgtcaagct ctaaatcggg gctcccttt    6060 agggttccga tttagtgctt tacggcacct cgaccccaaa aaacttgatt agggtgatgg   6120
ttcacgtagt gggccatcgc cctgatagac ggttttttcg ccctttgacgt tggagtccac   6180 gttctttaat agtggactct tgttccaaac tggaacaaca ctcaacccta tctcggtcta   6240
ttcttttgat ttataaggga ttttgccgat ttcggcctat tggttaaaaa atgagctgat   6300
ttaacaaaaa tttaacgcga attttaacaa aatattaacg tttacaattt cctgatgcgg   6360
tattttctcc ttacgcatct gtgcggtatt tcacaccgca tagatccgtc gagttcaaga   6420
gaaaaaaaaa gaaaaagcaa aagaaaaaa ggaaagcgcg cctcgttcag aatgacacgt     6480
atagaatgat gcattacctt gtcatcttca gtatcatact gttcgtatac atacttactg   6540
acattcatag gtatacatat atacacatgt atatatatcg tatgctgcag ctttaaataa   6600
tcggtgtcac tacataagaa cacctttggt ggagggaaca tcgttggtac cattgggcga   6660
ggtggcttct cttatggcaa ccgcaagagc cttgaacgca ctctcactac ggtgatgatc   6720
attcttgcct cgcagacaat caacgtggag ggtaattctg ctagcctctg caaagctttc   6780
aagaaaatgc gggatcatct cgcaagagag atctcctact ttctcccttt gcaaaccaag   6840
ttcgacaact gcgtacggcc tgttcgaaag atctaccacc gctctggaaa gtgcctcatc   6900
caaaggcgca atcctgatc caaaccttt tactccacgc gccagtaggg cctctttaaa     6960
agcttgaccg agagcaatcc cgcagtcttc agtggtgtga tggtcgtcta tgtgtaagtc   7020
accaatgcac tcaacgatta gcgaccagcc ggaatgcttg gccagagcat gtatcatatg   7080
gtccagaaac cctatacctg tgtggacgtt aatcacttgc gattgtgtgg cctgttctgc    7140
tactgcttct gcctcttttt ctgggaagat cgagtgctct atcgctaggg gaccaccctt   7200
taaagagatc gcaatctgaa tcttggtttc atttgtaata cgctttacta gggctttctg   7260
ctctgtcatc tttgccttcg tttatcttgc ctgctcattt tttagtatat tcttcgaaga   7320
aatcacatta ctttatataa tgtataattc attatgtgat aatgccaatc gctaagaaaa   7380
aaaaagagtc atccgctagg ggaaaaaaaa aaatgaaaat cattaccgag gcataaaaaa   7440
atatagagtg tactagagga ggccaagagt aatagaaaaa gaaaattgcg ggaaaggact   7500
gtgttatgac ttccctgact aatgccgtgt tcaaacgata cctggcagtg actcctagcg   7560
ctcaccaagc tcttaaaacg ggaatttatg gtgcactctc agtacaatct gctctgatgc   7620
cgcatagtta agccagcccc gacacccgcc aacacccgct gacgcgccct gacgggcttg   7680
tctgctcccg gcatccgctt acagacaagc tgtgaccgtc tccgggagct gcatgtgtca   7740
gaggttttca ccgtcatcac cgaaacgcgc ga                                 7772
```

POTASSIUM CHANNEL MUTANTS OF THE YEAST SACCHAROMYCES CEREVISIAE AND THEIR USE FOR SCREENING EUKARYOTIC POTASSIUM CHANNELS

The invention relates to processes for identifying inhibitors and activators of eukaryotic potassium channels, in which a mutated S. cerevisiae cell is used whose endogenous potassium channels TRK1, TRK2 and TOK1 are not expressed functionally, but which heterologously expresses a eukaryotic potassium channel to be studied. Other subject matters of the invention are mutated S. cerevisiae cells which do not express TRK1, TRK2 and TOK1, and the preparation and use of these mutated S. cerevisiae cells.

Each cell is enclosed by a plasma membrane with a thickness of approximately 6-8 nm. This membrane determines the cell's dimensions and separates the cell content from its environment. All biomembranes are composed of a connected bilayer of lipid molecules, which bilayer accommodates a variety of membrane proteins. While the lipid bilayer determines the basic structure of biomembranes, the proteins are responsible for most of their functions. Owing to its hydrophobic interior, the lipid bilayer acts as an impermeable barrier for most polar molecules. Only membrane proteins such as receptors, ion channels and transporters allow controlled ion flux and the transport of polar molecules (Alberts et al., 1995). Thus, proteins contribute to different ion concentrations in the cell's interior and its environment and govern the entry of nutrients and the exit of breakdown products. Most of the membrane proteins span the plasma membrane repeatedly, as do the ion channels, which thus belong to the group of the integral membrane proteins. These proteins have both hydrophobic regions, which span the lipid bilayer, and hydrophilic sections, which are exposed to the aqueous medium on either side of the membrane. Ion channels are found in all cells and, in nerve cells, are responsible for the generation of action potentials (Alberts et al., 1995). Ion channels can be differentiated on the basis of their different ion selectivity and with reference to their different opening and closing mechanisms.

Potassium channels are ubiquitous membrane proteins found both in excitable and in nonexcitable cells (for review see (Jan, L.Y. et al., 1997). Open potassium channels shift the membrane potential closer to the potassium equilibrium potential and thus away from the threshold potential for triggering an action potential. Thus, potassium channels strengthen the resting membrane potential, repolarizing the cell and in this way determine the length of the frequency of action potentials (Sanguinetti, M. C. et al., 1997; Wilde, A. A. et al., 1997; Wang, Q. et al., 1998). Owing to these functions, potassium channels also constitute the molecular cause for the generation of a number of pathological situations and are thus an interesting target for the development of therapeutical agents.

The yeast Saccharomyces cerevisiae (hereinbelow S. cerevisiae) has three potassium channels, namely TRK1, TRK2 and TOK1. The potassium channel TRK1 (YJL129c) belongs to the family of the "major facilitator" potassium permeases and, being a high-affinity potassium transporter, is responsible for the influx of potassium ions from the medium into the cell (Gaber, R. F. et al., 1988; Ko, C. H. et al., 1990; Ko, C. H. et al., 1991). The deletion mutant Δtrk1 is viable and highly polarized on at least 10 mM $K^+$ (Gaber, R. F. et al., 1988; Madrid, R. et al., 1998). A Δtrk1 strain does not survive on 1 mM $K^+$ (Gaber, R. F. et al., 1988).

The potassium channel TRK2 (YKR050w) also belongs to the family of the "major facilitator" potassium permeases and, being a low-affinity potassium transporter, is responsible for the influx of potassium ions from the medium into the cell (Ko, C. H. et al., 1990; Ko, C. H. et al., 1991; Madrid, R. et al., 1998). The phenotype of the Δtrk2 deletion mutant is less pronounced than in the case of the Δtrk1 mutant. A Δtrk2 strain also survives on 1 mM $K^+$ (Ko, C. H. et al., 1990; Madrid, R. et al., 1998).

The potassium channel TOK1 (also known as DVK1 or YORK) is responsible for the influx of potassium ions from the medium into the cell (Ketchum, K. A. et al., 1995; Fairman, C. et al., 1999). However, the direction of the ion fluxes is reversible, and, depending on the culture conditions, can therefore also take the opposite direction (Fairman, C. et al., 1999).

The deletion mutant Δtrk1 Δtrk2 has already been described repeatedly (Ko, C. H. et al., 1990; Ko, C. H. et al., 1991; Madrid, R. et al., 1998; Fairman, C. et al., 1999).

In the past, this mutant was also used for identifying and describing $K^+$ channels of higher eukaryotes by complementation of the phenotype. Described to date is the complementation by the inward rectifier channels KAT1 cDNA (Arabidopsis thaliana), HKT1 cDNA (Triticum aestivum), IRK1 (Mus musculus) and HKT1 $K^+/Na^+$ transporters (Triticum aestivum) (Tang, W. et al., 1995; Smith, F. W. et al., 1995; Goldstein, S. A. et al., 1996; Nakamura, R. L. et al., 1997). In addition, it has been described that the overexpression of TOK1 and its homologue ORK1 from Drosophila melanogaster in yeast cells can complement the growth deficiency of the Δtrk1 Δtrk2 mutant (Fairman, C. et al., 1999).

However, the study of a large number of eukaryotic potassium channels and the identification of substances which can modify the activity of the potassium channels is difficult since, for example, the human channels HERG1 or Kv1.5 cannot complement the lethal phenotype of Δtrk1 Δtrk2 on 5 mM KCl. Thus, no screening is possible.

The invention relates to a process for identifying inhibitors of a eukaryotic potassium channel, in which
  a) a mutated S. cerevisiae cell is used which does not express the three endogenous potassium channels TRK1, TRK2 and TOK1;
  b) a eukaryotic potassium channel is expressed heterologously in this mutated S. cerevisiae cell;
  c) the mutated S. cerevisiae cell is incubated together with a substance to be tested; and
  d) the effect of the substance to be tested on the eukaryotic potassium channel is determined.

In the mutated S. cerevisiae cell used in the method, the genes TRK1, TRK2 and TOK1 (SEQ ID NO. 1, SEQ ID NO. 2 and SEQ ID NO. 3) are switched off (Δtrk1, Δtrk2, Δtok1), preferably by knock-out, it being preferred for large portions of the genes to be deleted.

The eukaryotic potassium channel used in the process is the potassium channel to be studied, the channel for which inhibitors or activators are to be identified.

For example, the eukaryotic potassium channel is a human HERG1, a human Kv1.5, a human ROMK2 or gpIRK1 (guinea pig) channel. The eukaryotic potassium channel preferably has the natural sequence of the potassium channel in question, for example encoded by one of the sequences SEQ ID NO. 4, SEQ ID. NO. 5, SEQ ID NO. 7 (ROMK2) or SEQ ID NO. 6. However, the natural sequence of the potassium channel can also be modified, for example mutated.

Preferably, the nucleotide sequence encoding the eukaryotic potassium channel is integrated into a yeast expression plasmid, for example p423 GPD3 or a vector, for example of the pRS 42x or pRS 32x series, and the recombinant expression plasmid is introduced into the mutated S. cerevisiae cell.

The process is intended to identify substances which have an effect on the eukaryotic potassium channel. These substances inhibit the growth of the mutated *S. cerevisiae* cell. A substance to be studied which inhibits the heterologously expressed eukaryotic potassium channel causes the mutated *S. cerevisiae* cell—since it does not express endogenous potassium channels—to divide and multiply with greater difficulty or more slowly or, in a particular embodiment of the invention, to die.

The effect of the substance to be tested can be determined for example directly by measuring the optical density at 600 nm or with the aid of a growth reporter which is expressed constitutively in the mutated *S. cerevisiae* cell. The constitutively expressed growth reporter preferably encodes a protein which either shows fluorescence or luminescence itself or which participates in a reaction which gives a fluorescence or luminescence signal. The sequence encoding the growth reporter is preferably of a vector. Suitable growth reporters are, for example, the LacZ gene for β-galactosidase or acid phosphatase PH03, both of which are expressed under the control of a constitutive yeast promoter. The measurable fluorescence or luminescence allows conclusions regarding the cell count of the mutated *S. cerevisiae* cells. If no, or less, fluorescence or luminescence is measured, then the sample in question contains fewer mutated *S. cerevisiae* cells. If fewer mutated *S. cerevisiae* cells are present, then the substance to be tested has an inhibitor effect on the eukaryotic potassium channel.

The processes described can be automated with particular ease and carried out in parallel for a multiplicity of substances to be tested. In particular embodiments of the invention, two or more processes are carried out in a comparative fashion, where two or more mutated *S. cerevisiae* cells are analyzed in a comparative fashion. These mutated *S. cerevisiae* cells are preferably incubated together with the same amount of substance to be tested, but express the eukaryotic potassium channel in question to a different extent. In another particular embodiment of the invention, mutated *S. cerevisiae* cells which express the eukaryotic potassium channel in question to the same extent, but which are incubated together with different amounts of substance to be tested, are analyzed in a comparative fashion.

Subject matter of the invention is also a mutated *S. cerevisiae* cell in which the endogenous potassium channels TRK1, TRK2 and TOK1 are not expressed. A further embodiment relates to a mutated *S. cerevisiae* cell in which the genes TRK1, TRK2 and TOK1 are switched off; these genes have preferably been removed by knock-out in their entirety or in part, or have been mutated. A further embodiment relates to a mutated *S. cerevisiae* cell which is deposited at the Deutsche Sammlung von Mikroorganismen und Zellkulturen GmbH (Mascheroder Weg 1b, D-38124 Braunschweig) in compliance with the provisions of the Budapest Treaty on the International recognition of the deposit of microorganisms for the purposes of patent procedure; deposit number DSM 13197.

A particular embodiment of the invention relates to a mutated *S. cerevisiae* cell which heterologously expresses a eukaryotic potassium channel, the eukaryotic potassium channel preferably being a human potassium channel, for example a HERG1, Kv1.5 or gpIRK1 or a human Kv 4.3 [Genbank Accession Number AF 187963], TASK (Genbank Assession Number AF 006823] or ROMK2 [Genbank Accession Number U 12542] and where the potassium channel has the natural sequence or can be mutated.

The invention also relates to a process for the preparation of a mutated *S. cerevisiae* cell which does not express the potassium channels TRK, TRK2 and TOK1, the genes TRK1, TRK2 and TOK1 having been destroyed or deleted by knockout.

The mutated *S. cerevisiae* cell can be used for example in processes for identifying substances which inhibit or activate the activity of the eukaryotic potassium channel, or it can be part of a test kit which can be used for example for determining toxic substances.

The invention also relates to a process for identifying activators of a eukaryotic potassium channel, in which
  a) a mutated *S. cerevisiae* cell is used which does not express the three endogenous potassium channels TRK1, TRK2 and TOK1;
  b) a eukaryotic potassium channel is expressed heterologously in this mutated *S. cerevisiae* cell;
  c) the mutated *S. cerevisiae* cell is incubated together with a substance to be tested; and
  d) the effect of the substance to be tested on the eukaryotic potassium channel is determined.

The invention furthermore relates to a process for identifying activators of a eukaryotic potassium channel, in which
  a) a mutated *S. cerevisiae* cell is used which does not express the three endogenous potassium channels TRK1, TRK2 and TOK1;
  b) a eukaryotic potassium channel is expressed heterologously in this mutated *S. cerevisiae* cell;
  c) the mutated *S. cerevisiae* cell is incubated together with a substance to be tested in the presence of an inhibitor of the eukaryotic potassium channel; and
  d) the effect of the substance to be tested on the eukaryotic potassium channel is determined.

The invention also relates to a process for the preparation of a medicament, in which
  a) an Inhibitor of a eukaryotic potassium channel is identified,
  b) the Inhibitor is prepared or isolated by known chemical processes, and
  c) physiologically acceptable additives are added to the inhibitor.

The invention also relates to a process for the preparation of a medicament, in which
  a) an activator of a eukaryotic potassium channel is identified,
  b) the activator is prepared or isolated by known chemical processes, and
  c) physiologically acceptable additives are added to the activator.

FIGURES

FIG. 1: Diagnostic PCR for verifying the triple knock-out. Explanation of the rows/lanes in the gel, see text, Example 2, triple knock-out.

Figure 2:
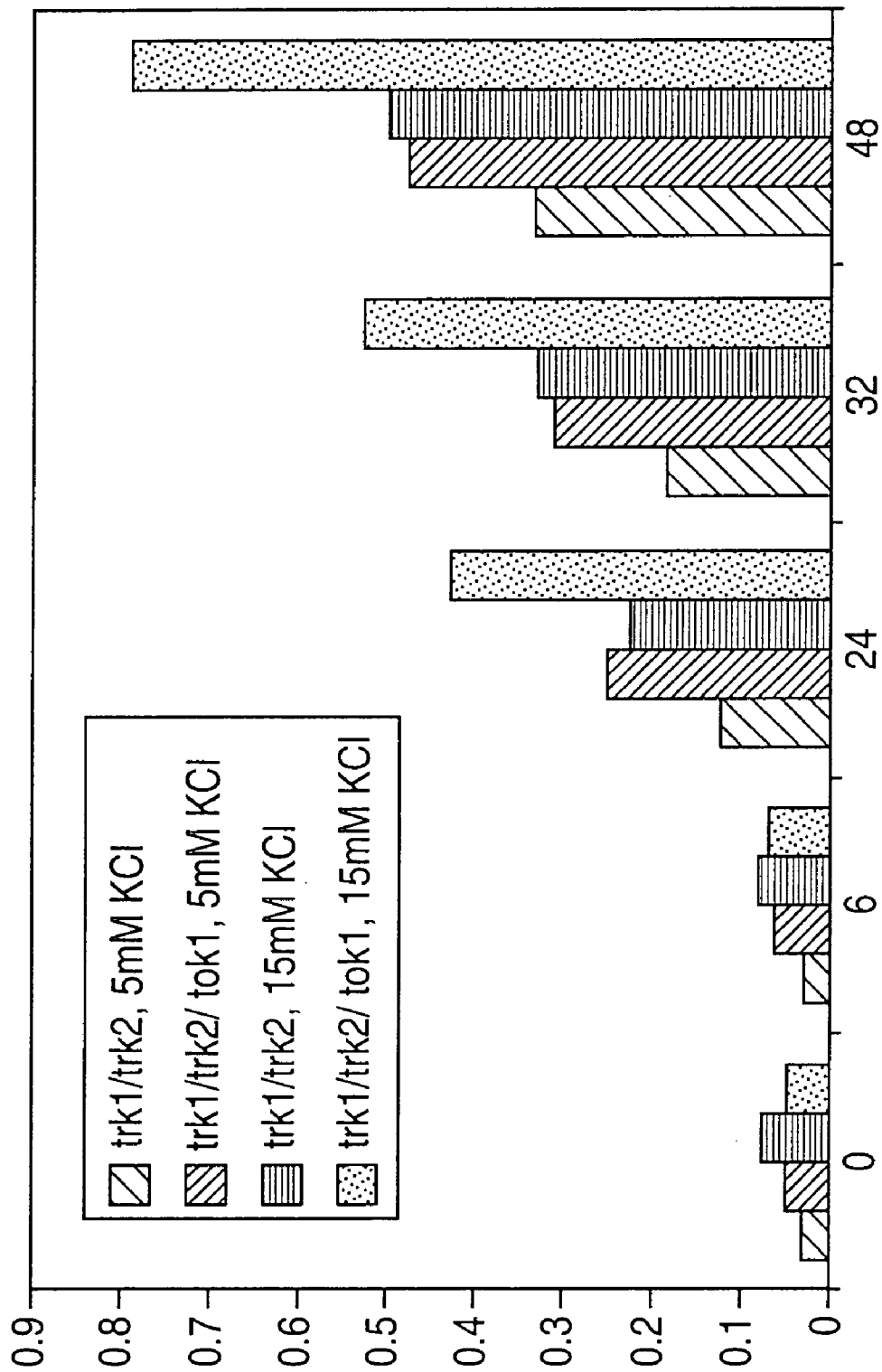

FIG. 2: Growth of strains YM168 (Δtrk1 Δtrk2) and YM182 (Δtrk1 Δtrk2 Δtok1) on DPM medium with defined KCl concentrations at pH 6.5.

Figure 3:
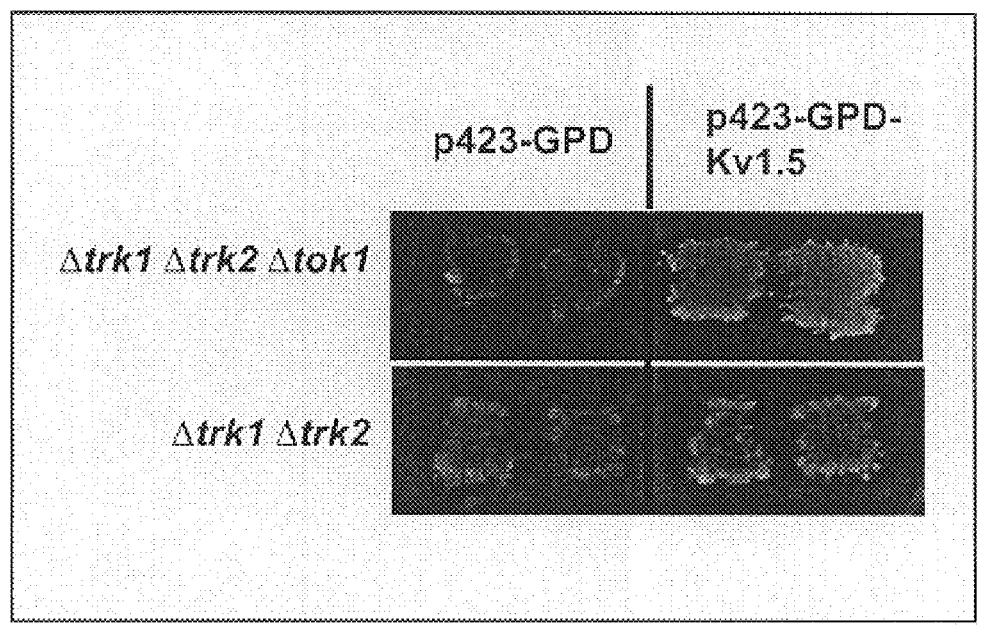

FIG. 3: Growth of strains YM189 and YM190 (in Δtrk1 Δtrk2), and YM194 and YM195 (in Δtrk1 Δtrk2 Δtok1) on DPM medium with 5 mM KCl+2 mM RbCl at pH 6.5.

Figure 4:
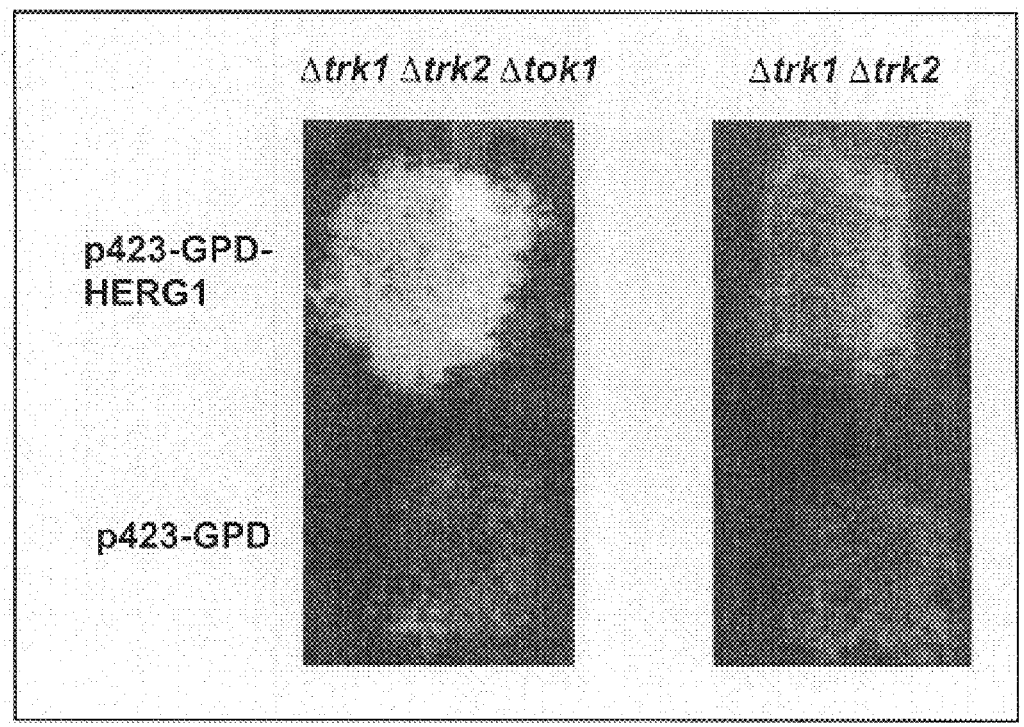

FIG. 4: Growth of strains YM189 and YM191 (in Δtrk1 Δtrk2), and YM194 and YM196 (in Δtrk1 Δtrk2 Δtok1) on DPM medium with 5 mM KCl+2 mM CsCl at pH 6.5.

Figure 5:
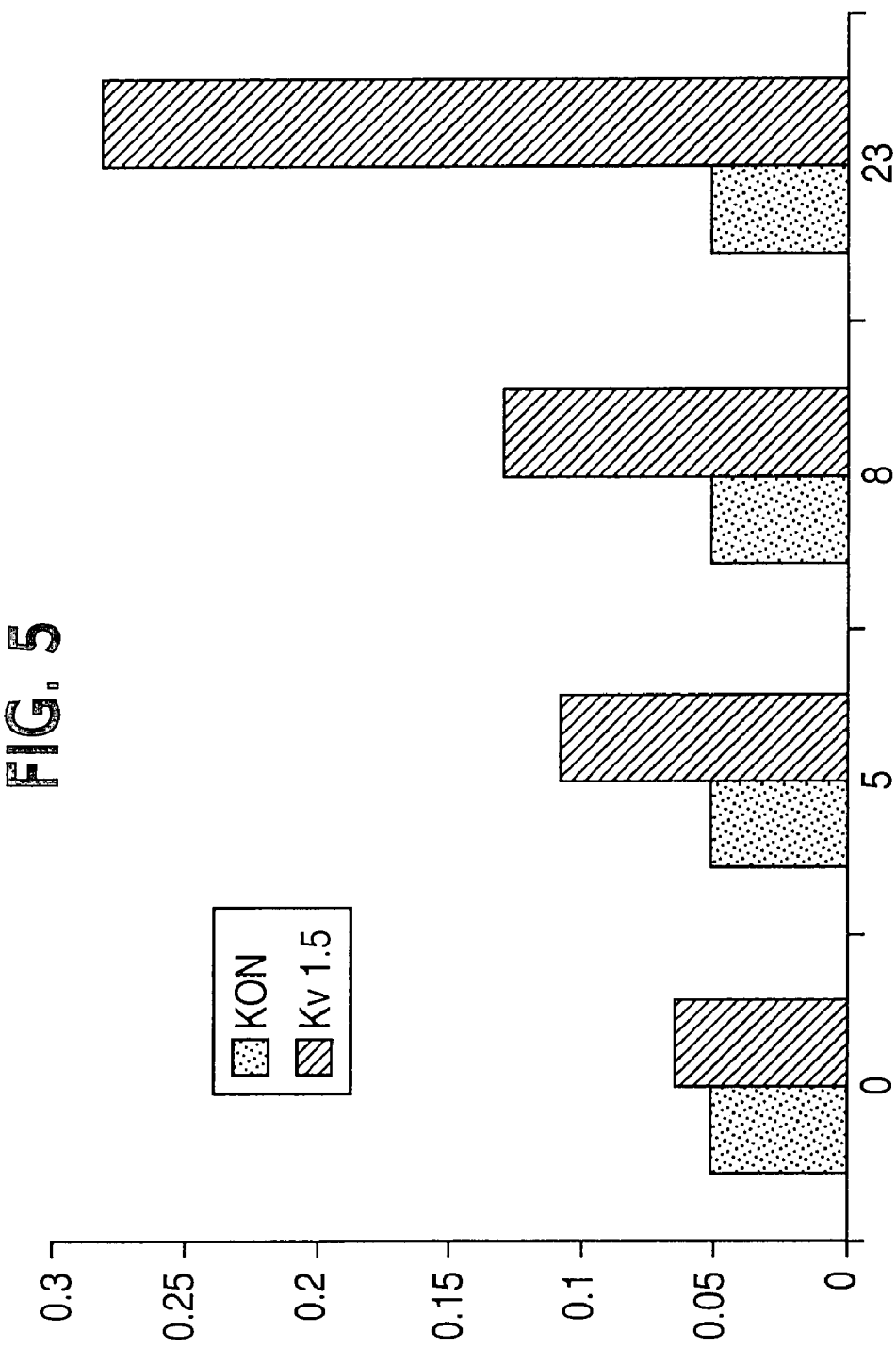

FIG. 5: Growth of strains YM194 and YM195 (in Δtrk1 Δtrk2 Δtok1) in DPM medium with 5 mM KCl+1 mM RbCl at pH 6.5. ("KON"=control)

Figure 6:
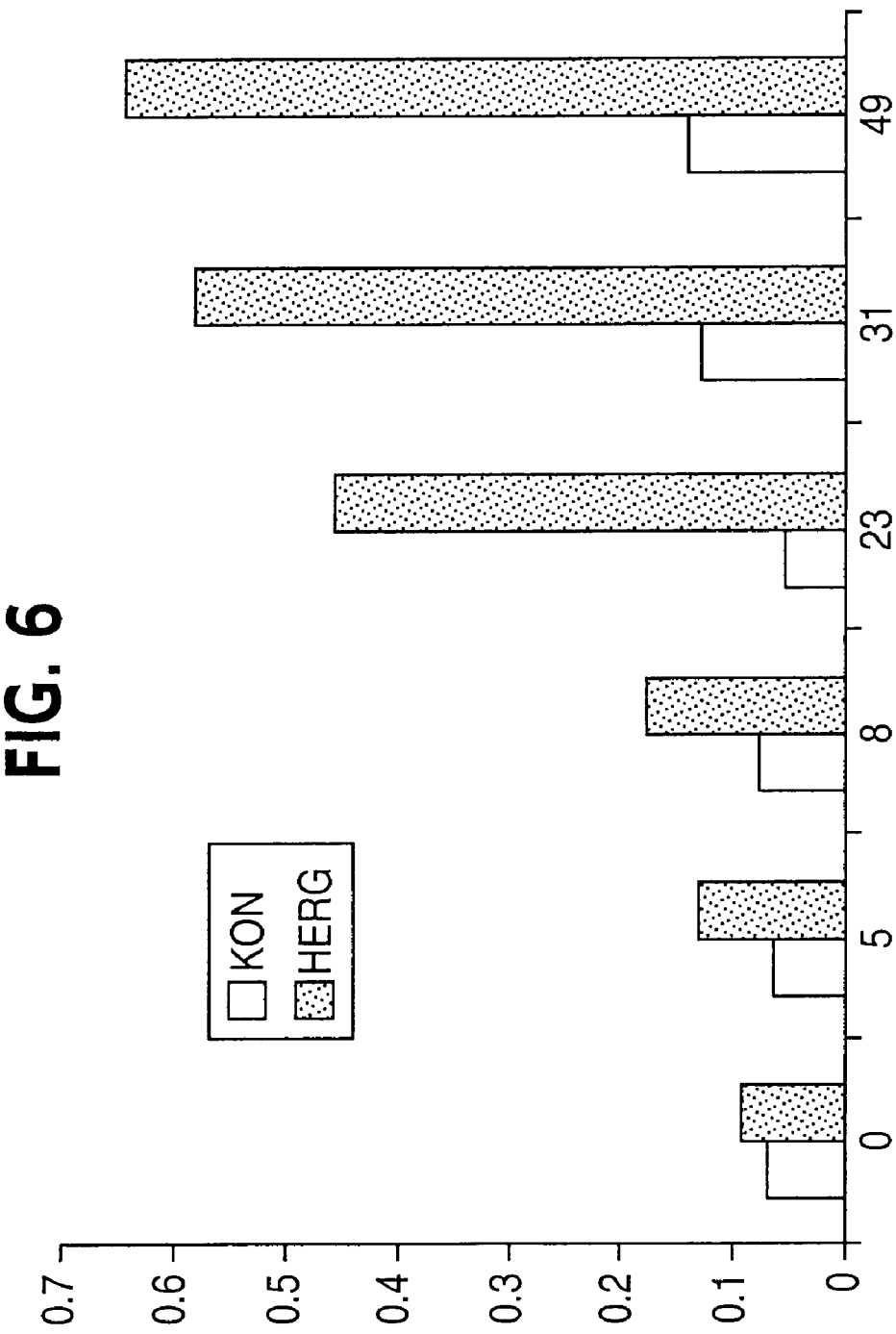

FIG. 6: Growth of strains YM194 and YM196 (in Δtrk1 Δtrk2 Δtok1) in DPM medium with 5 mM KCl+1 mM CsCl at pH 6.5. ("KON"=control)

Figure 7:
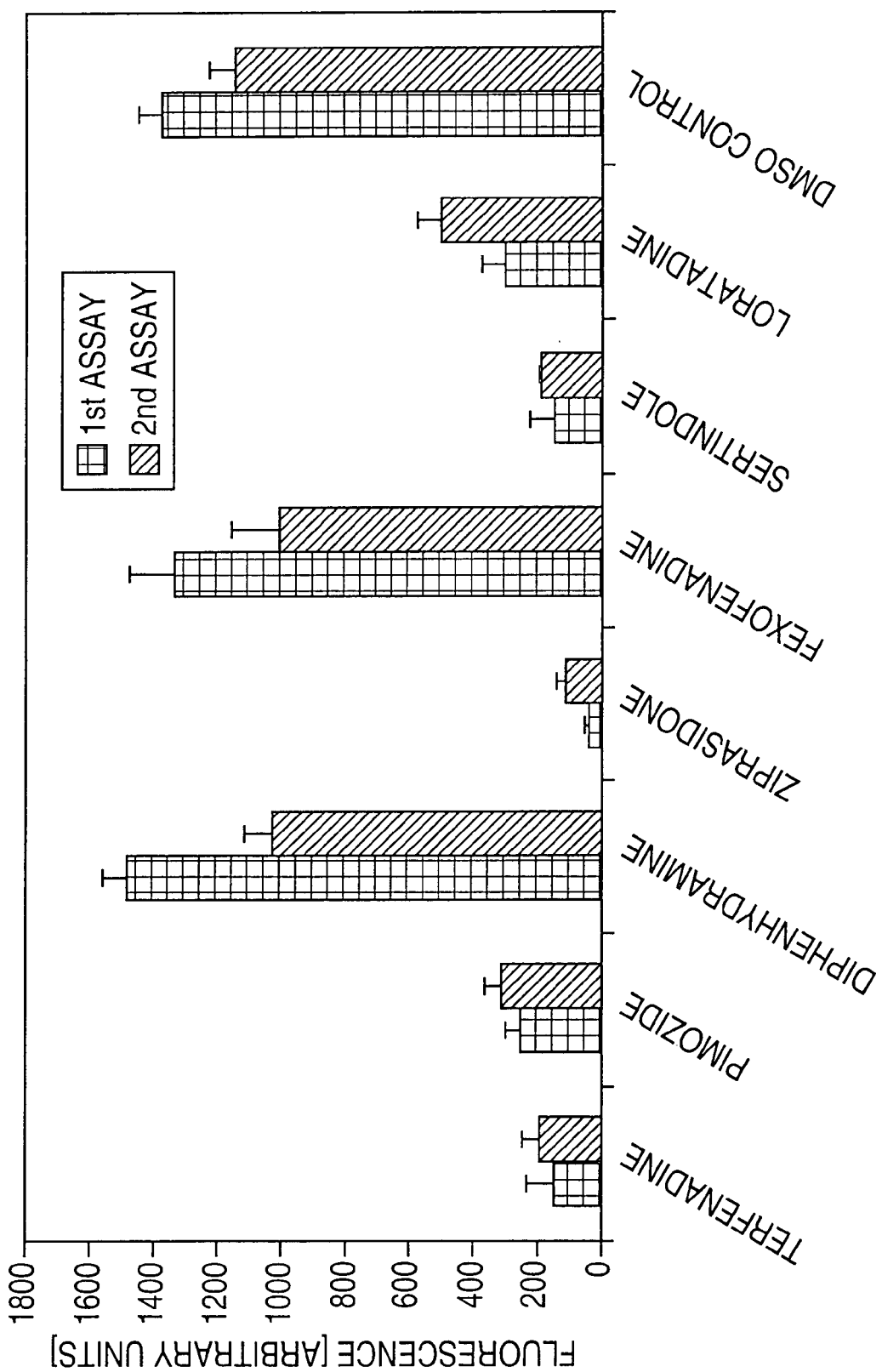

FIG. 7: Expression of the human potassium channel HERG1 in the triple mutant Δtrk1Δtrk2Δtok1 in DPM-HIS/-TRP 5 mM KCl medium in 96-well ELISA plates in the presence of 0.5 mM CsCl as activator.

The various inhibitors were employed at a final concentration of in each case 30 μM. To measure the cell density, a commercially available LacZ reporter system pYX232 by Ingenius (cat. No. MBV-032-10) was transformed into the yeast strains to be studied. Expression of the LacZ reporter gene was under the control of the constitutive *Saccharomyces cerevisiae* promotor TPI for the triose phosphate isomerase gene. The LacZ enzyme activity was measured via detecting the luminescence after 24 hours' growth (density of the starter culture: 0.01 $OD_{620}$) using a commercially available assay system by TROPIX. The values correspond to the average of in each case 4 measurements ±SD. The two different assays were carried out independently of each other on two different days.

Figure 8:
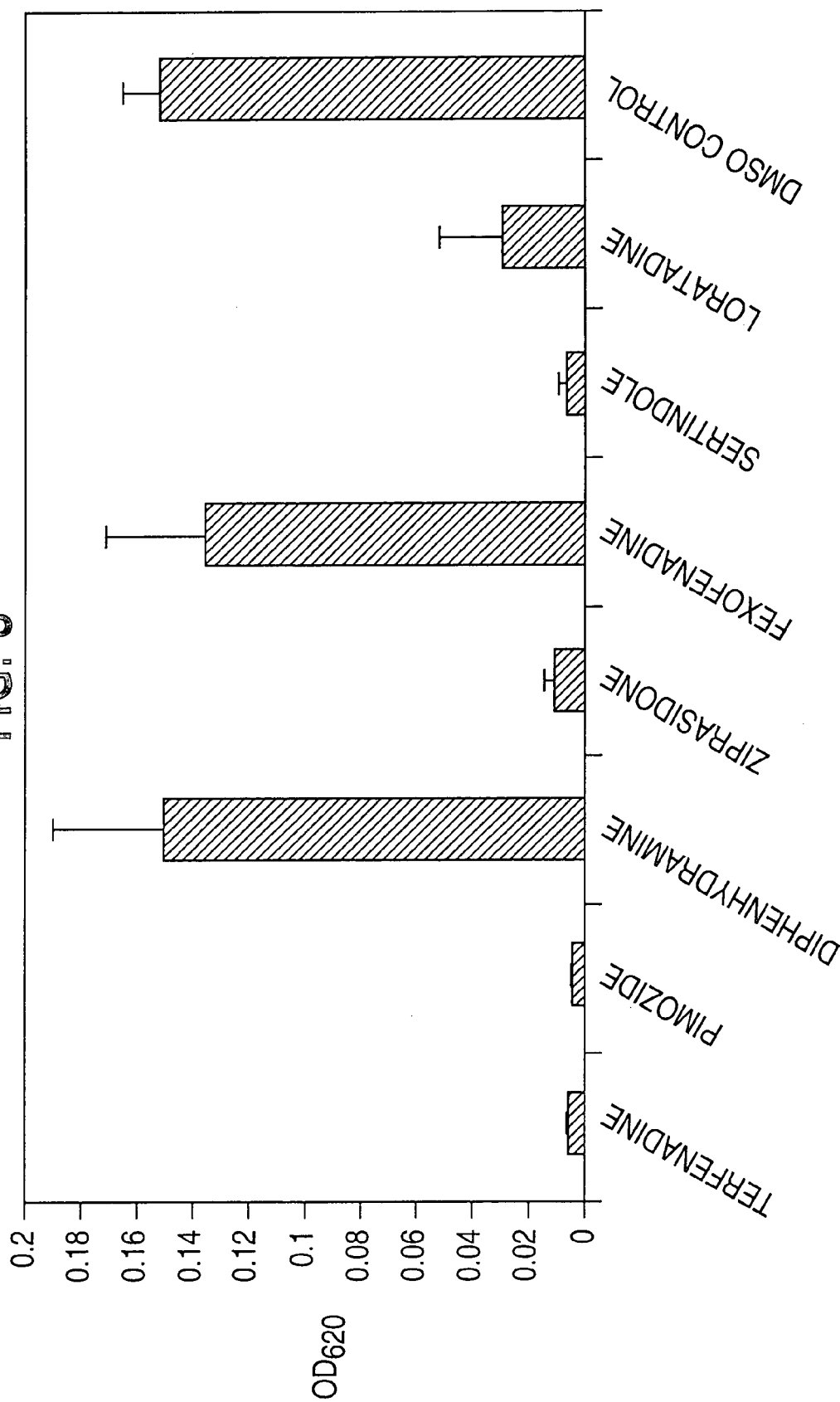

FIG. 8: Expression of the human potassium channel HERG1 in the triple mutant Δtrk1Δtrk2Δtok1 in DPM-HIS 5 mM KCl medium in 96-well ELISA plates in the presence of 0.5 mM CsCl as activator.

The various inhibitors were employed at a final concentration of in each case 30 μM. The cell density was measured after 38 hours' growth (density of the starter culture: 0.03 $OD_{620}$) via determination of the optical density at a wavelength of 620 nm. The values corresponded to the average of in each case 4 measurements ±SD.

Figure 9:
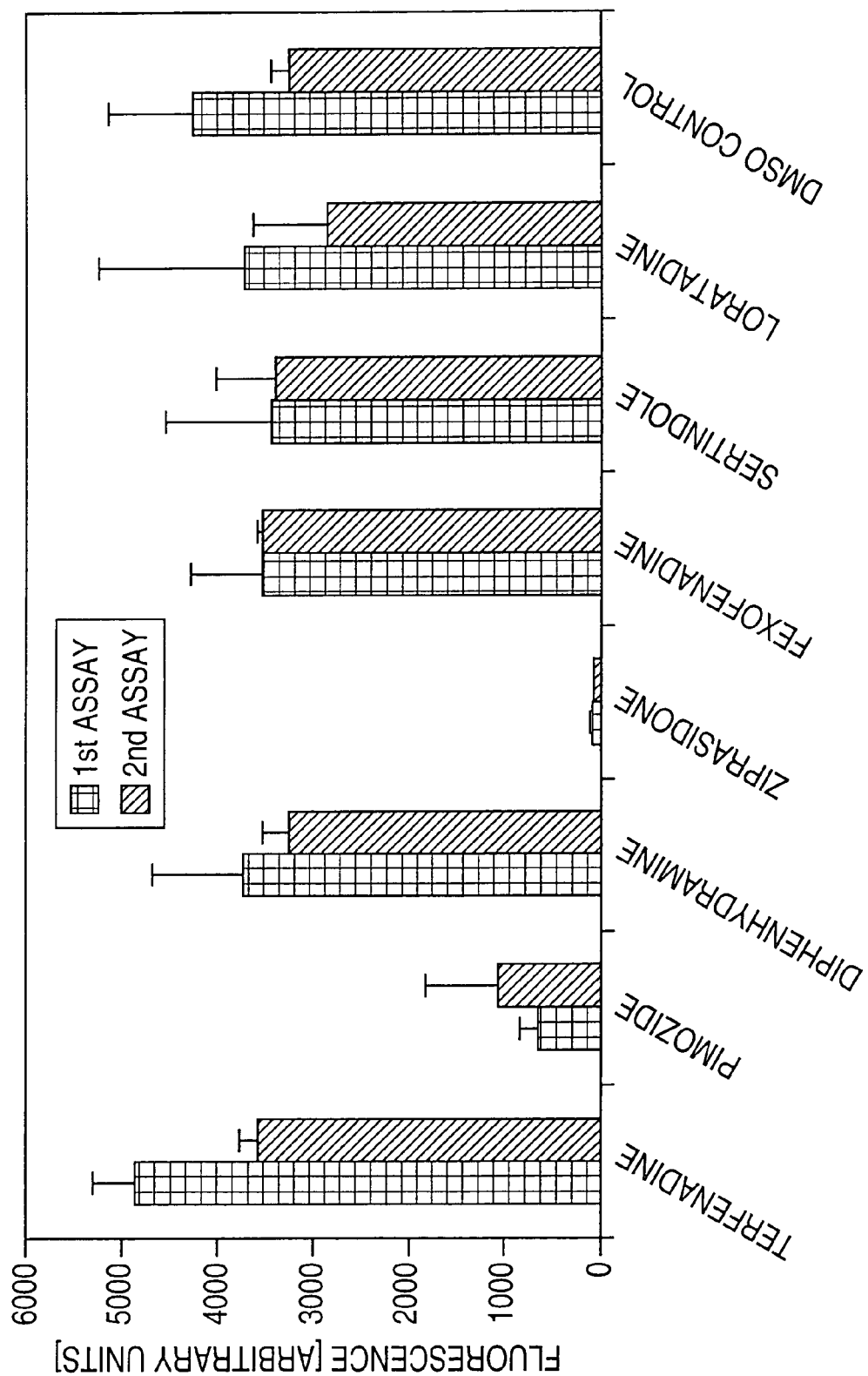

FIG. 9: Growth of the *Saccharomyces cerevisiae* wild-type strain in DPM-HIS/-TRP 5 mM KCl medium in 96-well ELISA plates in the presence of 0.5 mM CsCl. The various inhibitors were employed at a final concentration of in each case 30 μM. To measure the cell density, a commercially available LacZ reporter system pYX232 by Ingenius (cat. No. MBV-032-10) was transformed into the yeast strains to be studied. Expression of the LacZ reporter gene was under the control of the constitutive *Saccharomyces cerevisiae* promotor TPI for the triose phosphate isomerase gene. The LacZ enzyme activity was measured via detecting the luminescence after 24 hours' growth (density of the starter culture: 0.01 $OD_{620}$) using a commercially available assay system by TROPIX.

The values correspond to the average of in each case 4 measurements ±SD. The two diferent assays were carried out independently of each other on two different days.

Figure 10:
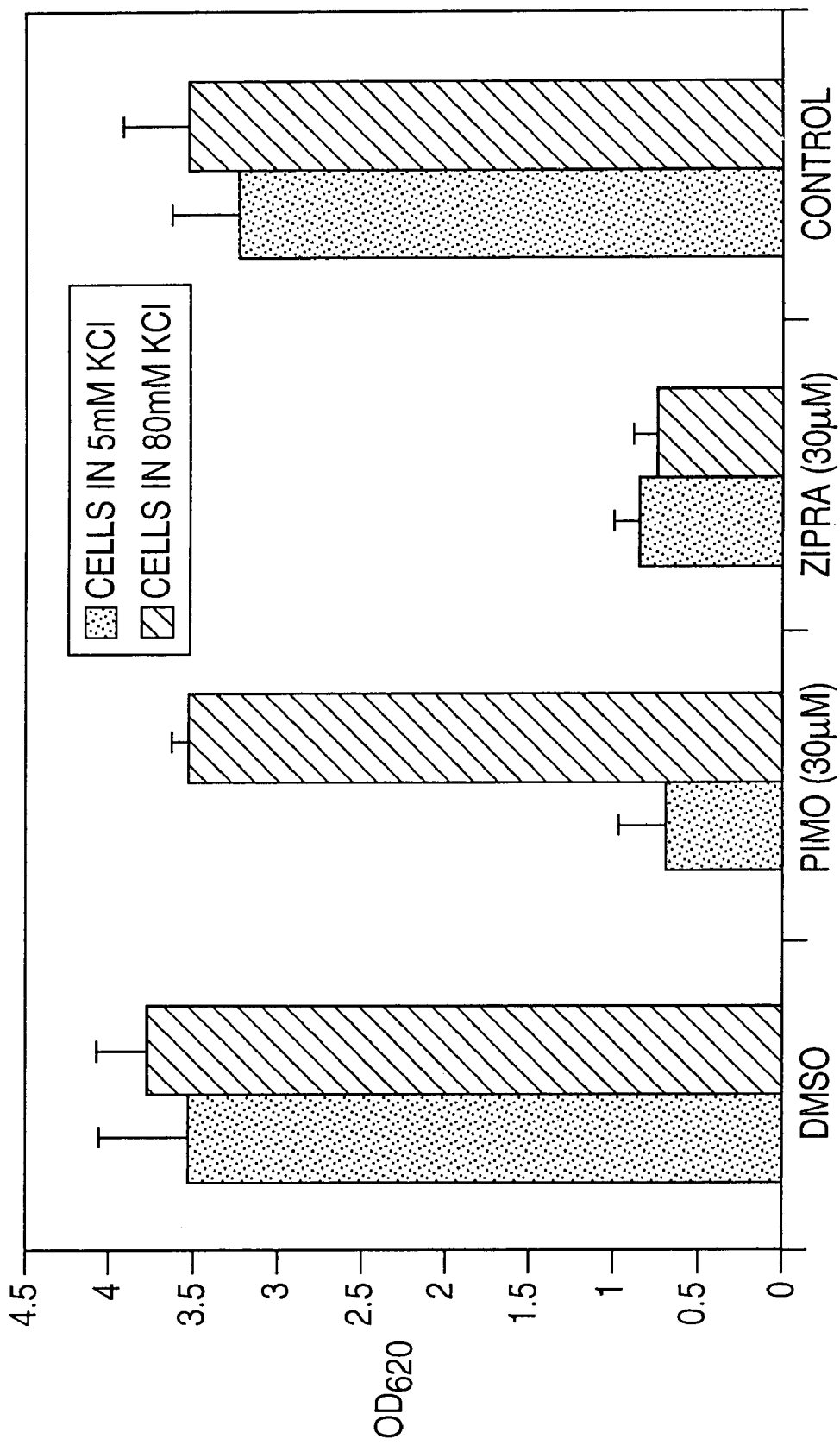

FIG. 10: Growth of the *Saccharomyces cerevisiae* wild-type strain in DPM medium in 96-well ELISA plates in the presence of 5 mM KCl or in the presence of 80 mM KCl. The inhibitors Ziprasidone and Pimozide were employed at a final concentration of in each case 30 μM. The cell density was measured after 24 hours' growth (density of the starter culture: 0.01 $OD_{620}$) via determination of the optical density at a wavelength of 620 nm. The values corresponded to the average of in each case 4 measurements ±SD.

Figure 11:
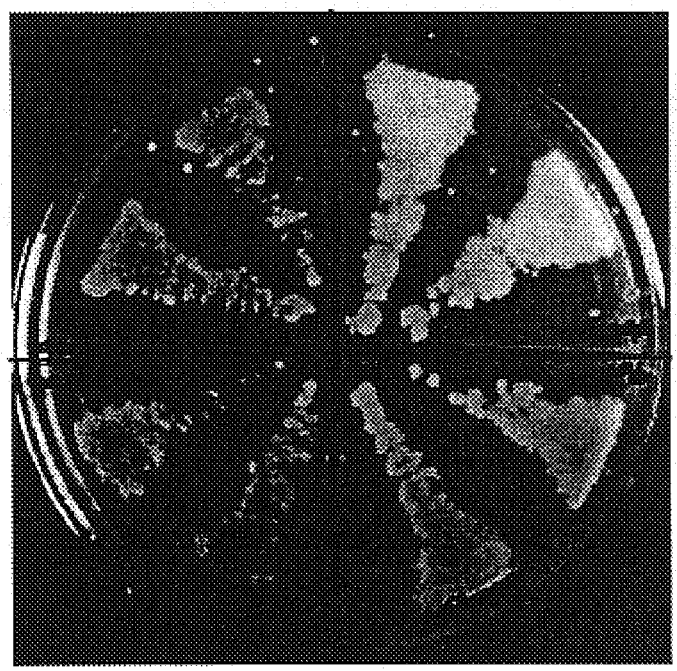

FIG. 11: Expression of the human potassium channel HERG1 in triple mutant Δtrk1Δtrk2Δtok1, and in the double mutant Δtrk1Δtrk2 on DPM-HIS medium in the presence of 5 mM KCl and 0.5 mM CsCl as activator.

1: Growth of the triple mutant Δtrk1Δtrk2Δtok1 upon expression of the blank vector p423GPD as negative control. 2: Growth of the triple mutant Δtrk1Δtrk2Δtok1 upon expression of p423GPD-TRK1 as positive control. 3: Growth of the triple mutant Δtrk1Δtrk2Δtok1 upon expression of p423GPD-HERG1. 4: Growth of the double mutant Δtrk1Δtrk2 upon expression of p423GPD-HERG1. The vectors and constructs used are explained in the patent application (see pages 12 et seq. and 15 et seq.).

Figure 12:
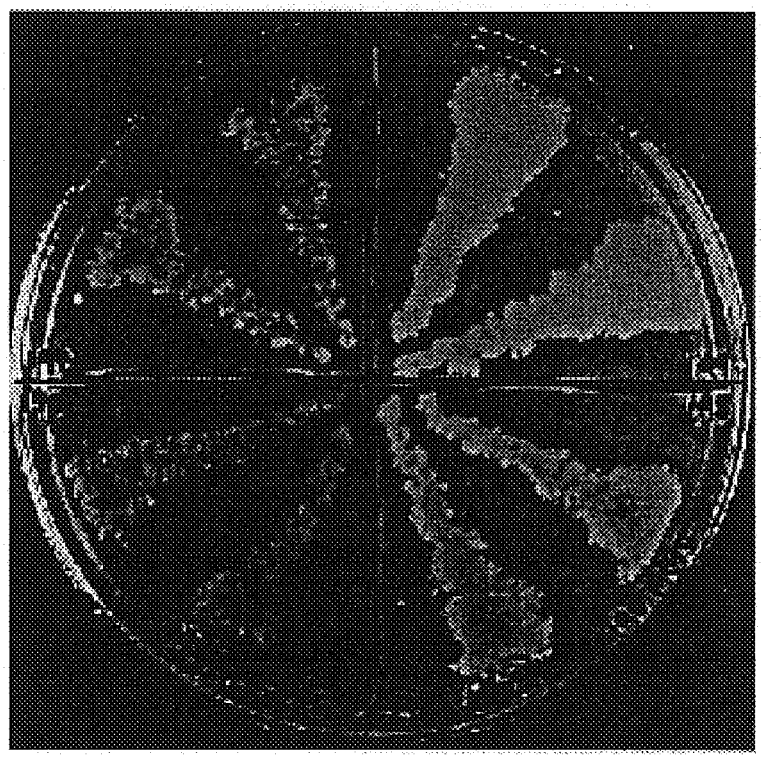

FIG. 12: Expression of the human potassium channel Kv1.5 in triple mutant Δtrk1Δtrk2Δtok1, and in the double mutant Δtrk1Δtrk2 on DPM -HIS medium in the presence of 5 mM KCl and 2 mM RbCl as activator.

1: Growth of the triple mutant Δtrk1Δtrk2Δtok1 upon expression of the blank vector p423GPD as negative control. 2: Growth of the triple mutant Δtrk1Δtrk2Δtok1 upon expression of p423GPD-TRK1 as positive control. 3: Growth of the triple mutant Δtrk1Δtrk2Δtok1 upon expression of p423GPD-Kv1.5. 4: Expression of the double mutant Δtrk1Δtrk2 upon expression of p423GPD-Kv1.5. The vectors and constructs used are explained in the patent application (see pages 12 et seq. and 15 et seq.).

Figure 13:
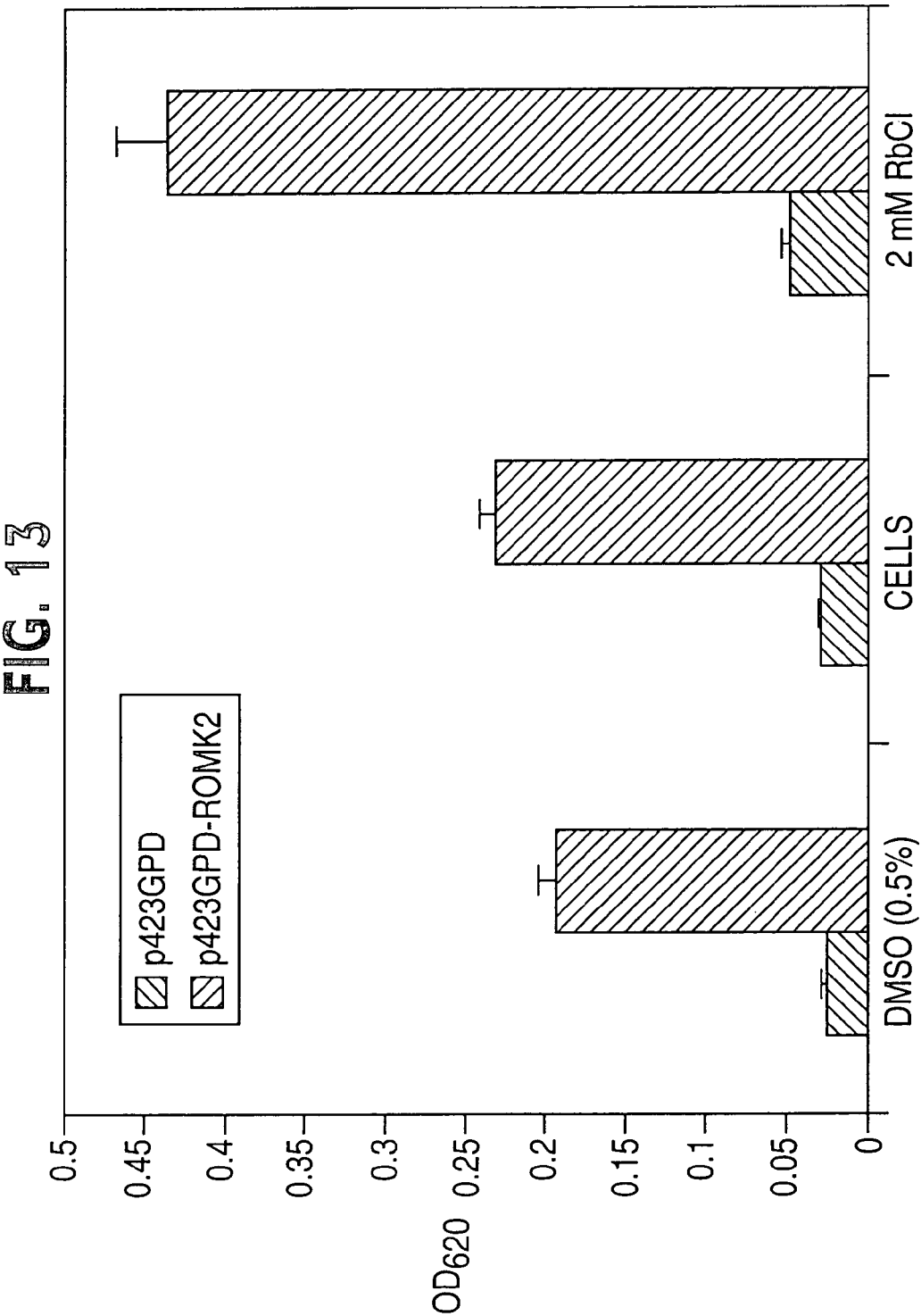

FIG. 13: Expression of the human potassium channel ROMK2 and of the yeast vector p423GPD as negative control in the triple mutant Δtrk1Δtrk2Δtok1 in DPM -HIS 5 mM KCl medium in 96-well ELISA plates.

The cell density was measured after 24 hours' growth (density of the starter culture: 0.01 $OD_{620}$) via determination of the optical density at a wavelength of 620 nm. The values corresponded to the average of in each case 4 measurements ±SD.

Figure 14:
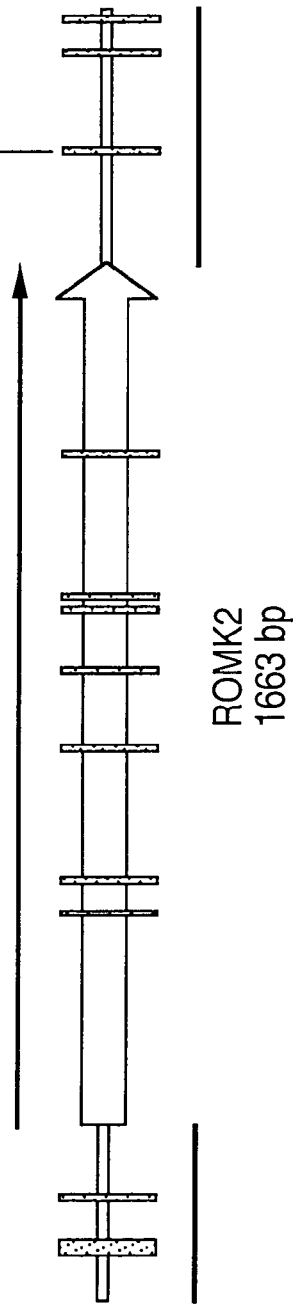

FIG. 14: Plasmid map of p423 GPD-ROMK2.

EXAMPLES

Materials and Strains

Media

YPD (complete yeast medium): 1% Bacto yeast extract, 2% Bacto peptone, 2% Bacto agar, 2% glucose.

SC (synthetic complete) Medium: 0.67% Bacto yeast nitrogen base, amino acids, 2% glucose.

Sporulation medium: 1% potassium acetate, amino acids.

5-FOA medium: 0.67% Bacto yeast nitrogen base, amino acids, Uracil (50 μg/ml), 2% sugar (galactose or glucose), 0.1% 5-FOA All media are described in: (Fink, G. R. et al., 1991)

Amino Acid Dropout Mix:

L-alanine 2 g; L-arginine 2 g; L-asparagine*H$_2$O 2.27 g; L-aspartic acid 2 g;

L-cysteine*HCl 2.6 g; L-glutamine 2 g; L-glutamic acid 2 g; glycine 2 g; myoinositol 2 g;

L-isoleucine 2 g; L-methionine 2 g; PABA 0.2 g; L-phenylalanine 2 g; L-proline 2 g;

L-serine 2 g; L-threonine 2 g; L-tyrosine 2 g; L-valine 2 g.

Stock Solutions for Marker Amino Acids:

|  | mM | g/l |  |
|---|---|---|---|
| Adenine (100×) | 30 | 5.53 | heating (up to not more than 60° C.) |
| Leucine (60×) | 100 | 13.12 | heating |
| Lysine (100×) | 100 | 18.26 | — |
| Histidine (200×) | 60 | 12.57 | — |
| Tryptophan (100×) | 40 | 8.17 | — |
| Uracil (100×) | 20 | 2.24 | heating in 0.5% NaHCO$_3$ solution |

Vitamin stock (50 ml): biotin 20 μg/l; calcium pantothenate 40 μg/l; thiamine 40 μg/l.

Defined potassium medium (DPM): for 1.5 l (2× stock):

| | | |
|---|---|---|
| $(NH_4)_2HPO_4$ | 8 mM | 3.2 g |
| $(NH_4)_2SO_4$ | 29 mM | 11.5 g |
| $MgSO_4$ | 2 mM | 0.8 g (or 6 ml of 1 M stock) |
| $CaCl_2$ | 0.2 mM | 90 μg (or 1.2 ml of 0.5 M stock) |
| Vitamin stock | | 120 μl |
| Amino acid dropout mix | | 6 g |
| Lysine | | 330 ml of 100× stock |
| Adenine | 0.9 mM | 30 ml of 100× stock |
| → bring to pH 6.5 (or an other pH) with HCl, autoclave | | |
| Glucose | 2% | from 40% stock |
| KCl | | from 1 M stock |
| essential amino acids (with the exception of Lys/Ade) from stocks | | |
| Agar | | |

Buffer and Solutions:

TE buffer: Tris/HCl (pH 7.5) 10 mM; EDTA (pH 8.0) 1 mM;

TAE buffer: Tris 40 mM; EDTA 1 mM; acetic acid 0.2 mM;

SSC buffer (20×): NaCl 3 M; sodium citrate*2 $H_2O$ 0.3 M;

Gel loading buffer: Bromphenol Blue 0.05% (w/v); sucrose 40% (w/v); EDTA, pH 8.0 0.1 M; SDS 0.5% (w/v);

Hybridization buffer: SSC 5×; SDS 0.1% (w/v); dextran sulfate 5% (w/v); stop reagent 1:20;

Buffer A (sterile): Tris-HCl 100 mM; NaCl, pH 9.5 300 mM;

Depurination solution: HCl 0.25 M;

Denaturation solution: NaCl 1.5 M; NaOH 0.5 M;

Neutralization solution: NaCl 1.5 M; Tris, pH 8.0 0.5 M.

Oligonucleotides (PCR Primers):

| Name | Sequence (5'→3') | | RE |
|---|---|---|---|
| TRK1-FL-BamHI-Fo | GCG'GATCCATGCATTTTAGAAGAACGATGAGTAG: | SEQ ID NO. 7 | BamHI |
| TRK1-FL-PstI-Re | AGGTTCTGCTGCA'GTTGGTGT: | SEQ ID NO. 8 | PstI |
| TRK1-FL-PstI-Fo | ACACCAACTGCA'GCAGAACCT: | SEQ ID NO. 9 | PstI |
| TRK1-FL-XhoI-Re | CGC'TCGAGTTAGAGCGTTGTGCTGCTCCT: | SEQ ID NO. 10 | XhoI |
| TRK1-Dia-Fo | CCTTACCATTAGCATCACTGAT: | SEQ ID NO. 11 | — |
| TRK1-Dia-Re1 | CTATTAACCATTTCTCCGCTG: | SEQ ID NO. 12 | — |
| URA-Rev | GATTTATCTTCGTTTCCTGCAGGT: | SEQ ID NO. 13 | — |
| TRK2-DEL-5-Fo-B | CAC'GTACGTCCAGCACAATTTCACAACAGCT: | SEQ ID NO. 14 | Bs/WI |
| TRK2-DEL-5-Re | CAG'TCGACCTGGATGACGTCCTCTTAGCTG: | SEQ ID NO. 15 | Sa/I |
| TRK2-DEL-3-Fo | CAGAT'ATCATGCTGCCAAGTGACAAACTG: | SEQ ID NO. 16 | EcoRV |
| TRK2-DEL-3-Re | TCA'CTAGTTGTTGATGGCTTTGGTTGGT: | SEQ ID NO. 17 | SpeI |
| TRK2-Dia-Fo | GCGAAGAATAGGATGAGATGTG: | SEQ ID NO. 18 | — |
| TRK2-Dia-Re1 | TTGTCGTGGGTCTTCTCTGG: | SEQ ID NO. 19 | — |
| KAN-Rev | GCTACCTTTGCCATGTTTCAGAA: | SEQ ID NO. 20 | — |
| TOK1-DEL-5-Fo | CAC'GTACGGCAAATTTATCGAGACTCTGCGA: | SEQ ID NO. 21 | Bs/WI |
| TOK1-DEL-5-Re | AGG'TCGACCATATTGCCATATCCCAGCGT: | SEQ ID NO. 22 | Sa/I |
| TOK1-DEL-3-Fo | TGGAT'ATCACCTGATACGCCC: | SEQ ID NO. 23: | EcoRV |
| TOK1-DEL-3-Re | CAA'CTAGTGCATACCAGTAGTATGAGACATGCTTG: | SEQ ID NO. 24 | SpeI |
| TOK1-Dia-Fo | CCTGAGTACTCAGTACCATCTTG: | SEQ ID NO. 25 | — |
| TOK1-Dia-Re1 | CTGTAGATGCTGGGCATG: | SEQ ID NO. 26 | — |
| Kv1.5-GFP-Fo | TACG'TCGACATGGAGATCGCCCTGGTG: | SEQ ID NO. 27 | Sa/I |
| Kv1.5-GFP-Re | TACG'TCGACATCTGTTTCCCGGCTGGTG: | SEQ ID NO. 28 | Sa/I |
| HERG1-GFP-Fo | TACAT'CGATATGCCGGTGCGGAGGG: | SEQ ID NO. 29 | C/aI |
| HERG1-GFP-Re | TACG'TCGACACTGCCCGGGTCCGA: | SEQ ID NO. 30 | Sa/I |

Vectors:

Bacterial vectors

| Name | Size (bp) | Genes |
|---|---|---|
| pcDNA3 (Invitrogen) | 5446 | CMV prom., T7 prom., polylinker, Sp6 prom., BGH poly (A), SV40 prom., SV 40 ori, Neomycin$^R$, SV 40 poly (A), ColE1 ori, Amp$^R$ |
| pcDNA3.1 (+/−) (Invitrogen) | 5432 | CMV prom., T7 prom./priming site, MCS, pcDNA3.1 reverse priming site, BGH poly (A), F1 ori, SV40 prom., SV 40 ori, Neomycin$^R$, SV 40 poly (A), ColE1 ori, Amp$^R$ |
| pUG6 | 4009 | loxP-TEF2 prom.-kanMX-loxP-TEF2 term., ori, Amp$^R$ |
| pCR ®-Blunt II-TOPO | 3519 | lac prom./op., M13 reverse prim. site, LacZ-α ORF, SP6 prom. prim. site, MCS, TOPO ™ cloning site, T7 prom. prim. site, M13 (−20) forward prim. site, M13 (−40) prim. site, fusion point, ccdB lethal gene ORF, kan gene, (kan prom., kanamycin resistance gene ORF), zeocin resistance ORF, pMB1 origin (pUC-derived) |
| pCR ® II-TOPO | 3900 | LacZ-α gene, M13 reverse prim. site, SP6 prom., MCS, T7 prom., M13 (−20) forward prim. site, M13 (−40) forward prim. site, f1 origin, kanamycin resistance ORF, ampicillin resistance ORF, pMB1 origin (pUC-derived) |

Yeast vectors

| Name | Size (bp) | Genes |
|---|---|---|
| pSH47 | 6786 | CEN6/ARSH4, URA3, CYC1 term., CRE, GAL1 prom., Amp |
| p414 GAL1 | 5474 | CEN6/ARSH4, TRP1, CYC1 term., GAL1 prom., Amp$^R$ |
| p416 GAL1 | 5584 | CEN6/ARSH4, URA3, CYC1 term., GAL1 prom., Amp$^R$ |
| p416 ADH | 6624 | CEN6/ARSH4, URA3, CYC1 term., ADH prom., Amp$^R$ |
| p423 GPD3 | 6678 | 2μ, HIS3, CYC1 term., GPD3 prom., Amp$^R$ |
| p426 GAL1 | 6417 | 2μ, URA3, CYC1 term., GAL1 prom., Amp$^R$ |
| p426 GAL1-yEGFP3 | 7140 | 2μ, URA3, CYC1 term., yEGFP3, GAL1 prom., Amp$^R$ |
| p426 GAL1-SP-yEGFP3 | 7227 | 2μ, URA3, CYC1 term., N-terminal 24 aa of Ste2, yEGFP3, GAL1 prom., Amp$^R$ |

Strains:

Bacterial strains: DH5α; One Shot™ TOP10 (Invitrogen)

Yeast Strains:

All yeast strains generated for this work are based on the diploid wild-type strain:

W303 MATa/α ade2, his3-11-15, leu2-3-112, trp1-1, ura3-1, can1-100;

ATCC No. 208352.

| Strain | Original Name | Mating type | Genes |
|---|---|---|---|
| YM 96 | w303 | MATa/α | ade2, his3-11-15, leu2-3-112, trp1-1, ura3-1, can1-100 |
| YM 97 | w303 | MATa | ade2, his3-11-15, leu2-3-112, trp1-1, ura3-1, can1-100 |
| YM 98 | w303 | MATα | ade2, his3-11-15, leu2-3-112, trp1-1, ura3-1, can1-100 |

The following yeast strains were generated:

| Strain | Original Name | Mating type | Genes (with the exception of ade2, his3-11-15, leu2-3-112, trp1-1, ura3-1, can1-100) |
|---|---|---|---|
| YM 123 | Δtrk1 in YM 96 | MATα | trk1::hisG-URA3-hisG |
| YM 124 | Δtrk1 in YM 96 | MATa | trk1::hisG-URA3-hisG |
| YM 139 | Δtok1 in YM 96 | MATa/α | tok1::loxP-KanMX-loxP |
| YM 140 | Δtok1 in YM 123 | MATα | trk1::hisG-URA3-hisG, tok1::loxP-KanMX-loxP |
| YM 141 | Δtok1 in YM 123 | MATα | trk1::hisG-URA3-hisG, tok1::loxP-KanMX-loxP |
| YM 142 | Δtok1 in YM 96 | MATa/α | tok1::loxP-KanMX-loxP |
| YM 143 | Δtok1 in YM 124 | MATa | trk1::hisG-URA3-hisG, tok1::loxP-KanMX-loxP |
| YM 144 | Δtok1 in YM 124 | MATa | trk1::hisG-URA3-hisG, tok1::loxP-KanMX-loxP |
| YM 154 | Δtok1 in YM 96 | MATα | tok1::loxP-KanMX-loxP |
| YM 155 | Δtok1 in YM 96 | MATa | tok1::loxP-KanMX-loxP |
| YM 156 | Δtok1 in YM 96 | MATa | tok1::loxP-KanMX-loxP |
| YM 157 | Δtok1 in YM 96 | MATα | tok1::loxP-KanMX-loxP |
| YM 158 | Δtrk2 in YM 96 | MATα | trk2::loxP-KanMX-loxP |
| YM 159 | Δtrk2 in YM 96 | MATa | trk2::loxP-KanMX-loxP |
| YM 160 | Δtrk2 in YM 96 | MATa | trk2::loxP-KanMX-loxP |
| YM 161 | Δtrk2 in YM 96 | MATα | trk2::loxP-KanMX-loxP |
| YM 162 | Δtok1 in YM 123 | MATα | trk1::hisG, tok1::loxP |
| YM 163 | Δtok1 in YM 123 | MATα | trk1::hisG, tok1::loxP |
| YM 164 | Δtok1 in YM 124 | MATa | trk1::hisG, tok1::loxP |
| YM 165 | Δtok1 in YM 124 | MATa | trk1::hisG, tok1::loxP |
| YM 166 | YM 124 × YM 160 | MATa | trk1::hisG-URA3-hisG, trk2::loxP-KanMX-loxP |
| YM 167 | YM 124 × YM 160 | MATa | trk1::hisG-URA3-hisG, trk2::loxP-KanMX-loxP |
| YM 168 | YM 124 × YM 160 | MATα | trk1::hisG-URA3-hisG, trk2::loxP-KanMX-loxP |
| YM 169 | YM 124 × YM 160 | MATα | trk1::hisG-URA3-hisG, trk2::loxP-KanMX-loxP |
| YM 182 | Δtrk2 in YM 165 | MATa | trk1::hisG, tok1::loxP, trk2::loxP-KanMX-loxP |
| YM 183 | YM 166 | MATa | trk1::hisG, tok1::loxP, trk2::loxP-KanMX-loxP |
| YM 184 | YM 168 | MATa | trk1::hisG, tok1::loxP, trk2::loxP-KanMX-loxP |
| YM 185 | Kv1.5-pRS426-Gal1-yEGFP3 in YM 97 | MATa | pRS426-GAL1 with Kv1.5-GFP3, trk1::hisG, tok1::loxP, trk2::loxP-KanMX-loxP |
| YM 186 | Kv1.5-pRS426-Gal1-SP-yEGFP3 in YM 97 | MATa | pRS426-GAL1 with N24 Ste2-Kv1.5-GFP3, trk1::hisG, tok1::loxP, trk2::loxP-KanMX-loxP |
| YM 187 | Kv1.5-pRS426-Gal1-yEGFP3 in YM 182 | MATa | pRS426-GAL1 with Kv1.5-GFP3, trk1::hisG, tok1::loxP, trk2::loxP-KanMX-loxP |
| YM 188 | Kv1.5-pRS426-Gal1-SP-yEGFP3 in YM 182 | MATa | pRS426-GAL1 with N24 Ste2-Kv1.5-GFP3, trk1::hisG, tok1::loxP, trk2::loxP-KanMX-loxP |
| YM 189 | P423-GPD3 in YM 168 | MATa | p423-GPD3, trk1::hisG-URA3-hisG, trk2::loxP-KanMX-loxP |
| YM 190 | Kv1.5-p423-GPD3 in YM 168 | MATa | p423-GPD3 with Kv1.5, trk1::hisG-URA3-hisG, trk2::loxP-KanMX-loxP |
| YM 191 | HERG-p423-GPD3 in YM 168 | MATa | p423-GPD3 with HERG, trk1::hisG-URA3-hisG, trk2::loxP-KanMX-loxP |
| YM 192 | HCN2-p423-GPD3 in YM 168 | MATa | p423-GPD3 with HCN2, trk1::hisG-URA3-hisG, trk2::loxP-KanMX-loxP |
| YM 193 | IRK1-p423-GPD3 in YM 168 | MATa | p423-GPD3 with IRK1, trk1::hisG-URA3-hisG, trk2::loxP-KanMX-loxP |
| YM 194 | p423-GPD3 in YM 182 | MATa | p423-GPD3, trk1::hisG, tok1::loxP, trk2::loxP-KanMX-loxP |
| YM 195 | Kv1.5-p423-GPD3 in YM 182 | MATa | p423-GPD3 with Kv1.5, trk1::hisG, tok1::loxP, trk2::loxP-KanMX-loxP |
| YM 196 | HERG-p423-GPD3 in YM 182 | MATa | p423-GPD3 with HERG, trk1::hisG, tok1::loxP, trk2::loxP-KanMX-loxP |
| YM 197 | HCN2-p423-GPD3 in YM 182 | MATa | p423-GPD3 with HCN2, trk1::hisG, tok1::loxP, trk2::loxP-KanMX-loxP |
| YM 198 | IRK1-p423-GPD3 in YM 182 | MATa | p423-GPD3 with IRK1, trk1::hisG, tok1::loxP, trk2::loxP-KanMX-loxP |
| YM 199 | TRK1-p423-GPD3 in YM 182 | MATa | p423-GPD3 with TRK1, trk1::hisG, tok1::loxP, trk2::loxP-KanMX-loxP |

Cloned Potassium Channels:

A)

| | |
|---|---|
| Systematic name | KCNA5 |
| Synonyms | Kv1.5, (HK2, HPCN1) |
| Family | voltage-gated potassium channel, shaker-related subfamily (member No. 5), delayed rectifier |
| Chromosomal localization | 12p13.32-p13.31 |
| Accession | NID g4504818 |
| Protein | 613 aa, 67 kD |
| Distribution in the tissue | heart, pancreatic islets and insulinoma |
| Homologs | mKcna5 (*Mus musculus*), 70% with hHCN4 |
| References | (Roberds, S. L. et al., 1991; Curran, M. E. et al., 1992; Snyders, D. J. et al., 1993) |

B)

| | |
|---|---|
| Systematic name | HCN2 |
| Synonyms | BCNG2 (brain cyclic nucleotide gated channel), HAC1 |
| Family | hyperpolarization-activated and cyclic nucleotide gate potassium channel, belongs to the superfamily of the voltage-gated potassium channels |
| Chromosomal localization | 19p13.3 |
| Accession | NID g4996893 g4775348 |
| Protein | 889 aa |
| Function | pacemaker |
| Distribution in the tissue | brain, heart |
| Homologs | mHcn2 (*Mus musculus*) |
| References | (Ludwig, A. et al., 1999) |

C)

| | |
|---|---|
| Systematic name | KCNH2 |
| Synonyms | HERG1 (longer splice variant) |
| Family | voltage-gated potassium channel, eag related subfamily, member No. 2 |
| Chromosomal localization | 7q35-q36 |
| Accession | NID g4557728 g4156210 |
| Properties | channel activation by $K^+$ channel regulator 1 accelerated |
| References | (Taglialatela, M. et al., 1998; Itoh, T. et al., 1998) |

D)

| | |
|---|---|
| Systematic name | KCNJ2 (guinea pig) |
| Synonyms | Kir2.1, IRK1 |
| Family | inwardly rectifying potassium channel |
| Occurrence in the tissue | brain, heart, lung, kidney, placenta, skeletal musculature |
| References | (Tang, W. et al., 1995) |

Methods:

ROMK2 (see appendix "Sequence ROMK2")
PCR:
Protocol for Powerscript polymerase (PAN Biotech):
Mix for lower reagent (hotstart protocol) (25 μl):

3 μl $H_2O$; 2.5 μl 10× OptiPerform ™ III buffer, pH 9.2; 10 μl 1.25 mM dNTPs (=200 uM);
1.5 μl forward primer (20 pmol/μl); 1.5 μl reverse primer (20 pmol/μl); 1.5 μl 50 mM
$MgCl_2$ (=1.25 mM); 5 μl 5× OptiZyme ™ enhancer.
Mix for upper reagent (35 μl):

23 μl $H_2O$; 3.5 μl 10× OptiPerform ™ III buffer;
1.5 μl 50 mM $MgCl_2$, 0.5 μl
PowerScript DNA polymerase; 7 μl 5× OptiZyme ™ enhancer.
PCR program (hotstart):

1. 1 min at 94° C.
2. 1 min at 94° C.
3. 1.5 minutes at 50-55° C. (depending on primer)
4. 4 minutes at 69-72° C. (depending on polymerase)
5. Repeat 27× from 2.
6. 4° C. ∞
7. End.

Protocol for AmpliTaq Polymerase (Perkin Elmer):
Mix for Upper Reagent (Hotstart Protocol) (50 μl):
18.1 μl $H_2O$; 4.2 μl 10× buffer II; 16.7 μl dNTPs; 2.5 μl forward primer; 2.5 μl reverse primer; 6 μl 25 mM $MgCl_2$ (=1.5 mM).
Mix for Lower Reagent (50 μl):
42 μl, $H_2O$; 5 μl 10× buffer II; 1 μl AmpliTaq polymerase; 2 μl template.
DNA Purification
Purification of PCR reactions: The purification of PCR amplification products was carried out using the High Pure PCR Product Purification Kit (Roche)
Phenol extraction: Make up sample volume to 200 μl with TE buffer. Add 200 μl of phenol/chloroform/isoamyl alcohol (25:24:1), mix and spin for 1 minute at maximum speed. Transfer top phase into new Eppendorf tube, add 200 μl of chloroform/isoamyl alcohol, mix, spin for 1 minute. Remove top phase, then precipitate with ethanol.
Ethanol precipitation: To a sample volume of approx. 200 μl pipette 5 μl 5 M NaCl and 20 μl 3 M NaAc (pH 5.7). Add 2.5 volumes of 100% ethanol, mix, store for at least 30 minutes or longer at −20° C., spin for 10 minutes at 4° C., wash the pellet in 170 μl of 70% cold ethanol, spin for 3 minutes, and dry pellet at 37° C. and resuspend in 30 μl of $H_2O$.
Isolation of plasmid DNA from *E. coli*: The isolation of plasmid DNA from *E. coli* overnight cultures was carried out using the QIAprep Spin Miniprep Kit Protocol (Qiagen)
DNA Preparation from *Saccharomyces cerevisiae*:
Incubate the yeast cells overnight at 30° C. in 10 ml of YPD, in the morning: spin for 10 minutes at 3000 rpm, and resuspend pellet in 500 μl of 1 M sorbitol, 0.1 M EDTA (pH 7.5), and transfer into an Eppendorf tube. Add 50 μl of Zymolase (5 mg/ml, in sorbitol/EDTA), incubate for 1 hour at 37° C. and spin for 1 minute. Resuspend the pellet in 500 μl 50 mM Tris, 20 mM EDTA (pH 7.4). Add 50 μl 10% SDS, mix thoroughly and incubate for 30 minutes at 65° C., add 200 μl 5 M KAc, place on ice for 1 hour and spin for 10 minutes. Transfer the supernatant (approx. 650 μl) into a new Eppendorf tube, add 1 volume of isopropanol, mix gently and leave to stand for 5 minutes. Either spin down briefly or extract precipitated DNA with a glass hook and dry the pellet in the air. Resuspend the pellet or the DNA in 150 μl of TE buffer and dissolve for 10 minutes at 65° C.
DNA Cloning Techniques: All DNA Cloning Techniques were Carried out Following Standard Protocols.
Yeast Transformation (Lithium Acetate Method):
Incubate the yeast strain to be transformed overnight at 30° C. on the shaker in 5 ml of suitable medium; in the morning dilute the overnight culture with suitable medium ($OD_{600}$=0.4-0.5) and incubate for a further 2 hours on the shaker at 30° C. ($OD_{600}$=0.4-0.8). Spin for 3 minutes at 2500 rpm, wash pellet with 25 ml of sterile $H_2O$, spin for 3 minutes at 2500 rpm; resuspend pellet in 1 ml of LITE (100 mM LiAc, TE pH 7.5) and transfer suspension into an Eppendorf tube. Incubate for 5 minutes at RT, spin for 15 sec (Quickspin); wash pellet with 1 ml of 100 mM LiAc, quick-spin; depending on the cell density, resuspend pellet in 200-400 μl of 100 mM LiAc and divide into 50 μl aliquots.

Add the following in the exact sequence stated:

240 μl PEG (50%), mix suspension by gently pipetting

36 μl M LiAc, mix suspension by gently pipetting

10 μl ss-sperm DNA (stored at −20° C.; prior to use, heat for 10 minutes at 80-90° C., then transfer to ice)

2-3 μg plasmid DNA (or 8-10 μl of Miniprep in the case of knock-out transformation), mix suspension by gently pipetting Incubate transformation reaction for 30 minutes at 30° C. in an overhead rotator at slow speed Transformation reaction for 15 minutes at 42° C.

Quick-spin, resuspend pellet in 200 μl of TE buffer (in the case of knock-out:

resuspend pellet in 300 μl of YPD and incubate in an overhead rotator for 4 hours at 30° C.

Plate 100 μl per agar plate (in the case of knock-out of all of the reaction) and incubate for 3-4 days at 30° C.

Sequencing: ABI PRISM™red. protokoll/AmpliTaq® FS ¼ BIGDYE TERMINATOR

| Reaction: | |
|---|---|
| Premix | 2 μl |
| DNA template | |
| ss DNA | 50 ng |
| ds DNA | 250 ng |
| PCR products (0.2-5 kB) | 10-50 ng |
| Primer | 3-10 pmol |
| $H_2O$ to final volume | 10 μl |

Thermocycler Protocol (25 Cycles):
1. 15 seconds at 96° C.
2. 15 seconds at 96° C.
3. 10 seconds at 55° C.
4. 4 minutes at 60° C.
5. return to 2., 24×
6. 4° C. ∞
7. End.

Purification Reaction (Centri Sep Spin Columns, Princeton Separations):

Pre-soak column with 750 μl of $H_2O$ for 30 minutes; drain liquid; spin for 2 minutes at 3000 rpm; make up reaction to 20 μl with $H_2O$ and apply to column; spin for 2 minutes at 3000 rpm.

Sample application: in sequencing tubes, 4 μl of Centri Sep eluate+20 μl of TSR (template suppression reagent); denature for 2 minutes at 90° C.

Southern Blot:

Digest DNA probe with suitable restriction enzymes, separate by gel electrophoresis and extract from the gel. Digest genomic DNA overnight with suitable restriction enzymes and separate by gel electrophoresis (1% agarose gel)

Pretreatment of the gel: Remove loading wells from the agarose gel. Depurinate the agarose gel for 15 minutes in 0.25 M HCl, then wash 2× in distilled water; denature the agarose gel for 30 minutes in 0.5 M NaOH; transfer using the Vacuum Blotter Model 785 (BioRad): into the center of the vinyl sheet, cut a window (window seal), trim the edges of the nylon membrane and the filter paper in each case 0.5 cm smaller than the gel, moisten the edge of the nylon membrane with distilled water in each case 0.5 cm wider than the window in the vinyl sheet, then moisten nylon membrane and filter paper with transfer solution Construction of the Apparatus (Bottom to Top):

Base unit, vacuum platform, porous vacuum slab, filter paper, nylon membrane, vinyl window, agarose gel, final frame, lid Preheat BioRad vacuum pump for 10 minutes, apply vacuum (5 inches Hg)

Press gel gently along the edge

Place transfer solution (approx. 1 1 10×SSC) into upper reservoir; transfer time: 90 minutes; switch off vacuum, remove nylon membrane and rinse for 5 minutes in 2×SSC, then leave to dry in the air between filter paper. DNA immobilization: place nylon membrane on UV-permeable cling-film and apply probe at the edge as positive control; place into the STRATALINKER® UV CROSSLINKER and start crosslinking (1200000 J→0); membrane may be stored in cling-film or between Whatman filter paper at room temperature or 4° C.

Gene Images Random Prime Labelling Module (Amersham):

Labeling of the DNA probe: Denature DNA probe for 5 minutes at 96° C. (heat shock), then place on ice. 10 μl reaction mix (nucleotide mix (5×), fluorescein-11-dUTP, dATP, dCTP, dGTP and dTTP in Tris-HCl, pH 7.8, 2-mercaptoethanol and $MgCl_2$); 5 μl of primer (Random Nonamers); 1 μl of enzyme solution (Klenow fragment, 5 units/ml); 22 μl of denatured DNA probe; 12 μl of $H_2O$. Incubate for 2 hours at 37° C. and add 2 μl of 0.5 M EDTA (=20 mM), store aliquots at −20° C. Verification of the labeling efficiency: dilute 5× nucleotide mix with TE buffer 1/5, 1/10, 1/25, 1/50, 1/100, 1/250 and 1/500; to a nylon membrane strip, apply 5 μl of DNA probe together with 5 μl of 1/5 dilution, allow to absorb briefly and wash for 15 minutes at 60° C. in prewarmed 2×SSC; apply to a reference membrane strip the remaining solutions without the 1/5 dilution and observe both membrane strips under UV light→determination of the sample intensity.

Hybridization: Prehybridize nylon membrane (blot) with warmed hybridization buffer (0.3 ml/cm²) for 2 hours at 60° C. in a rotating oven; drain buffer and retain 10 ml thereof; denature DNA probe (20 μl); (5 minutes at 96° C., then cool on ice); place probe with the 10 ml of buffer onto blot and hybridize overnight at 60° C. in the rotating oven.

Wash Steps:

15 minutes on platform shaker in warmed 1×SSC, 0.1% (w/v) SDS; 15 minutes on a platform shaker in warmed 0.5× SSC, 0.1% (w/v) SDS Gene Images CDP-Star Detection Module (Amersham):

Stop and antibody reaction: On a shaker, incubate the blot at room temperature for 1 hour in a 1/10 dilution of stop reagent in buffer A; dilute antibody solution (alkaline phosphatase coupled to antifluorescein, 5000×) with 0.5% (w/v) BSA/buffer A, together with the blot seal into foil and incubate for 1 hour at room temperature on a shaker; remove unbound antibody solution by washing three times for 10 minutes in 0.3% Tween 10 in buffer A Signal generation and detection: Drain wash buffer, place blot on cling-film; apply 5 ml of detection reagent, allow to react for 2-5 minutes and again drain (the alkaline phosphatase causes the generation of light); wrap in cling-film and, in a dark room in red light, apply the film (Hyperfilm™ MP, Amersham), expose for 0.5 2 hours in a film cassette (BioMax, Kodak), develop and scan; the blot can be stored in cling-film at 4° C.

Example 1

Construction of the Specific Deletion Cassettes

All deletions were carried out by standard methods (Fink, G. R. et al., 1991; Wach, A. et al., 1994; Guldener, U. et al., 1996; Goldstein, A. L. et al., 1999).

Fragments of about 500 bp each, each of which represents the region at the beginning and the end of the gene, was amplified by PCR with the primers TRK1-FL-BamHI-Fo, TRK1-FL-PstI-Re, TRK1-FL-PstI-Fo and TRK1-FL-XhoI-Re for TRK1 or TRK2-DEL-5-Fo-B, TRK2-DEL-5-Re, TRK2-DEL-3-Fo and TRK2-DEL-3-Re for TRK2 and TOK1-DEL-5-Fo, TOK1-DEL-5-Re, TOK1-DEL-3-Fo and TOK1-DEL-3-Re for TOK1 (see Chapter 2.3). The amplified termini later allow correct integration into the yeast genome. The yeast strain w303 a/α or w303 a/α Δ trk1 acted as DNA template.

Example 2

Construction of the Single, Double and Triple Mutants

Example 2a

Single Knock-Out

The constructed deletion cassettes for TRK1, TRK2 and TOK1 were each transformed into the diploid yeast strain YM 96 (MATa/MATα). Integration of the deletion cassettes to the genome was verified by growing the trk1 mutants (YM123/124) on (−)URA/Glc and the trk2-(YM158-161) and tok1 mutants (YM154-157) on YPD/geniticin, since the URA3 marker in the TRK1 deletion cassette allows growth on (−)URA medium and the KAN marker in the TRK2 or TRK1 deletion cassette allows growth on geneticin (Fink, G. R. et al., 1991). The positive colonies were transferred to a sporulation plate by replica plating, whereupon MATa/MATα diploid cells sporulate after 18-24 hours without vegetative growth. After they were treated with Zymolase and regrown on YPD, tetrads of some colonies were then divided into 4 individual spores with the aid of a dissecting microscope.

The mating type of the spore colonies was determined by pairing with matching tester strains (Fink, G. R. et al., 1991). Selection for the presence of the deletion cassette was done by replica-plating on -URA medium (for trk1) and on geneticin-containing medium for trk2 and tok1. After obtaining the genomic DNA of the transformants by yeast DNA preparation, the result was verified by diagnostic PCR and Southern blot.

Example 2b

Double Knock-Out

The TOK1 deletion cassette was transformed into the haploid Δtrk1 yeast strains YM123 and Y124 and selected for integration of the TOK1 deletion cassette by growth on YPD/geneticin. The result was verified by diagnostic PCR and Southern blot. Glycerol cultures were made with the (+)URA3,(+)KAN (Δtrk1 Δtok1) strains (YM140, YM141, YM143 and YM144).

Single colonies were streaked out as patches, replica-plated on 5-FOA, and colonies ere selected which had eliminated the URA3 marker and a hisG repeat from the TRK1 deletion cassette (Fink, G. R. et al., 1991). Accordingly, no colonies which lacked the URA3 gene (in TRK1) for uracil synthesis grew on (−)URA/Glc, while all colonies survived on YPD/gen owing to the resistance gene in the TOK1 deletion cassette. To remove the Kan marker from the genome, the (−)URA3 mutants were transformed with plasmid pSH47, on which the genes for Cre recombinase and uracil synthesis (URA3) are located. Positive transformants grew on (−)URA/Glc and it was then possible to induce Cre recombinase by incubation in (−)URA/Gal liquid medium. In this process, the Kan marker together with one loxP repeat is eliminated, and one loxP remains.

After the overnight culture was brought to $OD_{600}=5$, the dilutions 1:10 000 and 1:50 000 were plated onto (−)URA/Gal. Patches of single colonies, replica-plated on YPD/gen, showed no growth (this means that the Kan marker had been eliminated successfully). To remove plasmid pSH47, the cells were subsequently reselected twice 5-FOA. Glycerol cultures were made with the (−)URA(−)KAN (Δtrk1 Δtok1) strains (YM162, YM163 and YM164).

Example 2c

Triple Knock-Out

Overnight cultures in YPD were set up with single Δtrk1 Δtok1 single colonies (YM162 and YM164), and, next day, transformed with the BsiWI/SpeI-digested TRK2 deletion cassette and plated onto YPD/KCl/geneticin. After a yeast DNA preparation, the triple knock-out was verified by diagnostic PCR and Southern blot.

TABLE 1

| Top row, left to right: | | Bottom row, left to right: | |
|---|---|---|---|
| 1. | marker | 1. | marker |
| 2. | YM 97 with TRK1 DiaFo/Re1 | 2. | YM 182 with TRK1 DiaFo/Re1 |
| 3. | YM 97 with TRK2 DiaFo/Re1 | 3. | YM 182 with TRK2 DiaFo/Re1 |
| 4. | YM 97 with TOK1 DiaFo/Re1 | 4. | YM 182 with TOK1 DiaFo/Re1 |
| 5. | YM 97 with TRK1 DiaFo/URARe | 5. | YM 182 with TRK1 DiaFo/URARe |
| 6. | YM 97 with TRK2 DiaFo/KANRe | 6. | YM 182 with TRK2 DiaFo/KANRe |
| 7. | YM 97 with TOK1 DiaFo/KANRe | 7. | YM 182 with TOK1 DiaFo/KANRe |
| 8. | free | 8. | free |
| 9. | YM 97 with TRK1 DiaFo/Re2 | 9. | YM 182 with TRK1 DiaFo/Re2 |
| 10. | YM 97 with TRK2 DiaFo/Re2 | 10. | YM 182 with TRK2 DiaFo/Re2 |
| 11. | YM 97 with TOK1 DiaFo/Re2 | 11. | YM 182 with TOK1 DiaFo/Re2 |

Example 3

Subcloning and Transformation of the Human Potassium Channels into the Double and Triple Mutants The human genes HERG, HCN2, Kv1.5 and, as positive controls, TRK1 and IRK1 (guinea pig) were excised from the plasmids harboring them (HERG between BamHI in pcDNA; HCN2 between NcoI/XhoI in PTLN; Kv1.5 between NheI/EcoRI in pcDNA3.1(−); IRK1 between BamHI/EcoRI in PSGEM) by cleavage with restriction enzymes, separated by gel electrophoresis and extracted from the gel. The individual human potassium channels were ligated into the yeast vector p423-GPD3 (Mumberg, D. et al., 1995; Ronicke, V. et al., 1997) and transformed into E. coli. Control digestion of the plasmid preparations and sequencing permitted the identification of the clones which had integrated the human gene.

The plasmids were subsequently transformed into the Δtrk1 Δtrk2 double knock-out (YM 168) and into the Δtrk1 Δtrk2 Δtok1 triple knock-out (YM 182) and plated onto (−)HIS/80 mM KCl.

Example 4

Characterization of the Knock-Out Strains

Example 4a

Growth of the Double and Triple Mutants on Culture Plates at Various $K^+$ Concentrations and pH Values To compare the potassium requirements of the various knockouts, yeast strains YM 182, YM 168 and YM 97 (WT) were incubated on DPM plates with different $K^+$ concentrations and different pH values. To this end, patches of the glycerol cultures were first streaked onto 100 mM KCl/pH 6.5. After 2 days' growth, 50 mM, 30 mM and 5 mM KCl were replica-plated.

This experiment showed that both strain YM168 (Δtrk1 Δtrk2) and strain YM182 (Δtrk1 Δtrk2 Δtok1) are viable on 50 mM and 30 mM KCl. Additionally, it emerged that strain YM182 grew better in the presence of 30 mM KCl than strain YM168. None of the two strains was viable in the presence of 5 mM KCl, in contrast to the wild-type strain YM97.

To test for pH dependency, the three strains were additionally replica-plated on 100 mM and 5 mM KCl/pH 5.0 and on 100 mM and 5 mM KCl/pH 4.0. This experiment demonstrated that neither YM168 nor YM182 are viable at pH 4.0 in the presence of 100 mM KCl and 5 mM KCl. At pH 5.0 and 100 mM KCl, the growth deficiency of YM168 is more pronounced than in the case of strain YM182. Expression of TRK1 of vector pRS416GAL1 fully compensates for the growth deficiency of strains YM168 (Δtrk1 Δtrk2) and YM182 (Δtrk1 Δtrk2 Δtok1).

Example 4b

Growth of Double and Triple Mutants in Liquid Medium at Various $K^+$ Concentrations To characterize strains YM168 (Δtrk1 Δtrk2) and YM182 (Δtrk1 Δtrk2 Δtok1), on which all further experiments are based, the growth behavior of the yeast strains in liquid culture was studied. First, overnight cultures were set up in DPM/80 mM KCl, and, next morning, the cultures were brought to an OD=0.05 with DPM/5 mM KCl and with DPM/15 mM KCl. The optical density at 600 nm was determined after defined intervals with the aid of a photometer.

These studies demonstrate that the growth deficiency of strain YM182 is less pronounced at 5 mM KCl and at 15 mM KCl than in the case of strain YM168.

Example 5

Characterization of the Human Potassium Channels in Double and Triple Knock-Outs

Example 5a

Complementation Capacity for $K^+$ Deficiency on Culture Plates

Each of the strains YM168 (Δtrk1 Δtrk2) and YM182 (Δtrk1 Δtrk2 Δtok1) was transformed with the human potassium channels Kv1.5 ((Fedida, D. et al., 1998);YM190 and YM195) and HERG1 ((Fedida, D. et al., 1998);YM191 and YM196) in p423-GPD3, respectively, as yeast expression vector. gpIRK1 ((Tang, W. et al., 1995);YM193 and YM198) acted as positive control in p423-GPD3 as yeast expression vector (Mumberg, D. et al., 1995; Ronicke, V. et al., 1997). The blank vector p423-GPD3 (YM189 and YM194) acted as negative control. The transformed yeast strains were plated onto (−)HIS/80 mM KCl medium. After this, patches of single colonies were replica-plated onto DPM/5 mM KCl (pH 6.5) to check the capacity of complementing he potassium deficiency.

These experiments demonstrated that the positive control gpIRK1 (YM193 and YM198) in p423-GPD3 fully complemented growth deficiency of double and triple knock-outs. The blank vector p423-GPD3 (YM189 and YM194) as negative control is not capable of complementing the growth deficiency. While the human potassium channel Kv1.5 complements the growth deficiency of triple knock-out, it does so significantly less effectively than the positive control gpIRK1. It was also observed that he human potassium channel Kv 1.5 does not complement the double knock-out Δtrk1 Δtrk2. Under the given experimental conditions, the HERG1 channel does not complement the growth deficiency of double and triple knock-outs.

Example 5b

Growth on Culture Plates in the Presence of Activators

To demonstrate the effect of activators on the various potassium channels, the strains stated above were incubated in media containing the following specific activators.

Kv1.5: $Rb^+$ extends the hyperpolarization phase. This means that the inwardly directed $K^+$ flux is more prolonged and increases the possibility of complementing the growth deficiency.

HERG: $Cs^+$ extends the hyperpolarization phase. This means that the inwardly directed $K^+$ flux is more prolonged and increases the possibility of complementing the growth deficiency. This channel is inhibited by $Cs^+$.

IRK1: $Cs^+$ blocks this channel.

The experiments with p423-GPD3-Kv1.5 demonstrated that the human Kv1.5 channel is capable of fully complementing the growth deficiency of the Δtrk1 Δtrk2 Δtok1 mutant in the presence of 2 mM RbCl (FIG. 3). Complementation of the growth deficiency of the Δtrk1 Δtrk2 mutant is markedly less effective (FIG. 3). This tallies with the results shown in Example 6a.

The experiments with p423-GPD3-HERG demonstrated that the human HERG1 channel is capable of fully complementing the growth deficiency of the Δtrk1 Δtrk2 tok1 mutant in the presence of 2 mM CsCl (FIG. 4). Complementation of the growth deficiency of the Δtrk1 Δtrk2 mutant is markedly less effective (FIG. 4). This tallies with the results shown in Example 6a.

Example 5c

Complementation by the Kv1.5 Channel in the Δtrk1 Δtrk2 Δtok1 Mutant in the Presence of RbCl in Liquid Medium The yeast strains YM 194 and YM 195 were tested in DPM/-HIS/5 mM KCl with 1 mM RbCl for the different growth behavior in liquid medium. To this end, 10 ml of overnight culture were set up in DPM/-HIS/80 mM KCl and, next morning, brought to an $OD_{600}$ of 0.05 with the relevant media (final volume: 20 ml). The optical density at 600 nm was determined at defined intervals with the aid of a photometer.

These experiments demonstrate unambiguously that the expression of Kv1.5 of vector p423-GPD3 in a yeast strain which is deleted for TRK1, TRK2 and TOK1 is capable of complementing the growth deficiency caused thereby.

In further experiments, it was demonstrated that the complementation of the growth deficiency by Kv1.5 and also by gpIRK1 is inhibited in the presence of 2 mM CsCl.

Example 5d

Complementation by the HERG1 Channel in the Δtrk1 Δtrk2 Δtok1 Mutant in the Presence of CsCl in Liquid Medium The yeast strains YM 194 and YM 196 were tested in DPM/-HIS/5 mM KCl with 1 mM CsCl for their different growth behavior in liquid medium. To this end, 10 ml of overnight culture were set up in DPM/-HIS/80 mM KCl and, next morning, brought to an $OD_{600}$ of 0.05 with the relevant media (final volume: 20 ml). The optical density at 600 nm was determined at defined intervals with the aid of a photometer. These experiments demonstrate unambiguously that the expression of HERG1 of vector p423-GPD3 in a yeast strain which is deleted for TRK1, TRK2 and TOK1 is capable of complementing the growth deficiency caused thereby.

Example 6

All growth assays in the triple mutant Δtrk1Δtrk2Δtok1 were carried out in growth medium DPM (defined potassium medium) at the pH and the potassium concentration stated in each case.

The substances employed as inhibitors of the human HERG1 $K^+$ channel were terfenadine (α-(4-tert-butylphenyl)-4-(α-hydroxy-aphenylbenzyl)-1-piperidinebutanol; HMR), pimozide (1-(4,4-bis(P-fluorophenyl)butyl)-4-(2-oxo-1-benzimidazolinyl)-piperidine; Sigma, Cat. No. P100), ziprasidone (5-(2-[4-(1,2-benzisothiazol-3-yl)piperazino]-ethyl)-6-chloro-1,3-dihydro-2H-indol-2-one; HMR), loratidine (ethyl 4-(8-chloro-5,6-dihydro-11H-benzo[5,6]cyclohepta[1,2-b]pyridin-11-ylidene)-1-piperidinecarboxylate; HMR) and sertindole (1-(2-[4-[5-chloro-1-(4-fluorophenyl)-1H-indol-3-yl]-1-piperidinyl]ethyl)-2-imidazolidinone; HMR) (Richelson, E. 1996; Richelson, E. 1999; Delpon, E. et al., 1999; Kobayashi, T. et al., 2000; Drici, M. D. et al., 2000). Diphenhydramine (Sigma, Cat. No. D3630) and fexofenadine (4-[hydroxy-4-[4-(hydroxydiphenylmethyl)-1-piperidinyl]butyl]-α,α-dimethyl benzeneacetic acid hydrochloride; HMR) (Taglialatela, M. et al., 1999; DuBuske, L. M. 1999), substances which should not have inhibitory effect on potassium channels, were also employed.

All substances, dissolved in DMSO, were employed in a final concentration of 30 µM. As a control, cells were measured with the same final concentration of 0.5% DMSO without substance, without DMSO addition or without substance.

As described in FIGS. 1 and 2, the human HERG1 channel is capable of complementing the growth deficiency of the triple mutant Δtrk1Δtrk2Δtok1 on medium which only contains 5 mM KCl. It was possible to demonstrate (FIG. 7, FIG. 8) that, in the presence of the substances terfenadine, pimozide, ziprasidone, sertindole and loratadine, the human HERG1 channel can no longer complement the growth deficiency of the triple mutant Δtrk1Δtrk2Δtok1 on medium which only contains 5 mM KCl.

Example 7

Incubation with the substances terfenadine, pimozide, diphenhydramine, ziprasidone, loratidine, fexofenadine and sertindole of the wild-type strain which expresses all three endogenous potassium channel proteins of yeast demonstrated that terfenadine, loratidine and sertindole are specific inhibitors of the human HERG1 channel (FIG. 9).

According to the present results, pimozide and ziprasidone must be considered as rather unspecific inhibitors. This means that these substances possibly inhibit not only the human HERG1 channel, but also the endogenous potassium channels of the yeast Saccharomyces cerevisiae. However, the present results could not exclude that the inhibitory effect found for these substances can possibly also be attributed to an inhibition of other proteins which are essential for the growth of yeast cells. To study this possibility, the action of these substances was also tested in a growth medium containing 80 mM KCl.

These studies demonstrated (FIG. 10) that pimozide inhibits the activity of the essential endogenous potassium channels TRK1 and TRK2 in an unspecific fashion.

The absence of an inhibitory effect of higher potassium concentrations allows the conclusion that pimozide has no generally toxic effect on yeast cells. In contrast, it was demonstrated that ziprasidone inhibits the growth of the yeast cells even at higher potassium concentrations and therefore has a toxic effect on Saccharomyces cerevisiae. The identification of the target protein in the yeast which might be responsible for this effect is as yet outstanding.

In conclusion, these experiments demonstrate that the above-described system makes it possible in practice to identify, in the yeast Saccharomyces cerevisiae, substances which specifically inhibit the human potassium channels.

The results can be seen from FIG. 10.

Example 8

The human potassium channels HERG1 and Kv1.5 do not complement the growth deficiency of the double mutant Δtrk1Δtrk2 (FIG. 11 and FIG. 12).

Results: FIGS. 11 and 12.

FIGS. 11 and 12 demonstrate that the human potassium channels HERG1 and Kv1.5 do not complement the growth deficiency of the double mutantΔtrk1Δtrk2 (in each case 4th segment in FIGS. 11 and 12). The comparison with the negative control, i.e. the blank vector üp423GPD in the triple mutant Δtrk1Δtrk2Δtok1 (in each case 1st segment of FIGS. 11 and 12), shows no improved growth. The negative control p423GPD in the double mutant Δtrk1Δtrk2 is not shown, but does not differ from the negative control p423GPD in the triple mutant Δtrk1Δtrk2Δtok1. In contrast, the human potassium channels HERG1 and Kv1.5 complement the growth deficiency of the triple mutant Δtrk1Δtrk2Δtok1 (in each case 3rd segment of FIGS. 11 and 12).

Example 9

The human potassium channel ROMK2 ((Shuck, M. E. et al., 1994; Bock, J. H. et al., 1997); Sequence SEQ ID NO.7 hROMK2) was subcloned into the yeast vector p423GPD and transformed into the triple mutant Δtrk1Δtrk2Δtok1. The studies demonstrated that this human potassium channel too is capable of complementing the growth deficiency of the triple mutant Δtrk1Δtrk2Δtok1.

The capability of this human potassium channel to complement the growth deficiency of the double mutant Δtrk1Δtrk2 has not been studied as yet. No substances are known as yet which specifically inhibit the ROMK2 channel.

The results can be seen from FIG. 13.

REFERENCES

Curran, M. E., Landes, G. M., and Keating, M. T. Molecular cloning, characterization, and genomic localization of a human potassium channel gene. *Genomics* 12: 729-737. (1992)

Dascal, N., Schreibmayer, W., Lim, N. F., Wang, W., Chavkin, C., DiMagno, L., Labarca, C., Kieffer, B. L., Gaveriaux-Ruff, C., and Trollinger, D. Atrial G protein-activated K+ channel: expression cloning and molecular properties. *Proc. Natl. Acad. Sci. U.S.A.* 90: 10235-10239. (1993)

Fairman, C., Zhou, X., and Kung, C. Potassium uptake through the TOK1 K+ channel in the budding yeast. *J. Membr. Biol.* 168: 149-157. (1999)

Fedida, D., Chen, F. S., and Zhang, X. The 1997 Stevenson Award Lecture. Cardiac K+ channel gating: cloned delayed rectifier mechanisms and drug modulation. *Can. J. Physiol. Pharmacol.* 76: 77-89. (1998)

Fink, G. R. and Guthrie, C. Guide to Yeast Genetics and Molecular Biology. Guthrie, C. and Fink, G. R. (194). 1991. Academic Presss, Inc. Methods in Enzymology. Ref Type: Book, Whole Gaber, R. F., Styles, C. A., and Fink, G. R. TRK1 encodes a plasma membrane protein required for high-affinity potassium transport in *Saccharomyces cerevisiae*. *Mol. Cell Biol.* 8: 2848-2859. (1988)

Goldstein, A. L. and McCusker, J. H. Three new dominant drug resistance cassettes for gene disruption in *Saccharomyces cerevisiae* [In Process Citation] *Yeast.* 15: 1541-1553. (1999)

Goldstein, S. A., Price, L. A., Rosenthal, D. N., and Pausch, M. H. ORK1, a potassium-selective leak channel with two pore domains cloned from *Drosophila melanogaster* by expression in *Saccharomyces cerevisiae* [published erratum appears in Proc Natl Acad Sci USA 1999 Jan. 5, 1999; 96(1): 318] *Proc. Natl. Acad. Sci. U.S.A.* 93: 13256-13261. (1996)

Guldener, U., Heck, S., Fielder, T., Beinhauer, J., and Hegemann, J. H. A new efficient gene disruption cassette for repeated use in budding yeast. *Nucleic. Acids. Res.* 24: 2519-2524. (1996)

Ikeda, K., Kobayashi, K., Kobayashi, T., Ichikawa, T., Kumanishi, T., Kishida, H., Yano, R., and Manabe, T. Functional coupling of the nociceptin/orphanin FQ receptor with the G-protein-activated K+ (GIRK) channel. *Brain Res. Mol. Brain Res.* 45: 117-126. (1997)

Itoh, T., Tanaka, T., Nagai, R., Kamiya, T., Sawayama, T., Nakayama, T., Tomoike, H., Sakurada, H., Yazaki, Y., and Nakamura, Y. Genomic organization and mutational analysis of HERG, a gene responsible for familial long QT syndrome. *Hum. Genet.* 102: 435-439. (1998)

Jan, L. Y. and Jan, Y. N. Cloned potassium channels from eukaryotes and prokaryotes. *Annu. Rev. Neurosci.* 20:91-123: 91-123. (1997)

Jelacic, T. M., Sims, S. M., and Clapham, D. E. Functional expression and characterization of G-protein-gated inwardly rectifying K+ channels containing GIRK3. *J. Membr. Biol.* 169: 123-129. (1999)

Ketchum, K. A., Joiner, W. J., Sellers, A. J., Kaczmarek, L. K., and Goldstein, S. A. A new family of outwardly rectifying potassium channel proteins with two pore domains in tandem. *Nature* 376: 690-695. (1995)

Ko, C. H., Buckley, A. M., and Gaber, R. F. TRK2 is required for low affinity K+ . *J. Biol. Chem.* 273: 14838-14844. (1998)

Main, M. J., Brown, J., Brown, S., Fraser, N.J., and Foord, S. M. The CGRP receptor can couple via pertussis toxin transport in *Saccharomyces cerevisiae*. *Genetics* 125: 305-312. (1990)

Ko, C. H. and Gaber, R. F. TRK1 and TRK2 encode structurally related K+ transporters in *Saccharomyces cerevisiae*. *Mol. Cell Biol.* 11: 4266-4273. (1991)

Kubo, Y., Reuveny, E., Slesinger, P. A., Jan, Y. N., and Jan, L. Y. Primary structure and functional expression of a rat G-protein-coupled muscarinic potassium channel [see comments] *Nature* 364: 802-806. (1993)

Ludwig, A., Zong, X., Stieber, J., Hullin, R., Hofmann, F., and Biel, M. Two pacemaker channels from human heart with profoundly different activation kinetics. *EMBO J.* 18: 2323-2329. (1999)

Madrid, R., Gomez, M. J., Ramos, J., and Rodriguez-Navarro, A. Ectopic potassium uptake in trk1 trk2 mutants of *Saccharomyces cerevisiae* correlates with a highly hyperpolarized membrane potentialsensitive and insensitive G proteins. *FEBS Lett.* 441: 6-10. (1998)

Mumberg, D., Muller, R., and Funk, M. Yeast vectors for the controlled expression of heterologous proteins in different genetic backgrounds. *Gene* 156: 119-122. (1995)

Myers, A. M., Pape, L. K., and Tzagoloff, A. Mitochondrial protein synthesis is required for maintenance of intact mitochondrial genomes in *Saccharomyces cerevisiae*. *EMBO J.* 4: 2087-2092. (1985)

Nakamura, R. L., Anderson, J. A., and Gaber, R. F. Determination of key structural requirements of a K+ channel pore. *J. Biol. Chem.* 272: 1011-1018. (1997)

Roberds, S. L. and Tamkun, M. M. Cloning and tissue-specific expression of five voltage-gated potassium channel cDNAs expressed in rat heart. *Proc. Natl. Acad. Sci. U.S.A.* 88: 1798-1802. (1991)

Ronicke, V., Graulich, W., Mumberg, D., Muller, R., and Funk, M. Use of conditional promoters for expression of heterologous proteins in *Saccharomyces cerevisiae*. *Methods Enzymol.* 283:313-22: 313-322. (1997)

Sanguinetti, M. C. and Zou, A. Molecular physiology of cardiac delayed rectifier K+ channels. *Heart Vessels* Suppl 12: 170-172. (1997)

Schreibmayer, W., Dessauer, C. W., Vorobiov, D., Gilman, A. G., Lester, H. A., Davidson, N., and Dascal, N. Inhibition of an inwardly rectifying K+ channel by G-protein alpha-subunits. *Nature* 380: 624-627. (1996)

Smith, F. W., Ealing, P. M., Hawkesford, M. J., and Clarkson, D. T. Plant members of a family of sulfate transporters reveal functional subtypes. *Proc. Natl. Acad. Sci. U.S.A.* 92: 9373-9377. (1995)

Snyders, D. J., Tamkun, M. M., and Bennett, P. B. A rapidly activating and slowly inactivating potassium channel cloned from human heart. Functional analysis after stable mammalian cell culture expression. *J. Gen. Physiol.* 101: 513-543. (1993)

Taglialatela, M., Castaldo, P., Pannaccione, A., Giorgio, G., and Annunziato, L. Human ether-a-gogo related gene (HERG) K+ channels as pharmacological targets: present and future implications. *Biochem. Pharmacol.* 55:1741-1746. (1998)

Tang, W., Ruknudin, A., Yang, W. P., Shaw, S. Y., Knickerbocker, A., and Kurtz, S. Functional expression of a vertebrate inwardly rectifying K+ channel in yeast. *Mol. Biol. Cell* 6: 1231-1240. (1995)

Wach, A., Brachat, A., Pohlmann, R., and Philippsen, P. New heterologous modules for classical or PCR-based gene disruptions in *Saccharomyces cerevisiae*. *Yeast.* 10: 1793-1808. (1994)

Wang, Q., Chen, Q., and Towbin, J. A. Genetics, molecular mechanisms and management of long QT syndrome. *Ann. Med.* 30: 58-65. (1998)

Wilde, A. A. and Veldkamp, M. W. Ion channels, the QT interval, and arrhythmias. *Pacing. Clin. Electrophysiol.* 20: 2048-2051. (1997)

Wischmeyer, E., Doring, F., Spauschus, A., Thomzig, A., Veh, R., and Karschin, A. Subunit interactions in the assembly of neuronal Kir3.0 inwardly rectifying K+ channels. *Mol. Cell Neurosci.* 9:194-206. (1997)

Yamada, M., Inanobe, A., and Kurachi, Y. G protein regulation of potassium ion channels. *Pharmacol. Rev.* 50: 723-760. (1998)

Bock, J. H., Shuck, M. E., Benjamin, C. W., Chee, M., Bienkowski, M. J., and Slightom, J. L. Nucleotide sequence analysis of the human KCNJ1 potassium channel locus *Gene* 188: 9-16. (1997)

Delpon, E., Valenzuela, C., and Tamargo, J. Blockade of cardiac potassium and other channels by antihistamines *Drug Saf* 21 Suppl 1:11-8; discussion 81-7: 11-18. (1999)

Drici, M. D. and Barhanin, J. Cardiac K+ channels and drug-acquired long QT syndrome *Therapie* 55: 185-193. (2000)

DuBuske, L. M. Second-generation antihistamines: the risk of ventricular arrhythmias *Clin. Ther.* 21:281-295. (1999)

Itoh, T., Tanaka, T., Nagai, R., Kikuchi, K., Ogawa, S., Okada, S., Yamagata, S., Yano, K., Yazaki, Y., and Nakamura, Y. Genomic organization and mutational analysis of KVLQT1, a gene responsible for familial long QT syndrome *Hum. Genet.* 103: 290-294. (1998)

Kobayashi, T., Ikeda, K., and Kumanishi, T. Inhibition by various antipsychotic drugs of the G-protein-activated inwardly rectifying K(+) (GIRK) channels expressed in *Xenopus* oocytes *Br. J. Pharmacol.* 129: 1716-1722. (2000)

Richelson, E. Preclinical pharmacology of neuroleptics: focus on new generation compounds *J. Clin. Psychiatry* 57 Suppl 11:4-11: 4-11. (1996)

Richelson, E. Receptor pharmacology of neuroleptics: relation to clinical effects [see comments] *J. Clin. Psychiatry* 60 Suppl 10:5-14: 5-14. (1999)

Shuck, M. E., Bock, J. H., Benjamin, C. W., Tsai, T. D., Lee, K. S., Slightom, J. L., and Bienkowski, M. J. Cloning and characterization of multiple forms of the human kidney ROM-K potassium channel *J. Biol. Chem.* 269: 24261-24270. (1994)

Taglialatela, M., Castaldo, P., Pannaccione, A., Giorgio, G., Genovese, A., Marone, G., and Annunziato, L. Cardiac ion channels and antihistamines: possible mechanisms of cardiotoxicity *Clin. Exp. Allergy* 29 Suppl 3:182-9: 182-189. (1999)

TABLE 1

Nucleotide sequence of TRK1

SEQ ID. NO. 1

ATGCATTTTAGAAGAACGATGAGTAGAGTGCCCACATTGGCATCTCTTGAAATACGATATAAAAAATCTTTCGGCC

ATAAATTTCGTGATTTTATTGCTCTATGTGGTCACTATTTTGCTCCAGTTAAAAAATATATCTTCCCCAGTTTTAT

CGCGGTTCACTACTTCTACACGATATCCCTGACATTAATAACTTCAATCCTGCTATATCCCATTAAGAATACCAGA

TACATTGATACATTGTTTTTAGCAGCGGGCGCAGTTACACAAGGTGGCTTAAATACTGTGGATATCAACAATCTAA

GCTTATACCAACAAATTGTTCTGTATATCGTATGCTGCATATCAACACCAATTGCAGTTCATAGTTGCTTGGCATT

TGTACGGCTTTACTGGTTTGAGCGCTACTTCGATGGTATTAGAGACTCTTCTAGACGAATTTTAAAGATGAGAAGA

ACGAAAACAATCTTAGAAAGGGAACTAACAGCAAGAACCATGACCAAGAATAGAACAGGTACCCAAAGAACGTCTT

ATCCTAGGAAACAAGCTAAAACAGATGATTTCCAAGAAAAATTGTTCAGCGGAGAAATGGTTAATAGAGATGAGCA

GGACTCAGTTCACAGCGACCAGAATTCTCATGACATTAGTAGGGACAGCAGCAATAATAATACGAATCACAATGGT

AGCAGTGGCAGTTTAGATGATTTCGTTAAGGAAGACGAAACGGATGACAATGGAGAATATCAGGAGAACAACTCCT

ACTCGACGGTAGGTAGTTCGTCTAACACAGTTGCAGACGAAAGTTTAAATCAGAAGCCCAAGCCAAGCAGTCTTCG

GTTTGATGAGCCACACAGCAAACAAAGACCCGCAAGAGTTCCCTCAGAGAAATTTGCAAAAAGAAGGGGTTCAAGA

GATATTAGCCCAGCCGATATGTATCGATCCATTATGATGCTACAAGGTAAGCATGAAGCAACTGCTGAAGATGAAG

GTCCCCCTTTAGTCATCGGGTCCCCTGCGGATGGCACAAGATATAAAAGTAATGTCAATAAGCTAAAGAAGGCCAC

CGGCATAAATGGTAACAAAATCAAGATTCGAGATAAGGGAAATGAAAGTAACACTGATCAAAATTCCGTGTCAAGT

GAAGCAAACAGTACGGCGAGCGTTTCGGACGAAAGCTCGTTACACCAAAATTTTGGTAACAAAGTACCTTCATTAA

GAACAAATACTCATAGATCAAATTCGGGCCCGATAGCCATTACTGATAACGCAGAAACAGACAAAAAGCATGGGCC

ATCAATTCAATTCGATATAACTAAACCTCCTAGAAAAATTTCAAAAAGAGTTTCAACCTTCGATGATTTGAACCCA

AAATCTTCCGTTCTTTATCGAAAAAAAGCATCGAAGAAGTACCTCATGAAAACATTTTCCTAAGCGCGGCGAATAC

GGCAACAAATTAAGAGAAGGCTTTCTACTGGTTCAATTGAGAAAAACAGCAGTAACAATGTTTCAGATAGAAACC

TATTACTGATATGGATGATGATGATGATGACGATGACAACGACGGCGATAACAACGAAGAATACTTTGCTGACAAC

TABLE 1-continued

Nucleotide sequence of TRK1

GAAAGCGGCGATGAAGATGAACGAGTACAGCAGTCTGAACCACATTCTGATTCAGAACTCAAATCGCACCAACAAC

AGCAAGAAAAACACCAACTGCAGCAGAACCTGCACCGCATGTATAAAACCAAATCATTTGATGATAATCGTTCAAG

AGCAGTTCCTATGGAACGTTCCAGGACCATCGATATGGCAGAGGCTAAGGATCTAAATGAGCTCGCAAGGACGCCT

GATTTTCAAAAAATGGTCTATCAAAATTGGAAAGCCCATCATAGAAAAAACCGAACTTTAGGAAGAGGGGATGGA

ATAACAAGATATTTGAACATGGTCCCTATGCATCTGACAGCGATCGCAATTATCCTGATAATAGTAATACTGGAAA

CAGTATTCTTCATTACGCAGAGTCTATTTTACATCATGATGGCTCTCATAAAAATGGAAGCGAAGAAGCCTCTTCC

GACTCTAATGAGAATATCTATTCCACGAATGGAGGAAGCGACCACAATGGTCTTAACAACTATCCTACTTACAACG

ACGATGAAGAAGGCTATTATGGTTTACATTTCGATACCGATTATGACCTAGATCCTCGTCATGATTTATCTAAAGG

CAGTGGTAAACGTATCTATCATGGCAACCAACTATTGGACGTAAACTCAAACTTCCTTGGATTAACAAGAGCCCAG

AAAGATGAATTAGGTGGTGTCGAGTACAGAGCAATCAAACTTTTATGCACCATATTGGTTGTCTACTACGTTGGAT

GGCATATTGTTGCTTTTGTTATGTTAGTACCTTGGATTATTTTGAAAAAGCATTATAGTGAAGTTGTTAGAGATGA

TGGTGTTTCACCTACATGGTGGGATTTTGGACAGCAATGAGTGCATTTAATGATTTAGGTTTGACATTAACTCCA

AATTCAATGATGTCGTTTAACAAAGCTGTATACCCATTGATCGTTATGATTTGGTTTATCATTATCGGAAATACAG

GGTTTCCCATCCTTCTTAGATGCATCATTTGGATAATGTTTAAAATTTCTCCTGATTTATCACAGATGAGAGAAAG

TTTAGGTTTTCTCTTAGACCATCCACGTCGTTGTTTCACCTTGCTATTTCCTAAGGCAGCTACATGGTGGCTACTT

TTAACGCTTGCAGGATTGAATATAACTGATTGGATTTTATTTATTATTCTAGATTTTGGCTCAACAGTTGTGAAAT

CATTATCGAAAGGCTATAGAGTCCTTGTCGGCCTGTTTCAATCTGTTAGCACAAGAACTGCTGGATTCAGCGTTGT

CGATTTAAGTCAACTGCATCCTTCTATCCAAGTCTCCTATATGCTAATGATGTATGTCTCCGTATTACCATTGGCC

ATCTCTATTCGACGGACAAATGTTTACGAGGAGCAATCTTTAGGACTATATGGAGATATGGGGGGAGAACCAGAAG

ATACGGATACTGAAGACGATGGTAACGATGAAGATGACGACGAGGAAAACGAGAGTCACGAAGGTCAAAGTAGTCA

AAGAAGTAGTTGAACAACAACAACAATAACAACAGGAAAAAGAAAAAGAAAAAGAAAACTGAAAATCCAAATGAA

ATATCTACAAAATCCTTTATCGGTGCCCATTTAAGGAAACAGCTTTCATTTGACTTGTGGTTTCTATTTTTAGGGT

TATTTATCATTTGCATTTGTGAAGGGGACAAGATAAAGGACGTACAAGAACCAAACTTTAATATATTTGCAATTCT

TTTTGAAATTGTTAGCGCTTACGGTACAGTTGGGCTATCGCTAGGTTATCCGGACACCAACCAATCGTTTTCAAGA

CAGTTTACTACATTATCTAAGTTGGTGATCATAGCTATGCTGATCAGAGGCAAGAATAGAGGTCTACCATACTCAC

TGGATCGTGCAATTATCTTGCCTAGTGATAGACTTGAACATATTGACCACCTTGAGGGCATGAAATTGAAGAGACA

GGCTAGAACCAATACAGAAGACCCAATGACGGAACATTTCAAGAGAAGTTTCACTGATGTGAAACATCGTTGGGGA

GCTCTTAAGCGTAAGACCACACATTCCCGAAATCCTAAAAGGAGCAGCACAACGCTCTAA

TABLE 2

Nucleotide sequence of TRK2

SEQ ID. NO. 2
ATGCCAACAGCTAAGAGGACGTCATCCAGGGCTTCGTTGGCACTGCCCTTCCAGTTACGGTTGGTGCACAAGAAAT

CATGGGGCCATCGGCTAAGAGACTTCATTTCCGGGTTCTTAAAATCATGCAGACCCATTGCTAAATACGTTTTCCC

CAACTTCATCGTGGTGCACTATATCTACCTGATCACGCTGTCGATTATCGGGTCCATTCGTTATATCCGTGCAAG

AACACGGCGTTCATCGATGTGCTATTTCTGGCTGCTGGAGCGTCTACACAGGGCGGGCTGGCCACCAAGAGCACTA

ACGATTTCAACCTGTACCAGCAGATAGTGGTGTACGTCATTACATTGCTGTCCACGCCTATACTTATTCATGGGTT

TTTGGCCTTTGTCAGGCTGTATTGGTTTGAAAGGTACTTCGACAACATTAGGGATATCTCCAACAGAATTTTAAAA

TABLE 2-continued

Nucleotide sequence of TRK2

CTAAGAAGGACCATGACGTTGCAACAAAGGGAACTATCGGGCAGCAGTGGCAATGCCGCTCGAAGTAGGAGTTTCA
AGGACAACCTGTTCCGTGGGAAGTTTGTTTCCAGAGAAGACCCACGACAATCCGCTTCAGATGTGCCGATGGACTC
TCCTGACACGTCCGCATTGTCCTCAATCTCACCGTTGAATGTTTCCTCCTCTAAGGAGGAATCCAGTGACACGCAA
AGCTCGCCTCCAAACTTCTCAAGTAAGCGCCAACCCTCAGACGTTGACCCAAGAGACATTTACAAATCGATAATGA
TGCTACAAAACAACAAGAGAAGAGCAACGCAAACTCCACGGATTCTTTTTCGAGCGAGACCAATGGACCCGCTTT
CATTGTGCAGGAACGTCATGAGAGAAGAGCCCCCCACTGCTCACTGAAACGCCATTCTGTCCTGCCATCTTCTCAG
GAATTGAACAAGCTAGCCCAGACGAAAAGTTTCCAGAAATTGCTTGGCTTGCGGAGAGATGAAGGTGACCATGACT
ACTTTGACGGTGCTCCTCACAAATATATGGTCACCAAGAAGAAAAAAATATCTAGAACGCAATCATGTAACATCCC
AACGTATACTGCTTCACCGAGTCCTAAAACCTCAGGCCAAGTAGTTGAAAATCATAGAAACTTGGCCAAGTCGGCG
CCTTCATCTTTTGTTGATGAGGAGATGAGCTTTTCACCGCAAGAGTCTTTGAATTTACAGTTCCAAGCGCACCCGC
CCAAACCAAAACGACGTGAAGGTGATATAGGCCACCCCTTCACCAGAACAATGAGCACCAACTATCTATCGTGGCA
GCCAACCTTTGGCAGAAACTCCGTCTTCATTGGACTCACAAAGCAACAAAAGGAGGAACTCGGCGGTGTCGAATAT
CGTGCTTTGAGATTGCTGTGCTGCATTCTCATGGTATACTACATCGGATTCAACATTTTGGCGTTTGTGACCATCG
TTCCATGGGCCTGTACGAGGCACCACTACTCAGAGATTATTAGACGAAATGGAGTTTCTCCAACCTGGTGGGGGTT
TTTCACTGCAATGAGTGCATTCAGCAACTTGGGTCTGTCTTTGACCGCTGATTCAATGGTTTCCTTTGATACTGCG
CCGTATCCGCTGATTTTCATGATGTTCTTCATCATCATAGGCAATACAGGCTTCCCAATTATGTTACGATTTATCA
TTTGGATCATGTTCAAGACCTCGAGAGACCTATCTCAGTTTAAGGAAAGTCTTGGGTTTCTCTTGGATCATCCGCG
CAGGTGTTTTACGTTGCTGTTCCCCAGCGGCCCCACATGGTGGCTGTTTACAACTTTAGTCGTCTTAAACGCTACG
GATTGGATTCTTTTCATAATTCTGGATTTCAACTCCGCTGTAGTAAGGCAGGTTGCTAAAGGTTATCGAGCTCTCA
TGGGCCTCTTCCAGTCTGTATGCACAAGAACTGCTGGATTCAACGTTGTTGACTTAAGTAAATTACACCCGTCCAT
TCAGGTGTCTTATATGCTAATGATGTACGTTTCGGTCCTGCCGCTGGCGATTTCCATTAGAAGAACGAATGTTTAT
GAGGAGCAATCGTTGGGACTATACGATAGTGGACAAGATGACGAAAATATCACCCACGAAGACGATATAAAGGAAA
CAGACCATGATGGCGAATCCGAAGAGCGAGACACTGTATCTACAAAGTCCAAGCCGAAGAAACAGTCCCCAAAATC
GTTTGTTGGTGCTCATTTGAGGAGGCAACTCTCTTTTGATTTATGGTACCTATTCCTTGGATTATTTATAATATGC
ATATGCGAGGGCAGAAAAATCGAAGACGTTAATAAACCTGATTTCAATGTCTTTGCTATATTGTTTGAAGTTGTTA
GCGCTTATGGTACAGTGGGTTTGTCATTGGGTTACCCAAACACCAACACATCACTATCTGCCCAGTTCACCGTATT
ATCGAAGCTAGTCATAATTGCCATGCTAATAAGAGGAAGAAATAGAGGTTTACCATACACTTTGGATCGTGCCATC
ATGCTGCCAAGTGACAAACTGGAACAAATTGATCGTTTACAAGATATGAAAGCTAAGGGTAAGTTGTTAGCCAAAG
TTGGTGAGGATCCAATGACTACTTACGTCAAAAAGAGATCCCACAAACTGAAAAAAATAGCAACAAAGTTTTGGGG
GAAGCATTA

TABLE 3

Nucleotide sequence of TOK1

SEQ ID NO. 3
ATGACAAGGTTCATGAACAGCTTTGCCAAACAAACGCTGGGATATGGCAATATGGCGACAGTGGAGCAAGAGAGCT
CAGCTCAGGCTGTTGATTCTCATTCAAACAACACACCGAAGCAAGCTAAGGGTGTTCTTGCAGAGGAACTAAAGGA
TGCATTGCGGTTCCGGGACGAAAGAGTTAGTATTATTAATGCAGAGCCTTCTTCAACACTGTTCGTCTTTTGGTTT
GTGGTTTCATGCTATTTCCCTGTGATTACTGCCTGCTTGGGTCCCGTAGCTAACACTATCTCGATAGCCTGTGTAG
TTGAAAAATGGAGATCCTTAAAGAACAACTCCGTGGTGACAAATCCACGAAGCAATGACACCGATGTTTTGATGAA

TABLE 3-continued

| Nucleotide sequence of TOK1 |
|---|

```
TCAAGTAAAGACAGTTTTTGATCCTCCTGGTATTTTTGCCGTTAATATCATCTCTTTGGTACTGGGTTTTACGTCA
AATATTATACTAATGCTACATTTCAGTAAGAAGTTGACGTATCTTAAATCTCAGTTAATAAATATAACAGGATGGA
CAATAGCTGGAGGGATGCTTTTGGTGGACGTGATTGTATGCTCCTTGAATGACATGCCCAGCATCTACAGTAAGAC
TATCGGATTTTGGTTTGCCTGTATCAGTTCTGGTCTATATTTGGTATGCACCATTATTTTAACAATACATTTTATT
GGATATAAATTAGGAAAATATCCTCCAACGTTCAACCTTTTGCCCAATGAAAGAAGTATCATGGCATACACTGTAC
TATTGTCTTTATGGTTGATTTGGGGTGCGGGTATGTTTAGCGGTTTATTGCACATCACTTACGGAAATGCATTATA
TTTCTGCACGGTATCATTATTAACCGTGGGACTAGGTGACATCCTGCCCAAGTCGGTTGGCGCCAAAATCATGGTT
TTAATCTTTTCGCTATCTGGTGTTGTCTTGATGGGTTTAATAGTGTTTATGACAAGATCCATCATTCAAAGTCCT
CTGGCCCAATTTTCTTTTTCCACAGAGTTGAAAAAGGCAGGTCCAAATCGTGGAAACATTATATGGATAGTAGTAA
AAATTTATCTGAAAGGGAAGCGTTCGACTTAATGAAGTGTATCCGACAAACGGCCTCAAGGAAGCAGCATTGGTTT
TCTTTGTCGGTGACTATTGCAATTTTCATGGCTTTTTGGTTATTGGGAGCTCTTGTATTCAAATTCGCAGAAAATT
GGTCGTACTTCAATTGTATTTACTTTTGTTTCTTGTGCTTATTAACCATTGGATACGGAGACTATGCTCCAAGGAC
TGGTGCAGGCCGTGCTTTTTTTGTGATTTGGGCGTTGGGAGCCGTGCCATTAATGGGGGCTATCCTATCTACAGTC
GGTGATCTGTTGTTTGACATTTCCACTTCTCTGGATATTAAGATCGGTGAATCATTCAATAATAAAGTCAAGTCCA
TCGTTTTTAATGGGCGTCAAAGAGCACTTTCCTTTATGGTGAACACTGGAGAAATTTTCGAAGAATCTGACACAGC
TGATGGTGATCTGGAAGAAAATACAACGAGCTCACAATCCAGTCAAATTTCTGAATTCAACGATAATAATTCAGAA
GAGAATGATTCTGGAGTGACATCCCCTCCTGCAAGCCTGCAAGAATCATTTTCTTCATTATCAAAAGCATCTAGCC
CAGAGGGAATACTTCCTCTAGAATATGTTTCTTCTGCTGAATATGCACTACAGGACTCGGGGACCTGTAATTTAAG
GAACTTGCAAGAGCTACTTAAAGCCGTCAAAAAACTACATCGGATATGTCTGGCGGATAAAGATTACACACTTAGT
TTTTCCGACTGGTCGTACATTCATAAACTACATTTGAGGAACATTACAGATATTGAGGAGTACACACGCGGACCCG
AATTTTGGATATCACCTGATACGCCCCTCAAGTTCCCGTTAAATGAACCTCATTTTGCTTTTATGATGCTTTTCAA
GAACATAGAAGAATTAGTTGGTAATCTAGTAGAAGACGAAGAGCTTTATAAAGTTATAAGCAAAAGAAAATTTTTG
GGTGAGCATAGAAAGACACTTTGA
```

TABLE 4

| Nucleotide sequence of HERG1 |
|---|

SEQ ID NO.4
```
ATGCCGGTGCGGAGGGGCCACGTCGCGCCGCAGAACACCTTCCTGGACACCATCATCCGCAAGTTTGAGGGCCAGA
GCCGTAAGTTCATCATCGCCAACGCTCGGGTGGAGAACTGCGCCGTCATCTACTGCAACGACGGCTTCTGCGAGCT
GTGCGGCTACTCGCGGGCCGAGGTGATGCAGCGACCCTGCACCTGCGACTTCCTGCACGGGCCGCGCACGCAGCGC
CGCGCTGCCGCGCAGATCGCGCAGGCACTGCTGGGCGCCGAGGAGCGCAAAGTGGAAATCGCCTTCTACCGGAAAG
ATGGGAGCTGCTTCCTATGTCTGGTGGATGTGGTGCCCGTGAAGAACGAGGATGGGGCTGTCATCATGTTCATCCT
CAATTTCGAGGTGGTGATGGAGAAGGACATGGTGGGGTCCCCGGCTCATGACACCAACCACCGGGGCCCCCCCACC
AGCTGGCTGGCCCCAGGCCGCGCCAAGACCTTCCGCCTGAAGCTGCCCGCGCTGCTGGCGCTGACGGCCCGGGAGT
CGTCGGTGCGGTCGGGCGGCGCGGGCGGCGCGGGCGCCCCGGGGGCCGTGGTGGTGGACGTGGACCTGACGCCCGC
GGCACCCAGCAGCGAGTCGCTGGCCCTGGACGAAGTGACAGCCATGGACAACCACGTGGCAGGGCTCGGGCCCGCG
GAGGAGCGGCGTGCGCTGGTGGGTCCCGGCTCTCCGCCCCGCAGCGCGCCCGGCCAGCTCCCATCGCCCCGGGCGC
ACAGCCTCAACCCCGACGCCTCGGGCTCCAGCTGCAGCCTGGCCCGGACGCGCTCCCGAGAAAGCTGCGCCAGCGT
```

TABLE 4-continued

Nucleotide sequence of HERG1

GCGCCGCGCCTCGTCGGCCGACGACATCGAGGCCATGCGCGCCGGGGTGCTGCCCCGCCACCGCGCCACGCCAGC

ACCGGGGCCATGCACCCACTGCGCAGCGGCTTGCTCAACTCCACCTCGGACTCCGACCTCGTGCGCTACCGCACCA

TTAGCAAGATTCCCCAAATCACCCTCAACTTTGTGGACCTCAAGGGCGACCCCTTCTTGGCTTCGCCCACCAGTGA

CCGTGAGATCATAGCACCTAAGATAAAGGAGCGAACCCACAATGTCACTGAGAAGGTCACCCAGGTCCTGTCCCTG

GGCGCCGACGTGCTGCCTGAGTACAAGCTGCAGGCACCGCGCATCCACCGCTGGACCATCCTGCATTACAGCCCCT

TCAAGGCCGTGTGGGACTGGCTCATCCTGCTGCTGGTCATCTACACGGCTGTCTTCACACCCTACTCGGCTGCCTT

CCTGCTGAAGGAGACGGAAGAAGGCCCGCCTGCTACCGAGTGTGGCTACGCCTGCCAGCCGCTGGCTGTGGTGGAC

CTCATCGTGGACATCATGTTCATTGTGGACATCCTCATCAACTTCCGCACCACCTACGTCAATGCCAACGAGGAGG

TGGTCAGCCACCCCGGCCGCATCGCCGTCCACTACTTCAAGGGCTGGTTCCTCATCGACATGGTGGCCGCCATCCC

CTTCGACCTGCTCATCTTCGGCTCTGGCTCTGAGGAGCTGATCGGGCTGCTGAAGACTGCGCGGCTGCTGCGGCTG

GTGCGCGTGGCGCGGAAGCTGGATCGCTACTCAGAGTACGGCGCGGCCGTGCTGTTCTTGCTCATGTGCACCTTTG

CGCTCATCGCGCACTGGCTAGCCTGCATCTGGTACGCCATCGGCAACATGGAGCAGCCACACATGGACTCACGCAT

CGGCTGGCTGCACAACCTGGGCGACCAGATAGGCAAACCCTACAACAGCAGCGGCCTGGGCGGCCCCTCCATCAAG

GACAAGTATGTGACGGCGCTCTACTTCACCTTCAGCAGCCTCACCAGTGTGGGCTTCGGCAACGTCTCTCCCAACA

CCAACTCAGAGAAGATCTTCTCCATCTGCGTCATGCTCATTGGCTCCCTCATGTATGCTAGCATCTTCGGCAACGT

GTCGGCCATCATCCAGCGGCTGTACTCGGGCACAGCCCGCTACCACACACAGATGCTGCGGGTGCGGGAGTTCATC

CGCTTCCACCAGATCCCCAATCCCCTGCGCCAGCGCCTCGAGGAGTACTTCCAGCACGCCTGGTCCTACACCAACG

GCATCGACATGAACGCGGTGCTGAAGGGCTTCCCTGAGTGCCTGCAGGCTGACATCTGCCTGCACCTGAACCGCTC

ACTGCTGCAGCACTGCAAACCCTTCCGAGGGGCCACCAAGGGCTGCCTTCGGGCCCTGGCCATGAAGTTCAAGACC

ACACATGCACCGCCAGGGGACACACTGGTGCATGCTGGGGACCTGCTCACCGCCCTGTACTTCATCTCCCGGGGCT

CCATCGAGATCCTGCGGGGCGACGTCGTCGTGGCCATCCTGGGGAAGAATGACATCTTTGGGGAGCCTCTGAACCT

GTATGCAAGGCCTGGCAAGTCGAACGGGGATGTGCGGGCCCTCACCTACTGTGACCTACACAAGATCCATCGGGAC

GACCTGCTGGAGGTGCTGGACATGTACCCTGAGTTCTCCGACCACTTCTGGTCCAGCCTGGAGATCACCTTCAACC

TGCGAGATACCAACATGATCCCGGGCTCCCCCGGCAGTACGGAGTTAGAGGGTGGCTTCAGTCGGCAACGCAAGCG

CAAGTTGTCCTTCCGCAGGCGCACGGACAAGGACACGGAGCAGCCAGGGGAGGTGTCGGCCTTGGGGCCGGGCCGG

GCGGGGGCAGGGCCGAGTAGCCGGGGCCGGCCGGGGGGGCCGTGGGGGGAGAGCCCGTCCAGTGGCCCCTCCAGCC

CTGAGAGCAGTGAGGATGAGGGCCCAGGCCGCAGCTCCAGCCCCCTCCGCCTGGTGCCCTTCTCCAGCCCCAGGCC

CCCCGGAGAGCCGCCGGGTGGGAGCCCCTGATGGAGGACTGCGAGAAGAGCAGCGACACTTGCAACCCCCTGTCA

GGCGCCTTCTCAGGAGTGTCCAACATTTTCAGCTTCTGGGGGACAGTCGGGCCGCCAGTACCAGGAGCTCCCTC

GATGCCCCGCCCCCACCCCAGCCTCCTCAACATCCCCCTCTCCAGCCCGGGTCGGCGGCCCCGGGGCGACGTGGA

GAGCAGGCTGGATGCCCTCCAGCGCCAGCTCAACAGGCTGGAGACCCGGCTGAGTGCAGACATGGCCACTGTCCTG

CAGCTGCTACAGAGGCAGATGACGCTGGTCCCGCCCGCCTACAGTGCTGTGACCACCCCGGGGCCTGGCCCCACTT

CCACATCCCCGCTGTTGCCCGTCAGCCCCTCCCCACCCTCACCTTGGACTCGCTTTCTCAGGTTTCCCAGTTCAT

GGCGTGTGAGGAGCTGCCCCCGGGGGCCCCAGAGCTTCCCCAAGAAGGCCCCACACGACGCCTCTCCCTACCGGGC

CAGCTGGGGGCCCTCACCTCCCAGCCCCTGCACAGACACGGCTCGGACCCGGGCAGTTA

TABLE 5

Nucleotide sequence of K$_v$1-5

SEQ ID NO. 5

```
ATGGAGATCGCCCTGGTGCCCCTGGAGAACGGCGGTGCCATGACCGTCAGAGGAGGCGATGAGGCCCGGGCAGGCT
GCGGCCAGGCCACAGGGGGAGAGCTCCAGTGTCCCCCGACGGCTGGGCTCAGCGATGGGCCCAAGGAGCCGGCGCC
AAAGGGGCGCGCGCAGAGAGACGCGGACTCGGGAGTGCGGCCCTTGCCTCCGCTGCCGGACCCGGGAGTGCGGCCC
TTGCCTCCGCTGCCAGAGGAGCTGCCACGGCCTCGACGGCCGCCTCCCGAGGACGAGGAGGAAGAAGGCGATCCCG
GCCTGGGCACGGTGGAGGACCAGGCTCTGGGCACGGCGTCCCTGCACCACCAGCGCGTCCAAATCAACATCTCCGG
GCTGCGCTTTGAGACGCAGCTGGGCACCCTGGCGCAGTTCCCCAACACACTCCTGGGGGACCCCGCCAAGCGCCTG
CCGTACTTCGACCCCCTGAGGAACGAGTACTTCTTCGACCGCAACCGGCCCAGCTTCGACGGTATCCTCTACTACT
ACCAGTCCGGGGGCCGCCTGCGAGGGGTCAACGTCTCCCTGGACGTGTTCGCGGACGAGATACGCTTCTACCAGCT
GGGGGACGAGGCCATGGAGCGCTTCCGCGAGGATGAGGGCTTCATTAAAGAAGAGGAGAAGCCCCTGCCCCGCAAC
GAGTTCCAGCGCCAGGTGTGGCTTATCTTCGAGTATCCGGAGAGCTCTGGGTCCGCGCGGGCCATCGCCATCGTCT
CGGTCTTGGTTATCCTCATCTCCATCATCACCTTCTGCTTGGAGACCCTGCCTGAGTTCAGGGATGAACGTGAGCT
GCTCCGCCACCCTCCGGCGCCCCACCAGCCTCCCGCGCCCGCCCCTGGGGCAACGGCAGCGGGGTCATGGCCCCC
GCCTCTGGCCCTACGGTGGCACCGCTCCTGCCCAGGACCCTGGCCGACCCCTTCTTCATCGTGGAGACCACGTGCG
TGATCTGGTTCACCTTCGAGCTGCTCGTGCGCTTCTTCGCCTGCCCCAGCAAGGCAGGGTTCTCCCGGAACATCAT
GAACATCATCGATGTGGTGGCCATCTTCCCCTACTTCATCACCCTGGGCACCGAACTGGCAGAGCAGCAGCCAGGG
GGCGGAGGAGGCGCCCAGAATGGGCAGCAGGCCATGTCCCTGGCCATCCTCCGAGTCATCCGCCTGGTCCGGGTGT
TCCGCATCTTCAAGCTCTCCCGCCACTCCAAGGGGCTGCAGATCCTGGGCAAGACCTTGCAGGCCTCCATGAGGGA
GCTGGGGCTGCTCATCTTCTTCCTCTTCATCGGGGTCATCCTCTTCTCCAGTGCCGTCTACTTCGCAGAGGCTGAC
AACCAGGGAACCCATTTCTCTAGCATCCCTGACGCCTTCTGGTGGGCAGTGGTCACCATGACCACTGTGGGCTACG
GGGACATGAGGCCCATCACTGTTGGGGGCAAGATCGTGGGCTCGCTGTGTGCCATCGCCGGGGTCCTCACCATTGC
CCTGCCTGTGCCCGTCATCGTCTCCAACTTCAACTACTTCTACCACCGGGAAACGGATCACGAGGAGCCGGCAGTC
CTTAAGGAAGAGCAGGGCACTCAGAGCCAGGGGCCGGGGCTGGACAGAGGAGTCCAGCGGAAGGTCAGCGGGAGCA
GGGGATCCTTCTGCAAGGCTGGGGGGACCCTGGAGAATGCAGACAGTGCCCGAAGGGGCAGCTGCCCCCTAGAGAA
GTGTAACGTCAAGGCCAAGAGCAACGTGGACTTGCGGAGGTCCCTTTATGCCCTCTGCCTGGACACCAGCCGGGAA
ACAGATTTGTGA
```

TABLE 6

Nucleotide sequence of IRK1

SEQ ID NO. 6

```
ATGGGCAGTGTGCGAACCAACCGCTATAGCATTGTCTCTTCGGAAGAGGACGGCATGAAGTTGGCCACCATGGCAG
TTGCCAATGGCTTTGGGAATGGGAAAAGTAAAGTCCACACTCGGCAACAGTGTAGGAGCCGCTTTGTGAAGAAAGA
TGGCCACTGTAATGTTCAGTTCATCAACGTTGGGGAAAAGGGACAACGGTACCTTGCTGACATTTTTACTACGTGT
GTGGACATTCGCTGGCGGTGGATGCTGGTTATCTTTTGCCTAGCTTTTGTTCTCTCGTGGCTGTTTTTGGCTGTG
TGTTTTGGCTGATAGCTTTGCTCCATGGAGATCTGGATGCATCTAAGGAGAGCAAAGCCTGTGTGTCTGAGGTCAA
CAGCTTCACAGCTGCCTTTCTTTTCTCCATTGAGACCCAGACAACCATCGGCTATGGGTTCCGATGTGTCACGGAT
GAATGCCCGATTGCGGTGTTCATGGTTGTGTTCCAGTCAATTGTGGGCTGCATTATTGATGCTTTTATCATTGGTG
CCGTCATGGCAAAGATGGCAAAGCCAAAGAAAAGAAATGAGACTCTTGTCTTCAGTCACAATGCTGTGATTGCCAT
GAGAGATGGCAAGCTGTGTTTGATGTGGCGAGTAGGCAACCTTCGGAAAAGCCACTTGGTAGAAGCTCATGTTCGA
```

TABLE 6-continued

Nucleotide sequence of IRK1

GCCCAGCTCCTCAAATCCAGAATTACTTCTGAAGGGGAATACATCCCCTTGGATCAAATAGACATCAATGTTGGCT

TTGACAGTGGAATTGACCGTATATTTCTGGTATCCCCAATCACTATTGTCCATGAAATAGATGAAGATAGTCCTTT

ATATGATTTGAGCAAGCAGGACATTGATAATGCAGACTTTGAAATTGTTGTGATACTAGAAGGCATGGTGGAAGCC

ACTGCCATGACAACACAGTGTCGTAGTTCTTATTTGGCCAACGAGATCCTTTGGGGCCACCGCTATGAGCCAGTGC

TCTTTGAGGAGAAGCACTACTATAAAGTGGACTATTCGAGGTTTCATAAGACTTACGAAGTACCCAACACTCCCCT

TTGTAGTGCCAGAGACTTAGCAGAAAAGAAATATATTCTCTCAAATGCTAACTCATTTTGCTATGAAAATGAAGTT

GCCCTTACAAGCAAAGAGGAAGATGACAGTGAAAATGGGGTTCCAGAAAGCACCAGTACAGACACACCTCCTGACA

TCGACCTTCACAACCAGGCAAGTGTACCTCTAGAGCCCAGACCCTTACGGCGAGAATCGGAGATATGA

TABLE 7

Nucleotides 4307-5425 of SEQ ID NO. 31: human ROMK2 (Genbank accession number U12542)

AATGTTCAACATCTTCGGAAATGGGTCGTCACTCGCTTTTTTGGGCATTCTCGGCAAAGAGCAAGGCTAGTCTCCA

AAGATGGAAGGTGCAACATAGAATTTGGCAATGTGGAGGCACAGTCAAGGTTTATATTCTTTGTGGACATCTGGAC

AACGGTACTTGACCTCAAGTGGAGATACAAAATGACCATTTTCATCACAGCCTTCTTGGGGAGTTGGTTTTTCTTT

GGTCTCCTGTGGTATGCAGTAGCGTACATTCACAAAGACCTCCCGGAATTCCATCCTTCTGCCAATCACACTCCCT

GTGTGGAGAATATTAATGGCTTGACCTCAGCTTTTCTGTTTTCTCTGGAGACTCAAGTGACCATTGGATATGGATT

CAGGTGTGTGACAGAACAGTGTGCCACTGCCATTTTTCTGCTTATCTTTCAGTCTATACTTGGAGTTATAATCAAT

TCTTTCATGTGTGGGGCCATCTTAGCCAAGATCTCCAGGCCCAAAAAACGTGCCAAGACCATTACGTTCAGCAAGA

ACGCAGTGATCAGCAAACGGGGAGGGAAGCTTTGCCTCCTAATCCGAGTGGCTAATCTCAGGAAGAGCCTTCTTAT

TGGCAGTCACATTTATGGAAAGCTTCTGAAGACCACAGTCACTCCTGAAGGAGAGACCATTATTTTGGACCAGATC

AATATCAACTTTGTAGTTGACGCTGGGAATGAAAATTTATTCTTCATCTCCCCATTGACAATTTACCATGTCATTG

ATCACAACAGCCCTTTCTTCCACATGGCAGCGGAGACCCTTCTCCAGCAGGACTTTGAATTAGTGGTGTTTTTAGA

TGGCACAGTGGAGTCCACCAGTGCTACCTGCCAAGTCCGGACATCCTATGTCCCAGAGGAGGTGCTTTGGGGCTAC

CGTTTTGCTCCCATAGTATCCAAGACAAAGGAAGGGAAATACCGAGTGGATTTCCATAACTTTAGCAAGACAGTGG

AAGTGGAGACCCCTCACTGTGCCATGTGCCTTTATAATGAGAAAGATGTTAGAGCCAGGATGAAGAGAGGCTATGA

CAACCCCAACTTCATCTTGTCAGAAGTCAATGAAACAGATGACACCAAAATGTAA

TABLE 8

HERG in Δtrk1Δtrk2Δtok1 in DPM -HIS medium
with 0.5 mM CsCl as activator after 38 hours growth.
Starting culture 0.03 OD. Detection OD620 nm.

| Inhibitors (30 μM) | Exp. 1 | Exp. 2 | Exp. 3 | Exp. 4 | Mean growth | St. Dev. |
|---|---|---|---|---|---|---|
| Terfenadine | 0.006 | 0.006 | 0.005 | 0.007 | 0.006 | 0.0 |
| Pimozide | 0.004 | 0.004 | 0.005 | 0.005 | 0.0045 | 0.0 |
| Diphenhydramine | 0.095 | 0.151 | 0.17 | 0.186 | 0.1505 | 0.04 |
| Ziprasidone | 0.006 | 0.01 | 0.012 | 0.015 | 0.01075 | 0.0 |
| Fexofenadine | 0.082 | 0.144 | 0.159 | 0.156 | 0.13525 | 0.0 |
| Serlindole | 0.007 | 0.004 | 0.007 | 0.005 | 0.00575 | 0.0 |

TABLE 8-continued

| | | | | | | |
|---|---|---|---|---|---|---|
| Loratadine | 0.024 | 0.016 | 0.062 | 0.014 | 0.029 | 0.0 |
| DMSO control | 0.162 | 0.163 | 0.136 | 0.146 | 0.15175 | 0.0 |

Wild-type cells in DPM medium with 5 mM or 80 mM KCl after 24 hours growth.
Starting culture 0.01 OD. Detection at OD 620 nm.

| | 5 mM KCl | | | | | StD | 80 mM KCl | | | | | StD |
|---|---|---|---|---|---|---|---|---|---|---|---|---|
| DMSO | 2.791 | 3.437 | 3.959 | 3.875 | 3.5155 | 0.5 | 3.814 | 3.959 | 3.319 | 3.959 | 3.7 | 0.3 |
| Pimo (30 μM) | 0.904 | 0.823 | 0.305 | 0.614 | 0.6615 | 0.27 | 3.673 | 3.505 | 3.46 | 3.441 | 3.5 | 0.1 |
| Zipra (30 μM) | 0.943 | 0.877 | 0.675 | 0.701 | 0.799 | 0.1 | 0.836 | 0.681 | 0.717 | 0.606 | 0.7 | 0.1 |
| control | 2.953 | 2.902 | 3.781 | 3.353 | 3.24725 | 0.4 | 3.228 | 3.264 | 3.781 | 3.947 | 3.6 | 0.4 |

TABLE 9

| Inhibitors (30 μM) | Exp. 1 | Exp. 2 | Exp. 3 | Exp. 4 | Mean growth | St. Dev. |
|---|---|---|---|---|---|---|
| LacZ in wild-type cells in DPM -HIS/-TRP medium with 0.5 mM CsCl as activator after 24 hours growth; detection with the TROPIX kit. ASSAY 1 | | | | | | |
| Terfenadine | 4497 | 4481 | 5058 | 5381 | 4854.25 | 441.936176 |
| Pimozide | 357.4 | 747.9 | 804.6 | 585.4 | 623.825 | 200.443648 |
| Diphenhydramine | 2806 | 3181 | 4178 | 4864 | 3757.25 | 937.881789 |
| Ziprasidone | 55.32 | 70.29 | 70.3 | 77.18 | 68.2725 | 9.22481933 |
| Fexofenadine | 3326 | 2938 | 3377 | 4659 | 3575 | 748.783458 |
| Sertindole | 4165 | 2099 | 4588 | 3069 | 3480.25 | 1121.45304 |
| Loratadine | 4905 | 5141 | 1857 | 3266 | 3792.25 | 1536.17173 |
| DMSO control | 3172 | 4129 | 4984 | 5077 | 4340.5 | 888.190858 |
| LacZ in wild-type cells in DPM -HIS/-TRP medium with 0.5 mM CsCl as activator after 24 hours growth; detection with TROPIX-kit. ASSAY 2 | | | | | | |
| Terfenadine (0.5 Cs) | 3439 | 3795 | 3698 | 3388 | 3580 | 197.394698 |
| Pimozide (0.5 Cs) | 905 | 2176 | 496.5 | 573.4 | 1037.725 | 779.2749 |
| Diphenhydramine (0.5 Cs) | 3468 | 2980 | 3062 | 3561 | 3267.75 | 289.383684 |
| Ziprasidone (0.5 Cs) | 62.52 | 44.3 | 49.71 | 51.87 | 52.1 | 7.64158361 |
| Fexofenadine (0.5 Cs) | 3533 | 3502 | 3661 | 3569 | 3566.25 | 68.8446318 |
| Sertindole (0.5 Cs) | 3992 | 3076 | 3972 | 2782 | 3455.5 | 619.738386 |
| Loratadine (0.5 Cs) | 3553 | 1965 | 3590 | 2478 | 2896.5 | 807.211042 |
| DMSO control (0.5 Cs) | 3520 | 3218 | 3460 | 3087 | 3321.25 | 203.540946 |

TABLE 10

HERG in Δtrk1Δtrk2Δtok1 in DPM -HIS medium with 0.5 mM CsCl as activator after 38 hours growth.
Starting culture 0.03 OD. Detection at OD 620 nm.

| Inhibitors (30 μM) | Exp. 1 | Exp. 2 | Exp. 3 | Exp. 4 | Mean growth | St. Dev. |
|---|---|---|---|---|---|---|
| Terfenadine | 0.006 | 0.006 | 0.005 | 0.007 | 0.006 | 0.0008165 |
| Pimozide | 0.004 | 0.004 | 0.005 | 0.005 | 0.0045 | 0.00057735 |
| Diphenhydramine | 0.095 | 0.151 | 0.17 | 0.186 | 0.1505 | 0.03966947 |
| Ziprasidone | 0.006 | 0.01 | 0.012 | 0.015 | 0.01075 | 0.00377492 |
| Fexofenadine | 0.082 | 0.144 | 0.159 | 0.156 | 0.13525 | 0.0360867 |
| Sertindole | 0.007 | 0.004 | 0.007 | 0.005 | 0.00575 | 0.0015 |
| Loratadine | 0.024 | 0.016 | 0.062 | 0.014 | 0.029 | 0.02242023 |
| DMSO control | 0.162 | 0.163 | 0.136 | 0.146 | 0.15175 | 0.01307351 |

TABLE 11

Wild-type cells in DPM medium with 5 mM or 80 mM KCl after 24 hours growth. Starting culture 0.01 OD.
Detection at OD 620 nm.

| | 5 mM KCl | | | | | StD | 80 mM KCl | | | | | StD |
|---|---|---|---|---|---|---|---|---|---|---|---|---|
| DMSO | 2.791 | 3.437 | 3.959 | 3.875 | 3.5155 | 0.53447638 | 3.814 | 3.959 | 3.319 | 3.959 | 3.76275 | 0.30362738 |
| Pimo (30 μM) | 0.904 | 0.823 | 0.305 | 0.614 | 0.6615 | 0.26723086 | 3.673 | 3.505 | 3.46 | 3.441 | 3.51975 | 0.10563262 |
| Zipra (30 μM) | 0.943 | 0.877 | 0.675 | 0.701 | 0.799 | 0.13140269 | 0.836 | 0.681 | 0.717 | 0.606 | 0.71 | 0.09588535 |
| control | 2.953 | 2.902 | 3.781 | 3.353 | 3.24725 | 0.40900397 | 3.228 | 3.264 | 3.781 | 3.947 | 3.555 | 0.36347856 |

TABLE 12 p423GPD (YM194) and p423GPD-ROMK2 (YM256) in Δtrk1Δtrk2Δtok1 in DPM -HIS 5 mM KCl, pH 6.5 after 24 hours growth; starting OD 0.01. Averages

|  | 194 | SD | 256 | SD |
|---|---|---|---|---|
| DMSO (0.5%) | 0.023 | 0.0036 | 0.19 | 0.013 |
| Cells | 0.028 | 0.0012 | 0.23 | 0.011 |
| 2 mM RbCl | 0.048 | 0.0052 | 0.44 | 0.033 |

TABLE 12-continued p423GPD (YM194) and p423GPD-ROMK2 (YM256) in Δtrk1Δtrk2Δtok1 in DPM -HIS 5 mM KCl, pH 6.5 after 24 hours growth; starting OD 0.01. Averages

| Signal to noise ratio | |
|---|---|
|  | S/N |
| DMSO (0.5%) | 8.2 |
| Cells | 8.3 |
| 2 mM RbCl | 8.46 |

TABLE 13

Nucleotide sequence of p423 GPD-hROMK2
(Accession No. U 12542)

SEQ ID NO. 31

```
gacgaaagggcctcgtgatacgcctatttttataggttaatgtcatgataataatggtttcttagatgatccaatatcaaagg aaatgatagcattgaaggatgagactaatccaattgaggagtggcagcatatagaacagctaaagggtagtgctgaag gaagcatacgatacccgcatggaatgggataatatcacaggaggtactagactacctttcatcctacataaatagacg catataagtacgcatttaagcataaacacgcactatgccgttcttctcatgtatatatatacaggcaacacgcagatata ggtgcgacgtgaacagtgagctgtatgtgcgcagctcgcgttgcattttcggaagcgctcgtttcggaaacgctttgaagt tcctattccgaagttcctattctctagaaagtataggaacttcagagcgcttttgaaaaccaaaagcgctctgaagacgca ctttcaaaaaaccaaaaacgcaccggactgtaacgagctactaaaatattgcgaataccgcttccacaaacattgctca aaagtatctctttgctatatatctgtgctatatccctatataacctacccatccacctttcgctccttgaacttgcatctaaact cgacctctacatttttatgtttatctctagtattactctttagacaaaaaaattgtagtaagaactattcatagagtgaatcgaa aacaatacgaaaatgtaaacatttcctatacgtagtatatagagacaaaatagaagaaaccgttcataattttctgaccaa tgaagaatcatcaacgctatcactttctgttcacaaagtatgcgcaatccacatcggtatagaatataatcggggatgccttt atcttgaaaaaatgcacccgcagcttcgctagtaatcagtaaacgcgggaagtggagtcaggcttttttttatggaagaga aaatagacaccaaagtagccttcttctaaccttaacggacctacagtgcaaaaagttatcaagagactgcattatagagc gcacaaaggagaaaaaagtaatctaagatgctttgttagaaaaatagcgctctcgggatgcattttttgtagaacaaaa aagaagtatagattctttgttggtaaaatagcgctctcgcgttgcatttctgttctgtaaaaatgcagctcagattctttgtttgaa aaattagcgctctcgcgttgcatttttgttttacaaaaatgaagcacagattcttcgttggtaaaatagcgctttcgcgttgcatt tctgttctgtaaaaatgcagctcagattctttgtttgaaaaattagcgctctcgcgttgcattttgttctacaaaatgaagcaca gatgcttcgttcaggtggcacttttcggggaaatgtgcgcggaacccctatttgtttattttctaaatacattcaaatatgtatc cgctcatgagacaataaccctgataaatgcttcaataatattgaaaaggaagagtatgagtattcaacatttccgtgtcg cccttattccctttttttgcggcattttgccttcctgttttttgctcacccagaaacgctggtgaaagtaaaagatgctgaagatca gttgggtgcacgagtgggttacatcgaactggatctcaacagcggtaagatccttgagagttttcgccccgaagaacgttt tccaatgatgagcacttttaaagttctgctatgtggcgcggtattatcccgtattgacgccgggcaagagcaactcggtcgc cgcatacactattctcagaatgacttggttgagtactcaccagtcacagaaaagcatcttacggatggcatgacagtaag agaattatgcagtgctgccataaccatgagtgataacactgcggccaacttacttctgacaacgatcggaggaccgaag gagctaaccgcttttttgcacaacatgggggatcatgtaactcgccttgatcgttgggaaccggagctgaatgaagccata ccaaacgacgagcgtgacaccacgatgcctgtagcaatggcaacaacgttgcgcaaactattaactggcgaactactt actctagcttcccggcaacaattaatagactggatggaggcggataaagttgcaggaccacttctgcgctcggcccttcc ggctggctggtttattgctgataaatctggagccggtgagcgtgggtctcgcggtatcattgcagcactggggccagatgg
```

TABLE 13-continued

Nucleotide sequence of p423 GPD-hROMK2
(Accession No. U 12542)

```
taagccctcccgtatcgtagttatctacacgacggggagtcaggcaactatggatgaacgaaatagacagatcgctgag
ataggtgcctcactgattaagcattggtaactgtcagaccaagtttactcatatatactttagattgatttaaaacttcatttttaa
tttaaaaggatctaggtgaagatcctttttgataatctcatgaccaaaatcccttaacgtgagttttcgttccactgagcgtca
gaccccgtagaaaagatcaaaggatcttcttgagatcctttttttctgcgcgtaatctgctgcttgcaaacaaaaaaaccac
cgctaccagcggtggtttgtttgccggatcaagagctaccaactctttttccgaaggtaactggcttcagcagagcgcaga
taccaaatactgtccttctagtgtagccgtagttaggccaccacttcaagaactctgtagcaccgcctacatacctcgctct
gctaatcctgttaccagtggctgctgccagtggcgataagtcgtgtcttaccgggttggactcaagacgatagttaccggat
aaggcgcagcggtcgggctgaacggggggttcgtgcacacagcccagcttggagcgaacgacctacaccgaactg
agatacctacagcgtgagctatgagaaagcgccacgcttcccgaagggagaaaggcggacaggtatccggtaagcg
gcagggtcggaacaggagagcgcacgagggagcttccaggggaaacgcctggtatctttatagtcctgtcgggtttc
gccacctctgacttgagcgtcgatttttgtgatgctcgtcaggggggcggagcctatggaaaaacgccagcaacgcggc
cttttacggttcctgcctttgctggccttttgctcacatgttctttcctgcgttatcccctgattctgtggataaccgtattaccgc
ctttgagtgagctgataccgctcgccgcagccgaacgaccgagcgcagcgagtcagtgagcgaggaagcggaaga
gcgcccaatacgcaaaccgcctctccccgcgcgttggccgattcattaatgcagctggcacgacaggtttcccgactgg
aaagcgggcagtgagcgcaacgcaattaatgtgagttacctcactcattaggcaccccaggctttacactttatgcttccg
gctcctatgttgtgtggaattgtgagcggataacaatttcacacaggaaacagctatgaccatgattacgccaagcgcgc
aattaaccctcactaaagggaacaaaagctggagctcagtttatcattatcaatactgccatttcaaagaatacgtaaata
attaatagtagtgattttcctaactttatttagtcaaaaaattagccttttaattctgctgtaacccgtacatgcccaaaatagggt
ggcgggttacacagaatatataacatcgtaggtgtctgggtgaacagtttattcctggcatccactaaatataatggagcc
cgcttttaagctggcatccagaaaaaaaagaatcccagcaccaaaatattgttttcttcaccaaccatcagttcataggt
ccattctcttagcgcaactacagagaacaggggcacaaacaggcaaaaaacgggcacaacctcaatggagtgatgc
aacctgcctggagtaaatgatgacacaaggcaattgacccacgcatgtatctatctcattttcttacaccttctattaccttctg
ctctctctgatttggaaaaagctgaaaaaaaaggttgaaaccagttccctgaaattattcccctacttgactaataagtatat
aaagacggtaggtattgattgtaattctgtaaatctatttcttaaacttcttaaattctacttttatagttagtctttttttttagttttaaa
acaccagaacttagtttcgacggattctagaactagtggatccccgggctgcagccatgttcaaacatcttcggaaatg
ggtcgtcactcgcttttttgggcattctcggcaaagagcaaggctagtctccaaagatggaaggtgcaacatagaatttgg
caatgtggaggcacagtcaaggtttatattctttgtggacatctggacaacggtacttgacctcaagtggagatacaaaat
gaccattttcatcacagccttcttggggagttggttttctttggtctcctgtggtatgcagtagcgtacattcacaaagacctcc
cggaattccatccttctgccaatcacactccctgtgtggagaatattaatggcttgacctcagcttttctgttttctctggagact
caagtgaccattggatatggattcaggtgtgtgacagaacagtgtgccactgccattttctgcttatctttcagtctatacttg
gagttataatcaattctttcatgtgtggggccatcttagccaagatctccaggcccaaaaaacgtgccaagaccattacgtt
cagcaagaacgcagtgatcagcaaacgggagggaagctttgcctcctaatccgagtggctaatctcaggaagagcc
ttcttattggcagtcacatttatggaaagcttctgaagaccacagtcactcctgaaggagagaccattattttggaccagatc
aatatcaactttgtagttgacgctgggaatgaaaatttattcttcatctccccattgacaatttaccatgtcattgatcacaaca
gccctttcttccacatggcagcggagacccttctccagcaggactttgaattagtggtgttttttagatggcacagtggagtcc
accagtgctacctgccaagtccggacatcctatgtcccagaggaggtgctttgggctaccgttttgctcccatagtatcca
agacaaaggaagggaaataccgagtggatttccataactttagcaagacagtggaagtggagacccctcactgtgcc
atgtgcctttataatgagaaagatgttagagccaggatgaagagaggctatgacaaccccaacttcatcttgtcagaagt
```

TABLE 13-continued

Nucleotide sequence of p423 GPD-hROMK2
(Accession No. U 12542)

```
caatgaaacagatgacaccaaaatgtaacagtcgacctcgagtcatgtaattagttatgtcacgcttacattcacgccctc
cccccacatccgctctaaccgaaaaggaaggagttagacaacctgaagtctaggtccctatttatttttttatagttatgttag
tattaagaacgttatttatatttcaaattttctttttttttctgtacagacgcgtgtacgcatgtaacattatactgaaaaccttgcttg
agaaggttttgggacgctcgaaggctttaatttgcggccggtacccaattcgccctatagtgagtcgtattacgcgcgctca
ctggccgtcgttttacaacgtcgtgactgggaaaaccctggcgttacccaacttaatcgccttgcagcacatccccctttcg
ccagctggcgtaatagcgaagaggcccgcaccgatcgcccttcccaacagttgcgcagcctgaatggcgaatggcgc
gacgcgccctgtagcggcgcattaagcgcggcgggtgtggtggttacgcgcagcgtgaccgctacacttgccagcgcc
ctagcgcccgctccttcgctttcttcccttcctttctcgccacgttcgccggctttccccgtcaagctctaaatcgggggctcc
ctttagggttccgatttagtgctttacggcacctcgaccccaaaaaacttgattagggtgatggttcacgtagtgggccatcg
ccctgatagacggtttttcgccctttgacgttggagtccacgttctttaatagtggactcttgttccaaactggaacaacactc
aaccctatctcggtctattcttttgatttataagggattttgccgatttcggcctattggttaaaaaatgagctgatttaacaaaa
atttaacgcgaattttaacaaaatattaacgtttacaatttcctgatgcggtattttctccttacgcatctgtgcggtatttcacac
cgcatagatccgtcgagttcaagagaaaaaaaagaaaaagcaaaaagaaaaaaggaaagcgcgcctcgttcag
aatgacacgtatagaatgatgcattaccttgtcatcttcagtatcatactgttcgtatacatacttactgacattcataggtata
catatatacacatgtatatatatcgtatgctgcagctttaaataatcggtgtcactacataagaacacctttggtggagggaa
catcgttggtaccattgggcgaggtggcttctcttatggcaaccgcaagagccttgaacgcactctcactacggtgatgat
cattcttgcctcgcagacaatcaacgtggagggtaattctgctagcctctgcaaagctttcaagaaaatgcgggatcatct
cgcaagagagatctcctactttctcccttttgcaaaccaagttcgacaactgcgtacggcctgttcgaaagatctaccaccg
ctctggaaagtgcctcatccaaaggcgcaaatcctgatccaaaccttttttactccacgcgccagtagggcctctttaaaag
cttgaccgagagcaatcccgcagtcttcagtggtgtgatggtcgtctatgtgtaagtcaccaatgcactcaacgattagcg
accagccggaatgcttggccagagcatgtatcatatggtccagaaacctataacctgtgtggacgttaatcacttgcgatt
gtgtggcctgttctgctactgcttctgcctcttttctgggaagatcgagtgctctatcgctaggggaccacccttttaaagagat
cgcaatctgaatcttggtttcatttgtaatacgctttactagggcttctgctctgtcatctttgccttcgtttatcttgcctgctcatttt
ttagtatattcttcgaagaaatcacattactttatataatgtataattcattatgtgataatgccaatcgctaagaaaaaaaaa
gagtcatccgctagggaaaaaaaaaatgaaatcattaccgaggcataaaaaaatatagagtgtactagaggag
gccaagagtaatagaaaagaaaattgcgggaaaggactgtgttatgacttccctgactaatgccgtgttcaaacgata
cctggcagtgactcctagcgctcaccaagctcttaaaacgggaatttatggtgcactctcagtacaatctgctctgatgccg
catagttaagccagccccgacacccgccaacacccgctgacgcgccctgacgggcttgtctgctcccggcatccgctta
cagacaagctgtgaccgtctccgggagctgcatgtgtcagaggttttcaccgtcatcaccgaaacgcgcga
```

The invention claimed is:

1. A process for identifying inhibitors of a human potassium channel,
   a) providing a mutated *S. cerevisiae* cell which does not express the three endogenous potassium channels TRK1, TRK2 and TOK1 and which is not complemented by an expressed HERG1;
   b) treating said mutated cell with a mutated Kv1.5 human potassium channel wherein said human potassium channel is expressed heterologously in this mutated *S. cerevisiae* cell;
   c) incubating the *S. cerevisiae* cell expressing the human potassium channel together with a substance to be tested; and
   d) determining the effect of the substance to be tested on the human potassium channel, wherein a decrease in the transport of potassium across the human potassium channel indicates that the substance is an inhibitor if the human potassium channel.

2. The process as claimed in claim 1, wherein the genes TRK1, TRK2 and TOK1 are switched off in the mutated *S. cerevisiae* cell (Δtrk1, Δtrk2, Δtok1).

3. The process as claimed in claim 2, wherein the human potassium channel is present in a yeast expression plasmid.

4. The process as claimed in claim 2, wherein the mutated *S. cerevisiae* cell expresses constitutively a growth reporter.

5. The process as claimed in claim 4, wherein the substance to be tested, which has an effect on the human potassium channel, inhibits the growth of the mutated *S. cerevisiae* cell.

6. The process as claimed in claim 4, wherein the effect of the substance to be tested on the human potassium channel is determined by measuring the cell count of the mutated *S. cerevisiae* cells.

7. The process as claimed in claim 6, wherein the cell count is determined via fluorescence or luminescence of the constitutively expressed growth reporter.

8. A process of identifying activators of a human potassium channel,
   a) providing a mutated *S. cerevisiae* cell which does not express the three endogenous potassium channels TRK1, TRK2 and TOK1 and which is not complemented by an expressed HERG1;
   b) reacting said mutated cell with a mutant Kv1.5 human potassium channel wherein said human potassium channel is expressed heterologously in this mutated *S. cerevisiae* cell;
   c) incubating the *S. cerevisiae* cell expressing the human potassium channel together with a substance to be tested; and
   d) determining the effect of the substance to be tested on the human potassium channel wherein an increase in the transport of potassium across the human potassium channel indicates that the substance is an activator of the human potassium channel.

9. A process of identifying activators of a human potassium channel,
   a) providing a mutated *S. cerevisiae* cell which does not express the three endogenous potassium channels TRK1, TRK2 and TOK1 and which is not complemented by an expressed HERG1;
   b) reacting said mutated cell with a mutant Kv1.5 human potassium channel wherein said human potassium channel is expressed heterologously in this mutated *S. cerevisiae* cell;
   c) incubating the mutated *S. cerevisiae* cell expressing the human potassium channel together with a substance to be tested in the presence of an inhibitor of the human potassium channel; and
   d) determining the effect of the substance to be tested on the human potassium channel wherein an increase in the transport of potassium across the human potassium channel indicates that the substance is an activator of the human potassium channel.

* * * * *